(12) United States Patent
Forrest et al.

(10) Patent No.: US 8,088,412 B2
(45) Date of Patent: Jan. 3, 2012

(54) INTRALYMPHATIC CHEMOTHERAPY DRUG CARRIERS

(75) Inventors: Laird Forrest, Lawrence, KS (US); Mark Cohen, Overland Park, KS (US); Shuang Cai, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 211 days.

(21) Appl. No.: 12/363,302

(22) Filed: Jan. 30, 2009

(65) Prior Publication Data

US 2009/0191152 A1 Jul. 30, 2009

Related U.S. Application Data

(60) Provisional application No. 61/024,837, filed on Jan. 30, 2008.

(51) Int. Cl.
*A61K 9/14* (2006.01)
*A61K 38/00* (2006.01)
(52) U.S. Cl. .................................. 424/489; 514/19.2
(58) Field of Classification Search .................. None
See application file for complete search history.

(56) References Cited

U.S. PATENT DOCUMENTS

| 5,635,603 | A * | 6/1997 | Hansen et al. ............ 530/391.5 |
| 6,585,956 | B2 | 7/2003 | Malik |
| 2003/0180382 | A1* | 9/2003 | Brown et al. ................. 424/649 |
| 2006/0116346 | A1* | 6/2006 | De Luca et al. .................. 514/54 |
| 2006/0204443 | A1* | 9/2006 | Kobayashi et al. ........... 424/9.32 |
| 2007/0041934 | A1* | 2/2007 | William et al. ............. 424/78.3 |

FOREIGN PATENT DOCUMENTS

| CN | 1267214 | | 9/2000 |
| CN | 1705683 | A | 12/2005 |
| KR | 2009/0040979 | A | 4/2009 |
| WO | 99/00113 | A1 | 1/1999 |
| WO | 2004/035629 | A2 | 4/2004 |
| WO | WO 2006113668 | A1 * | 10/2006 |

OTHER PUBLICATIONS

Oussoren et al., Advanced Drug Delivery Reviews, 2002, 50:143-156.*
Akima et al. J. Drug Targeting, 1996, 4:1-8.*
Jeong et al., Journal of Pharmaceutical Science, 2008, 97(3):1268-1276.*
Auzenne, Edmond, et al., Hyaluronic Acid-Paclitaxel: Antitumor Efficacy against CD44(+) Human Ovarian Carcinoma Xenografts, Neoplasia, Jun. 2007, pp. 479-486, vol. 9, No. 6.
Cera, C., et al., Water-soluble polysaccharide-anthracycline conjugates: biological activity, Anti-Cancer Drug Design, 1992, pp. 143-151, vol. 7, Oxford University Press.
Gouin, Sebastien and Winnik, Francoise M., Quantitative Assays of the Amount of Diethylenetriaminepentaacetic Acid Conjugated to Water-Soluble Polymers Using Isothermal Titration Calorimetry and Colorimetry, Bioconjugate Chem., 2001, pp. 372-377, vol. 12, American Chemical Society.
Jaracz, Stanislav, et al., Recent Advances in Tumor-Targeting Anticancer Drug Conjugates, Bioorganic & Medicinal Chemistry, 2005, pp. 5043-5054, vol. 13. (Not included).
Jeong, Young-Il, et al., Cisplatin-Incorporated Hyaluronic Acide Nanoparticles Based on Ion-Complex Formation, Journal of Pharmaceutical Sciences, 2007, pp. 1-9, Wiley-Liss, Inc. and the American Pharmacists Association.
Luo, Yi, et al., A Hyaluronic Acid—Taxol Antitumor Bioconjugate Targeted to Cancer Cells, Biomacromolecules, 2000, pp. 208-218, vol. 1, American Chemical Society.
Luo, Yi and Prestwich, Glenn D., Synthesis and Selective Cytotoxicity of a Hyaluronic Acid-Antitumor Bioconjugate, Bioconjugate Chem., 1999, pp. 755-763, vol. 10, American Chemical Society.
Sugahara, Shuichi, et al., Characteristics of Tissue Distribution of Various Polysaccharides as Drug Carriers: Influences of Molecular Weight and Anionic Charge on Tumor Targeting, Biol. Pharm. Bull., 2001, pp. 535-543, vol. 24 (5), Pharmaceutical Society of Japan.
Office Action(with English translation) issued Aug. 10, 2011 by SIPO for corresponding Chinese application No. 200980108315.5, 12 pages.

* cited by examiner

*Primary Examiner* — Hong Sang

(57) ABSTRACT

A chemotherapeutic composition can be configured for subcutaneous administration for preferential intralymphatic accumulation while also providing a therapeutic systemic concentration that is not toxic. The composition can include a pharmaceutically acceptable carrier, and a nanoconjugate configured for preferential intralymphatic accumulation after subcutaneous administration. The nanoconjugate can include a nanocarrier configured for preferential intralymphatic accumulation after subcutaneous or interstitial administration, and a plurality of chemotherapeutic agents coupled to the nanocarrier. The nanoconjugate can have a dimension of about 10 nm to about 50 nm. Also, the nanoconjugate can be loaded with the chemotherapeutic agents from about 10% to about 50% w/w. The nanocarrier can be a hyaluronan polymer of about 3 kDa to about 50 kDa. Alternatively, the nanocarrier can be a dendrimer.

8 Claims, 32 Drawing Sheets s.q. HA control i.v. CDDP (3.3 mg/kg)

s.q. HA-Pt (3.3 mg/kg)

s.q. HA-Pt with Ag (1 mg/kg)

i.v. CDDP (1 mg/kg)

s.q. HA-Pt (1 mg/kg)

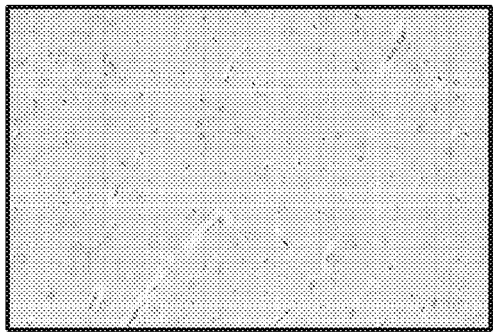
FIG. 5A — s.q. HA control
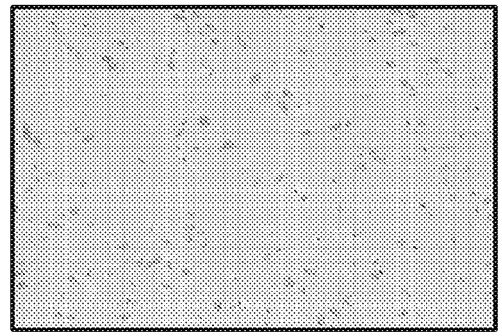
FIG. 5B — i.v. CDDP (3.3 mg/kg)
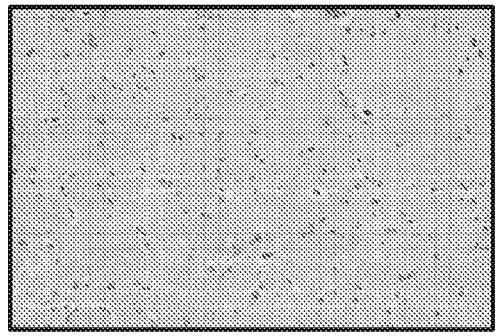
FIG. 5C — s.q. HA-Pt (3.3 mg/kg)
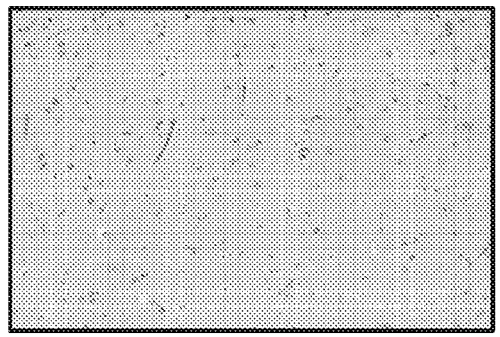
FIG. 5D — s.q. HA-Pt with Ag (1 mg/kg)
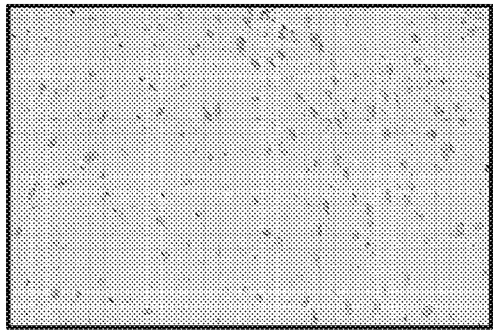
FIG. 5E — i.v. CDDP (1 mg/kg)
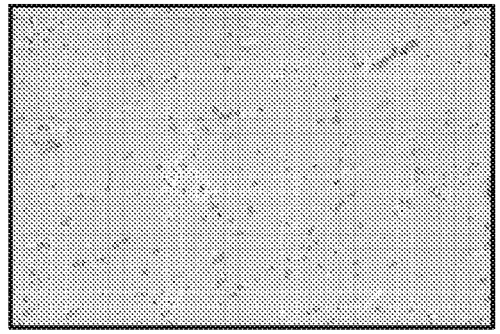
FIG. 5F — s.q. HA-Pt (1 mg/kg)

s.q. HA control s.q. HA-Pt (3.3 mg/kg)

s.q. HA-Pt with Ag (1 mg/kg)

s.q. HA-Pt (1 mg/kg)

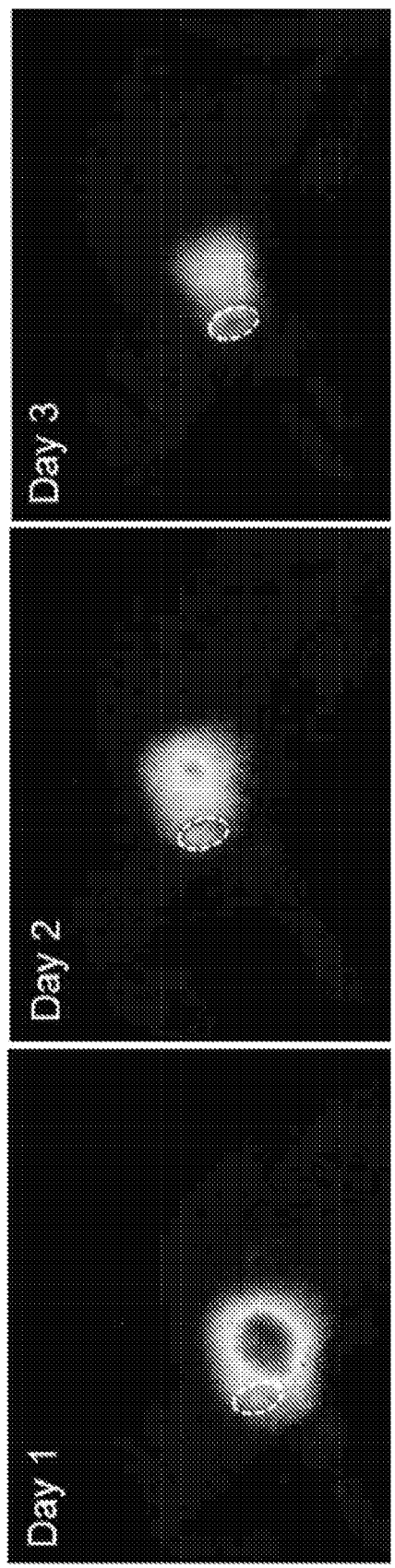
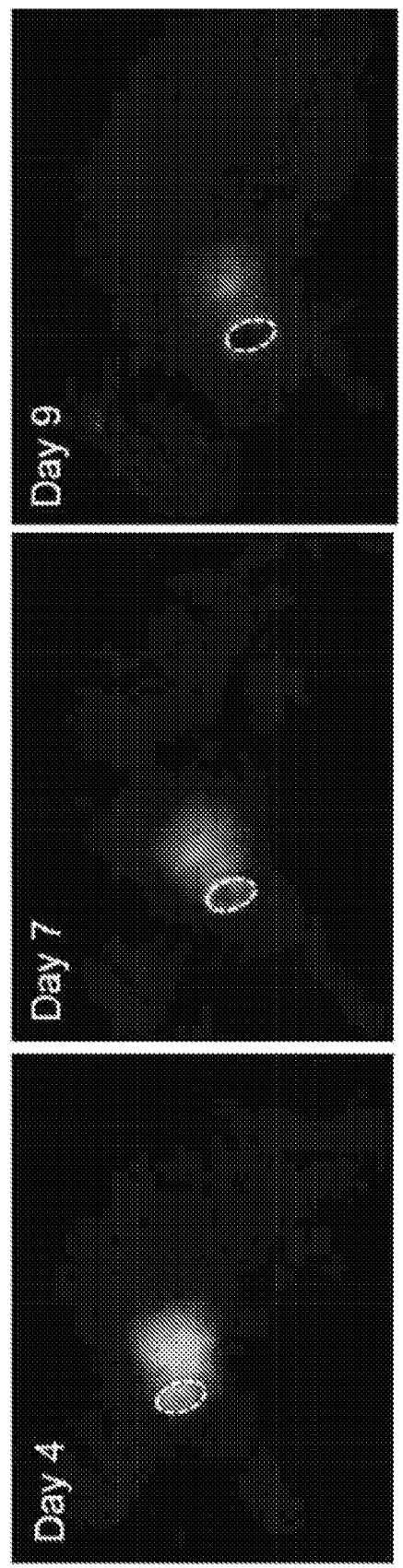
FIG. 22A  FIG. 22B  FIG. 22C
FIG. 22D  FIG. 22E  FIG. 22F

INTRALYMPHATIC CHEMOTHERAPY DRUG CARRIERS

CROSS-REFERENCE TO RELATED APPLICATIONS

The present invention claims the benefit of U.S. Provisional Application Ser. No. 61/024,837, filed Jan. 30, 2008, which application is incorporated herein by specific reference in its entirety.

This invention was made with government support under R21 CA132033 and P20 RR015563 awarded by the National Institute of Health. The government has certain rights in the invention.

BACKGROUND OF THE INVENTION

Cancer is a class of diseases in which a group of cells display uncontrolled growth and division beyond the normal limits, invasion into and destruction of adjacent tissues, and sometimes metastasis that spreads the cancer to other locations in the body via lymphatics or blood vessels. These malignant properties of cancers differentiate them from benign tumors, which are self-limited, do not invade or metastasize. Most cancers form a tumor but some, like leukemia, do not. Cancer may affect people at all ages, even fetuses, but the risk for most varieties increases with age. Cancer causes about 13% of all deaths. According to the American Cancer Society, 7.6 million people died from cancer in the U.S. during 2007. Cancers can affect all animals.

Nearly all cancers are caused by abnormalities in the genetic material of the transformed cells. These abnormalities may be due to the effects of carcinogens, such as tobacco smoke, radiation, chemicals, or infectious agents. Other cancer-promoting genetic abnormalities may be randomly acquired through errors in DNA replication, or are inherited, and thus present in all cells from birth. The heritability of cancers are usually affected by complex interactions between carcinogens and the host's genome.

Diagnosis usually requires the histological examination of a tissue biopsy specimen by a pathologist, although the initial indication of malignancy can be symptoms or radiographic imaging abnormalities. Most cancers can be treated and some cured, depending on the specific type, location, and stage. Once diagnosed, cancer is usually treated with a combination of surgery, chemotherapy, and radiotherapy. As research develops, treatments are becoming more specific for different varieties of cancer. There has been significant progress in the development of targeted therapy drugs that act specifically on detectable molecular abnormalities in certain tumors, and which minimize damage to normal cells. The prognosis of cancer patients is most influenced by the type of cancer, as well as the stage, or extent of the disease. In addition, histological grading and the presence of specific molecular markers can also be useful in establishing prognosis, as well as in determining individual treatments.

Cisplatin (i.e., cis-diamminedichloroplatinum or CDDP) has become an important chemotherapeutic agent for many solid tumors. However, newer platinum drugs have been found to have fewer side-effects, and such drugs may become important chemotherapeutic agents. One drawback to cisplatin as well as other chemotherapeutics or potential chemotherapeutics is significant toxicity.

Since organ toxicities hamper chemotherapy, oncologists have developed procedures to confine chemotherapy to the diseased areas by temporarily isolating the affected tissues or organs from the systemic circulation and perfusing them with the chemotherapeutic. For example, intra-arterial percutaneous pelvic perfusion of high-dose chemotherapeutic can provide a therapeutic advantage in advanced uterine cervical carcinoma with low side effects. However, these treatments are highly invasive and require specialized skills and equipment usually restricted to large medical research centers. In addition, tissue isolation is not possible in many cases, including locally advanced breast cancer that has significant invasion into lymphatic tissues.

Treatment of locally advanced breast cancer may be improved if chemotherapy were concentrated to the breast lymphatics, while maintaining adequate systemic levels for treatment of distant metastases. Neoadjuvant systemic chemotherapy is standard care for locally advanced breast cancer (LABC), but after treatment cancer typically spreads first via the lymphatics with little stroma invasion before becoming a systemic disease. Surgical treatment for early stage breast cancer involves resection of the primary tumor along with the draining sentinel lymph node and further lymphatic resection if warranted. However, this procedure may miss nanoscopic metastases in the lymph nodes if full immunohistochemical analysis is not routinely performed on sentinel node specimens, which is estimated to double the risk of relapse (compared to truly node negative cases). Localized radiation to the breast and lymphatics along with systemic chemotherapy reduce the risks of relapse, but these treatments cause extensive damage to healthy tissues.

Regardless of their origin, many cancers metastasize by using the lymphatic system (e.g. breast, ovarian, melanoma). The lymphatics are the body's drainage system, clearing waste from the tissues, and metastatic cancers follow this drainage to "seed" first in the local lymphatics. Surgery and chemotherapy can destroy many of these early metastases, but with great morbidity to the patient (e.g. toxicity side effects and painful lymphedema). Thus, it would be beneficial to have a chemotherapeutic that avoids these side effects by delivering chemotherapy directly to the tumor tissue in early cancers. Also, it would be advantageous for a chemotherapeutic to be preferentially directed into the lymphatics, and thereby avoiding side effects on normal cells elsewhere in the body, destroying the "seeds" that can cause recurrence after surgery and whole-body chemotherapy.

BRIEF SUMMARY OF THE INVENTION

In one embodiment, the present invention includes a chemotherapeutic composition configured for local administration by percutaneous injection. The composition can include a pharmaceutically acceptable carrier; and a nanoconjugate configured for preferential intralymphatic accumulation after percutaneous (where percutaneous refers to subcutaneous, intradermal, peritumoral, submucosal or transdermal) administration.

In one embodiment, the present invention includes a nanoconjugate comprising: a nanocarrier configured for preferential intralymphatic accumulation after percutaneous or interstitial administration; and a plurality of chemotherapeutic agents coupled to the nanocarrier. The nanoconjugate can have a dimension of about 10 nm to about 80 nm. Also, the nanoconjugate can be loaded with the chemotherapeutic agents from about 10% to about 50% w/w. The nanocarrier can be a hyaluronan polymer of about 20 kDa to about 150 kDa. Alternatively, the nanocarrier can be a dendrimer. The chemotherapeutic agents are selected from cisplatin, other platinum chemotherapeutic drugs, melphalan, withaferin A, mytomycin C, doxorubicin, epirubicin, docetaxel, daunorubicin, combinations thereof, and the like.

In one embodiment, the chemotherapeutic agents are coupled to the nanocarrier via a biodegradable linker. For example, the biodegradable linker is acid-labile or degradable.

In one embodiment, the chemotherapeutic composition and/or nanoconjugate is substantially devoid of PEG, HPMA, polyglutames, and/or silver.

In one embodiment, the chemotherapeutic agent is present in a therapeutically effective amount so as to provide a higher lymphatic AUC and a lower plasma $C_{max}$ compared to standard intravenous administration of the chemotherapeutic agent.

In one embodiment, the present invention includes a method for treating and/or inhibiting cancer. Such a method can include percutaneously administering a composition having a pharmaceutically acceptable carrier, and a nanoconjugate configured for preferential intralymphatic accumulation after subcutaneous administration. The nanoconjugate can be any embodiment as described herein.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1A is a graph that shows the tissue concentration of platinum in ipsilateral (right) axillary nodes and contralateral (left) axillary nodes after intravenous injection of cisplatin or subcutaneous injection of HA-Cisplatin (3.3 mg/kg cisplatin-basis) into the right mammary fatpad. FIG. 1B is a concentration vs. time pharmacokinetics graph that shows the plasma concentration of cisplatin after either intravenous injection of cisplatin (3.3 mg/kg) or subcutaneous injection of HA-cisplatin (3.3 mg/kg) in the right mammary fatpad.

FIG. 2A is a graph that shows the urine creatinine concentration of animals that received 3.3 mg/kg HA-cisplatin with or without silver. FIG. 2B is a graph that shows the urine creatinine concentration of animals that received 1.0 mg/kg HA-cisplatin with or without silver. In FIG. 2A, lower urine creatinine is a sign of renal damage as seen with the high dose samples containing silver, whereas in FIG. 2B, there was no significant difference between the two formulations at low doses.

FIG. 3A shows that animals receiving subcutaneous HA had normal tissues (control). FIG. 3B shows that animals receiving 3.3 mg/kg intravenous cisplatin had degenerative changes such as pyknotic nuclei in corticomedullary tubular cells. FIG. 3C shows that animals receiving subcutaneous 3.3 mg/kg HA-cisplatin without silver had fairly normal appearance except for minor foci of tubular cell necrosis at the corticomedullary junction. FIG. 3D shows that animals receiving 1.0 mg/kg subcutaneous HA-cisplatin with silver had widely spread pyknotic nuclei in medullary tubular epithelial cells. FIG. 3E shows that animals receiving 1.0 mg/kg intravenous cisplatin had pyknotic nuclei in medullary tubular epithelial cells, increases in dark purple staining suggesting nuclear staining and spread apoptosis. FIG. 3F shows that animals receiving 1.0 mg/kg subcutaneous HA-cisplatin had normal appearance except for minimal renal tubular cell swelling and degeneration.

FIG. 4A shows that animals receiving subcutaneous HA had normal tissue (control). FIG. 4B shows that animals receiving 3.3 mg/kg cisplatin had moderate necrosis. FIG. 4C shows that animals receiving 3.3 mg/kg subcutaneous HA-cisplatin had fairly normal appearance except for very mild degeneration. FIG. 4D shows that animals receiving 1.0 mg/kg HA-cisplatin with silver had fairly normal appearance except for very mild degeneration. FIG. 4E shows that animals receiving 1.0 mg/kg intravenous cisplatin had fairly normal appearance except for very mild degeneration. FIG. 4F shows that animals receiving 1.0 mg/kg subcutaneous HA-cisplatin had normal appearance.

FIGS. 5A-5F are images of brain tissue 30 days post single injection with drug and stained with H&E. Animals receiving subcutaneous injection of HA (control) and all study compounds (e.g., intravenous cisplatin 3.3 mg/kg, subcutaneous HA-cisplatin 3.3 mg/kg, subcutaneous HA-cisplatin with Ag 1 mg/kg, intravenous cisplatin 1 mg/kg, subcutaneous HA-cisplatin 1 mg/kg) had normal findings.

FIG. 8A is for the bladder. FIG. 8B is for the brain. FIG. 8C is for the heart. FIG. 8D is for the kidney. FIG. 8E is for the liver. FIG. 8F is for the lungs. FIG. 8G is for the muscle. FIG. 8H is for the spleen.

FIG. 10A shows the tissue concentration of cisplatin in right axilla lymph nodes (RLN) and left axilla lymph nodes (LLN) after subcutaneous injection of cisplatin or cisplatin-HA (3.3 mg/kg cisplatin basis) into right mammary fatpad. FIG. 10B shows the plasma concentration of cisplatin under the same procedure. Of note, serum Cmax for intravenous cisplatin is over 4 micrograms/mL whereas for HA-cisplatin it is less than 3 micrograms/mL. High Cmax with cisplatin has been directly linked with ototoxicity, nephrotoxicity and peripheral neuropathy associated with this drug. This data supports that HA-cisplatin may be less toxic than intravenous cisplatin.

FIG. 13A shows the breast lymphatic tumor 4 at the time that the mice were subcutaneously injected with Texas Red-HA 6 in the left mammary fat pad. After 5 hrs and 18 hrs (FIG. 13B and FIG. 13C, respectively), the photographs show that significant HA localized in the draining nodes and co-located with the tumor (GFP-channel in green in color and marked with 4, Texas Red channel in red and marked with 6, the blue arrow 2 is the injection site).

FIGS. 22A-22F are photographs showing the distribution of HA-doxorubicin after a single injection in the right mammary fat pad of a rat. Doxorubicin has innate fluorescence and the distribution and longevity of the drug-carrier conjugate can been well observed in this timed evaluation. Of note the bulk of drug-carrier is transported to the axillary lymph nodes where is slowly releases drug over a 9 day interval with still some residual activity even after 9 days. The oval marks the injection site in the breast and the darkest concentration (red) is in the axilla.

DETAILED DESCRIPTION OF THE PREFERRED EMBODIMENTS

Figure 1A:
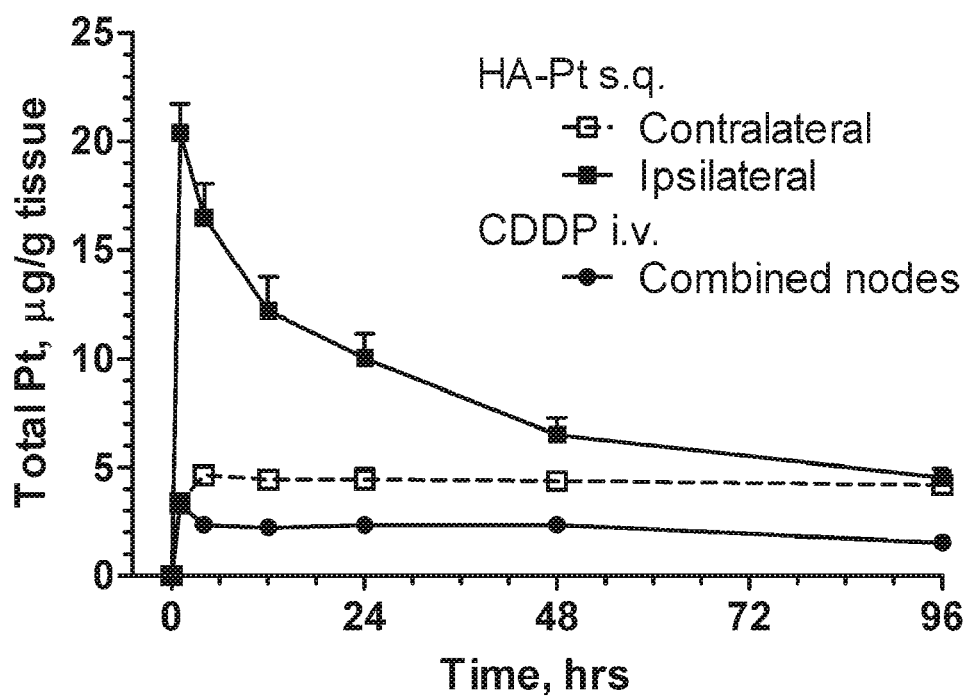
FIGS. 1A-1B include graphs that illustrate the tissue and plasma concentration of chemotherapeutic agents.

Generally, the present invention is related to new chemotherapeutic agents, pharmaceutical compositions having the chemotherapeutic agents, methods of making the chemotherapeutic agents, and methods of administering the chemotherapeutic agents in a manner for preferential accumulation in the lymphatic system. The chemotherapeutic agent includes a nanocarrier that is preferentially routed into the lymphatic system upon administration into substantially any interstitial site within a body, such as adjacent to a tumor or subcutaneously, but is not systemically administered. That is, the formulation is not administered via intravenous administration. As such, the chemotherapeutic agent preferentially targets any sized tumors, cancerous cells, or other malignancies within the lymphatic system. Such an approach can effectively inhibit the spread of cancerous cells from an initial cancer to another part of the body.

The design of the chemotherapeutic agent, which is a nanoconjugate, allows for translocation from the site of injection/administration through the lymphatic system so as to not produce elevated peak systemic concentrations that are toxic. Traditional administration routes, such as intravenous, produce high peak systemic concentrations usually via first-pass pharmacokinetics of the drug that are toxic and should be avoided. Therefore, the chemotherapeutic agent preferentially translocates into the lymphatic system, and can treat cancerous cells that are in the lymphatic system, which include cells that may be residing in a lymph node. This mode of translocation follows the route many cancerous cells follow when initially spreading from their primary focus, and thereby can be used to treat or inhibit the spread of cancerous cells through the locoregional tissues.

The chemotherapeutic agent includes a nanocarrier that is optimized in size and composition to preferentially be translocated into the lymphatic system rather than spread and concentrate systemically. It has been found that hyaluronan polymeric carriers and some dendritic carriers, such as those described herein, have such as selective translocation characteristic into the lymphatic system. For example, the chemotherapeutic agent can be deposited adjacent to a skin cancer and enter the lymphatic system similar to the cancerous cells.

Cisplatin is one of the most widely used chemotherapy agents for solid tumors; however, its toxicity and resistance severely limits its dose and use in many patients. Penetration of systemic cisplatin into the lymphatics may be poor (less than 1-5% of drug injected), and alternatives treatments for localized cancers (e.g., surgical removal or radiation) can lead to serious side effects such as infections and lymphedema. As such, a method of treating or inhibiting the accumulation of cancerous cells in the lymphatics is desirable, and can now be accomplished through the subcutaneous or interstitial administration of a nanoconjugate that preferentially translocates to the loco-regional tissues and lymphatics. The nanoconjugate can include a nanocarrier of a FDA-approved biocompatible carrier coupled to a chemotherapeutic drug (e.g., cisplatin). The nanoconjugate can also decrease systemic toxicities compared to traditional intravenous therapy with cisplatin. This allows for the treatment, inhibition, and/or prevention of many cisplatin responsive cancers, such as breast, non-small cell lung, ovarian, and head and neck squamous cell carcinoma and other cisplatin-sensitive tumors, as the lymphatics are involved in early to late stages of the spread of the disease. Cisplatin is also referred to herein as CDDP and Pt, such as in the examples and figures.

Previously, targeting and nanocarrier strategies have been reported to increase the dosage of cisplatin reaching tumor-bearing tissues, while sparing normal tissues from toxic doses. These technologies can be categorized into untargeted or passively targeted carriers (e.g., non-receptor) and actively targeted carriers (e.g., antibodies). Among the untargeted carriers such as polymeric micelles formulations (e.g., NC-6004) have demonstrated reduced nonspecific toxicities in preclinical studies and have progressed to early clinical trials. In phase I trials, an untargeted linear polymer conjugate of N-(2-hydroxypropyl)methacrylamide (HMPA) and platinum (e.g., AP5280) had demonstrated higher sustained plasma levels of platinum in humans with minimum toxicity compared to intravenous cisplatin. These untargeted carriers rely on the enhanced permeability and retention effect (EPR) to improve tumor accumulation of the drug, but in tumors that are not highly vascularized, the EPR effect is greatly reduced and untargeted nanocarriers have less advantages. Accordingly, passive targeting is not effective in the treatment of tumors with low vascularity, such cancerous cells that can be found in the lymphatic system.

Now, with the present invention cancerous cells that are not vascularized, such as those found within the lymphatic system, can be treated or inhibited by selectively accumulating a chemotherapeutic agent in the loco-regional lymphatics of the tumor via a subcutaneous injection at the site of the tumor, allowing the chemotherapeutic drug to be delivered along the lymphatic pathway where tumors are most likely to initially metastasize. This can be performed with a nanoconjugate of a biocompatible nanocarrier and a chemotherapeutic drug, where the nanocarrier provides for site selective accumulation of a drug that is difficult to deliver without a carrier.

The subcutaneous administration of a nanoconjugate that can accumulate in intralymphatic tissues is beneficial for treating many cancers, such as breast cancers. For example, breast cancers typically spread to regional lymph nodes once they disseminate from the primary tumor, thus adequate evaluation and treatment of the axillary lymph nodes is important in early stage disease. One significant problem with current therapy is the side effects chemotherapy agents create systemically either alone or in combination. The nanoconjugates of the present invention are advantageous because they, surprisingly and unexpectedly, can accumulate in the cancerous cells that are present in the lymphatic system and/or intralymphatic tissues and thereby act on lymphatic metastases without undesirable systemic toxicities. The nanoconjugates can be subcutaneously administered for accumulation in intralymphatic tissue. As such, the nanoconjugates can be used to treat breast cancer to preferentially treat at-risk regional lymph nodes and avoid systemic toxicities.

The present invention can include a nanoconjugate of the polysaccharide hyaluronan (HA) with a chemotherapeutic drug (e.g., cisplatin or other platinum), pharmaceutical compositions and methods related to the same, especially those related to subcutaneous injection for achieving therapeutic intralymphatic localization and non-toxic systemic concentrations. The HA nanoconjugate is formulated with a molecular weight/size of HA that is effective in concentrating cisplatin to the breast lymphatics, and reduce peak plasma concentrations that are toxic. While cisplatin has been used herein as a representative chemotherapeutic drug, other drugs that are shown to be effective in chemotherapy can be conjugated to the nanoconjugates of the present invention. Also, HA is used as a representative nanocarrier; however, other nanocarriers with the same or similar physiological delivery profiles and properties, such as dendrimers, can be used. Cisplatin was used and described herein because of the ease of determining platinum deposition in organs, tissues, and lymphatics by atomic absorption spectroscopy. As such, cisplatin deposition after administration is representative of other chemotherapeutic drugs that can be conjugated to the nanocarrier.

In one embodiment, the chemotherapeutic drug is cisplatin, which has been shown to be an excellent anticancer agent for many solid tumors, but the standard formulation of cisplatin has been shown to have significant systemic toxicity. Now, the nanoconjugate of cisplatin has been shown to capable of being administered subcutaneously as a loco-regional delivery system to increase platinum levels in the lymphatics, where early metastasis is most likely to occur, while reducing systemic toxicities.

The cisplatin nanoconjugate surprisingly and unexpectedly, also can provide suitable systemic concentrations that are therapeutically effective without significant systemic toxicity. As demonstrated in the figures in this application, HA-cisplatin is able to provide serum and systemic AUCs which are therapeutically effective but without the toxic high Cmax levels of standard intravenous CDDP. The combination of being capable of being delivered locally via subcutaneous administration (e.g., proximal the tumor) for therapeutically effective intralymphatic accumulation and systemic concentrations and having less toxic sustained release characteristics make it more advantageous than standard CDDP.

For example, cisplatin can be conjugated to a biocompatible polymer such as hyaluronan, with a conjugation degree of approximately 20 w/w %. The nanoconjugates can be delivered via subcutaneous injection (e.g., into the breast tissue of rats) for therapeutically effective intralymphatic accumulation and systemic concentrations. The HA-cisplatin nanoconjugate demonstrated antiproliferative efficacy similar to standard cisplatin formulations in human breast cancer in vitro. The nanoconjugate increased the plasma area-under-the-curve (AUC) by 2.7-fold compared to normal cisplatin, but with a reduced peak plasma level (Cmax) which is beneficial for reducing systemic toxicity. The nanoconjugate increased the ipsilateral lymph node AUC by 3.8-fold compared to cisplatin. Pathology studies of animals receiving the nanoconjugate treatment showed normal appearance of brain and lymph nodes, with less necrosis and inflammation in the kidneys and liver compared to intravenous administered cisplatin. Thus, the nanoconjugate demonstrates that intralymphatic drug delivery with hyaluronan-based chemotherapeutic drugs may allow lower drug dosing levels with less toxicity than intravenous therapies while providing a "boost" dose of the chemotherapeutic drug in the loco-regional tissue basin where tumor burden is highest.

Generally, the nanocarrier may be conjugated to peptides, antibodies (both monoclonal and polyclonal), interferon, other nitrogen mustard class drugs besides melphalan including chlorambucil, amiodarone, topotecan, withaferin A, HSP90 inhibitors including 17-AAG, VEGF inhibitors, histone deacetylase inhibitors, and any of the taxanes including taxol, paclitaxel, docetaxel and the like. Some examples of drugs that can be conjugated to the nanoconjugate include cisplatin, other platinum drugs, melphalan, mytomycin C, doxorubicin, epirubicin, docetaxel, daunorubicin, chlorambucil, 5FU, paclitaxel, vincristine, Her2 antibodies and peptides, EGFR antibodies and peptides, rapamycin, mTOR inhibitors, withaferin A, HDAC inhibitors, SAHA, Hsp90 inhibitors, 17-AAG, and 17-DMAG.

In one embodiment, the nanocarrier is a hyaluronan (HA) polymer, which is a highly biocompatible polymer that has now been found to follow lymphatic drainage from the interstitial spaces, such as from subcutaneous administration. The nanoconjugates of HA and cisplatin can be formed by non-covalent conjugation or through biodegradable bonds, such as ester or hydrazine bonds. The nanoconjugates can be injected subcutaneously anywhere in the body. Examples include injection into the upper mammary fat pad of female subjects for treatment of breast cancer.

Hyaluronan (HA) polymer is a polysaccharide, of alternating D-glucuronic acid and N-acetyl D-glucosamine, found in the connective tissues of the body and cleared primarily by the lymphatic system (12 to 72 hrs turnover half-life). After entering the lymphatic vessel, HA is transported to lymph nodes where it is catabolized by receptor-mediated endocytosis and lysosomal degradation. Several studies have correlated increased HA synthesis and uptake with cancer progression and metastatic potential. Breast cancer cells are known to have greater uptake of HA than normal tissues, requiring HA for high P-glycoprotein expression, the primary contributor to multi-drug resistance. Furthermore, invasive breast cancer cells overexpress CD44, the primary receptor for HA, and are dependent on high concentrations of CD44-internalized HA for proliferation. Thus, chemotherapeutic drug nanoconjugates with HA may be efficacious against lymphatic metastases.

Accordingly, HA-drug nanoconjugates can be directed to the lymphatic system and accumulate in lymph nodes by binding to CD-44 receptors on the lymph node surface and cancer cells where the CD-44 receptors are overexpressed. Hyaluronan is also a ligand for CD44 receptor and is cleared primarily by the lymphatic system where it is catabolized in the nodes by CD44 receptor-mediated endocytosis followed by lysosomal degradation. This allows the drug in the nanoconjugate to be delivered to the site of initial tumor spread, concentrating its effects in the lymph nodes. By having lymphatic uptake as opposed to systemic absorption, the HA nanoconjugates provide for lower organ and systemic toxicity compared to current chemotherapy delivery technologies with naked drugs.

The molecular weight of the HA can be varied, but has a significant effect on uptake into the lymph system and thereby affects the lymphatic drug concentration. It has been found that hyaluronan has superior performance at 35 kDa, but can also be used at 75 and 150 kDa for administration. Due to inflammatory responses, less than 10 kDa would may be feasible, and due to high viscosity more than 700 kDa may not be practical.

Accordingly, the molecular weight of HA can be optimized to about 20 kDa to about 150 kDa, more preferably from about 25 kDa to about 100 kDa, and most preferably from about 30 kDa to about 75 kDa. These lower molecular weight HA polymers can be further refined depending on the drug being loaded and the accumulation characteristics of the nanoconjugate in the lymphatic system. For example, molecular weights of 30 kDA to 50 kDa can be advantageous as well as about 35 kDa polymers. These HA polymers are sufficiently soluble so as to be capable of transporting the drug conjugated thereto into the lymphatic system.

Also, the nanocarrier can be a dendrimer. The dendrimer generation can be selected to optimize the ratio of lymphatic to capillary uptake. Dendrimer nanoparticles have extremely well-defined size and surface charge depending on the generation of material and the termini group chemistry. An example includes PAMAM dendrimers (polyamidoamine), phosphoester dendrimers, bis(3-hydroxypropyl) phosphonate dendrimers, Carboxy ester dendrimers, amino acid dendrimers, hyperbranched polymers (e.g. branched polyamino acids, branched polyesters, branched polyphosphoesters), polysaccharides (hyaluronan, dextran and its sulfonated derivatives, cellulose), and the like.

The nanoconjugate can be formulated for peritumor and subcutaneous injection for preferential translocation into the lymphatic system so systemic exposure is limited. The nanoconjugate can be from about 10 to about 30 nm to avoid capillary uptake with a neutral or negative charge to maximize rapid lymphatic uptake, preferentially about 15 to 25 nm, and most preferentially about 20 nm. There is an optimum size range for lymphatic uptake of subcutaneously injected particles: particles larger than 100 nm will remain largely confined to the site of injection, particles 10-80 nm are taken up by the lymphatics, and small particles and molecules (<20 kDa) will be absorbed by the blood capillary network into systemic circulation. Nanoconjugates larger than 100 nm or less than 5 nm are not very practical. Preferably, the nanoconjugates can be between 10 and 80 nm, more preferably between 15 and 50, and most preferably between 20 and 40 nm.

Previous reports have demonstrated the ability of HA to form stable conjugates with platinum drugs; however, the nanoconjugates of the present invention have different characteristics, such as molecular weight of HA, drug loading, and formulations configured for subcutaneous administrations. Never before have HA-drug conjugates been designed and formulated for subcutaneous administration for lymphatic deposition and retention as well as for suitable systemic concentrations. Furthermore, subcutaneous HA nanoconjugates have now been found to be drained to the axilla basin of rats after subcutaneous injection into the mammary fatpad. Thus, the compositions can be configured for direct injection into a tumor and/or subcutaneous injection for accumulation in the lymph system to treat metastasizes that may be found in the lymph system, such as in lymph nodes.

For example, subcutaneously injected cisplatin-HA nanoconjugates contained up to 0.25 w/w of cisplatin and released drug with a half-life of 10 hours in saline. Cisplatin-HA nanoconjugates had high anti-tumor activity in vitro similar to free cisplatin: cisplatin-HA $IC_{50}$ 7 μg/mL in MCF7 and MDA-MB-231 human breast cancer cells (free cisplatin $IC_{50}$ 7 μg/mL). Cisplatin-HA conjugates were well tolerated in rodents with no signs of injection site morbidity or major organ toxicity after 96 hours. The AUC of cisplatin in the axially lymph nodes after injection with cisplatin-HA increased 74% compared to normal cisplatin.

The systemic concentration of the chemotherapeutic drug delivered by the nanoconjugates can achieve a high enough level to be effective in treating any metastasized or systemic cancerous cells with a low enough level to be substantially non-toxic. Previously, the inclusion of naked platinum drugs in chemotherapeutic regimens has been associated with several toxicities including increased risk of leukopenia, nausea, hair loss, acute nephrotoxicity, chronic neurotoxicity, and anemia. As such, a loco-regional therapy approach for cancers confined to the breast and axilla may greatly improve the use of platinum drugs in breast cancer chemotherapy. For this purpose, hyaluronan may be an ideal carrier for localizing cisplatin to the lymph nodes.

In one embodiment, the nanocarrier is conjugated to the chemotherapeutic drug via a biodegradable linker. That is, the linker can be configure to degrade so as to release the chemotherapeutic proximal or within cancer cells. In the case of HA, the linker can be an acid-degradable linker. An acid-degradable linker can be utilized with HA because of the ability of HA to be internalized into a cell and translocated to a lysosome, which acidifies and degrades such a linker. Also, the hypoxic microenvironments around cancerous cells can degrade these linkers. This releases the drug directly into the cancerous cells that internalize the HA nanoconjugate.

Examples of acid-degradable linkers include hydrazone, esters, ketals, biodegradable polymer linkers, polylactide, polyglycolide, copolymers thereof, combinations thereof, and the like. In addition to acid degradable disulfides, 1,6 elimination linkers, phosphoester linkers, enzymatically cleavable linkers including but not limited to short peptide sequences recognized by enzymes found in tumors and surrounding tissues, lymphatics, and lymph nodes, which may be expressed at a higher level in these tissues than in most non-target tissues.

In one embodiment, the nanoconjugate is not pegylated. As such, the nanoconjugate can be substantially devoid of a PEG. Also, the nanoconjugate can be devoid of HPMA or polyglutames. The nanoconjugates can be formulated without being encapsulated.

The ability to subcutaneously administer the nanoconjugates and provide localized chemotherapy in the lymph system allows for the treatment of various cancers. More particularly, it allows for the treatment of early stage cancers that have begun to translocate through the lymph system. Thus, this administration route and accumulation in the lymph system allows the nanoconjugates to provide localized therapy to a variety of cancers, such as breast cancer, colon cancer, lung cancer, non-small cell lung, melanoma, head and neck cancers (e.g., head and neck squamous cell carcinoma), ovarian cancer, and lymphoma as well as others.

Direct injection into rat breast tissue of cisplatin with a silver-activated nanoconjugate of cisplatin was studied even though local injection of cisplatin is not feasible due to tissue damage. Additionally, tumor studies showed the silver activated nanoconjugate to cause premature animal death. As such, the nanoconjugate of the present invention was developed and it does not require the use of silver (i.e., the nanocarrier is not silver activated), and thereby the nanoconjugate of the present invention does not have the toxic side effects associated with silver. The localized chemotherapy with silver-free nanoconjugate chemotherapeutics (e.g., HA-cisplatin nanoconjugates) after subcutaneous administration was compared to standard intravenous administered cisplatin with respect to the major organ pathologies in response to the different treatments. Subcutaneous administration of the nanoconjugates provided localized nanoconjugate chemotherapy with significantly increased lymphatic tissue concentrations over systemic therapy and reduced organ toxicities including nephrotoxicity in rats.

Previously, hyaluronan was activated with silver nitrate prior to conjugation with cisplatin, as this has been reported to improve conjugation efficiency. However, it has now been found that it is extremely difficult to remove all traces of silver from the resulting conjugates, even after multiple rounds of extended dialysis against water. The presence of silver in the treatments resulted in a significant number of animals succumbing to silver-induced toxicity as determined by pathological examination. This is unacceptable in human treatment, and led to an alteration of the formulation schema to eliminate silver from the conjugation procedure. The coupling reaction was then re-engineered without silver activation in order to obtain the highest conjugation efficiency, which ultimately did not impair formation of the HA-platinum conjugates. This is a significant advancement in terms of clinical development as cisplatin and HA are both approved by the FDA for use in humans and no additional substances are required for formation of the complex. The resulting nanoconjugates still had excellent antiproliferation activity against multiple breast cancer lines in vitro, indicating the change in formulation method does not affect cell-based drug efficacy.

The pharmacokinetics and tissue distribution for the nanoconjugate indicated lymphatic delivery of the HA-cisplatin nanoconjugate improved drug levels in the local lymph basin compared to intravenous cisplatin dosing. At an equivalent dose of platinum, the HA-cisplatin carrier greatly increased lymph node basin concentrations, suggesting the carrier is able to deliver platinum to the lymph nodes through the lymphatics much more effectively than intravenous drug administration routes. In addition, the HA-cisplatin nanoconjugate appeared to maintain its stability in vivo long enough to traffic or localize into the lymphatics before releasing its conjugated drug.

The nanoconjugate preferential accumulation in the lymphatic system reduces systemic tissue exposure to platinum compared to intravenously delivered cisplatin, but the HA-cisplatin nanoconjugate due to its sustained release properties (e.g., selective translocation and selective degradation of the linker) actually increased platinum AUC an average of 200% in most tissues compared to intravenous cisplatin. This, is likely due to the accumulation of platinum (from the HA-cisplatin delivered subcutaneous) over time from a more sustained release profile compared to rapid decay and elimination via an intravenous bolus infusion. This increased tissue level also carries two advantages: (1) a lower dose of platinum being required to achieve the same tissue effect such that the HA-cisplatin dose may be reduced 50% and still maintain equivalent tissue levels; and (2) maintaining therapeutic systemic levels of drug is important for utilizing this drug as an adjuvant therapy since it is well known that most patients with breast cancers which have metastasized to the loco-regional lymph nodes have likely micro if not macrometastases systemically. Therefore, this treatment can be use in place of daily systemic intravenous therapy by now utilizing a less invasive and less-frequent dosing schedule, e.g. weekly subcutaneous dosing as compared to current therapy which is daily intravenous infusion, while simultaneously providing a local "boost" of drug delivery to the loco-regional tumor basin and lymphatics. The larger AUC of HA-cisplatin can also increase rates of tumor apoptosis since prolonged sub-toxic levels of cisplatin can substantial improve tumor cell apoptosis compared to a single high dose.

Since the more severe side effects of cisplatin are likely due to the high peak plasma levels ($C_{max}$) experienced immediately after intravenous administration, recent applications included metronomic dosing regimens have been shown to decrease toxicity although they increase inconvenience and costs to patients. As such, locally administered nanoconjugates prevent high peak levels both due to slow release of drug from the carriers, with a half-life in saline of around 10 hours compared to under an hour for the standard intravenous cisplatin formulation, and after its release from the carrier, the cisplatin takes time to diffuse from the tissues or lymph into the systemic circulation. Subcutaneous HA-cisplatin has a much lower peak plasma concentration compared to intravenous cisplatin (FIG. 1A-1B), although the overall plasma platinum AUC is much greater than with intravenous cisplatin. After subcutaneous HA-cisplatin injection, there was a 2 hr delay before plasma platinum peaked and plateaued-off, then remaining at a constant level. This release profile is consistent with a delayed and sustained release from the lymphoid tissues.

Figure 2A:
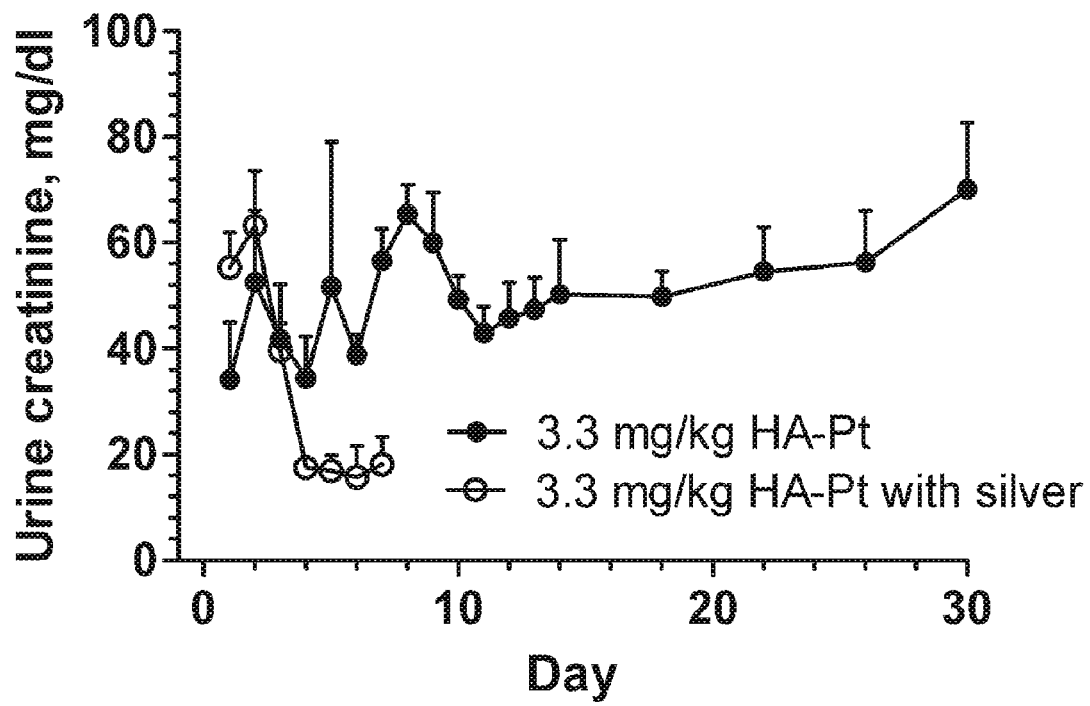
FIGS. 2A-2B include graphs that illustrate the concentration of creatinine in urine over time after a single dose administration of subcutaneous HA-cisplatin in the right mammary fatpad.
Figure 2B:
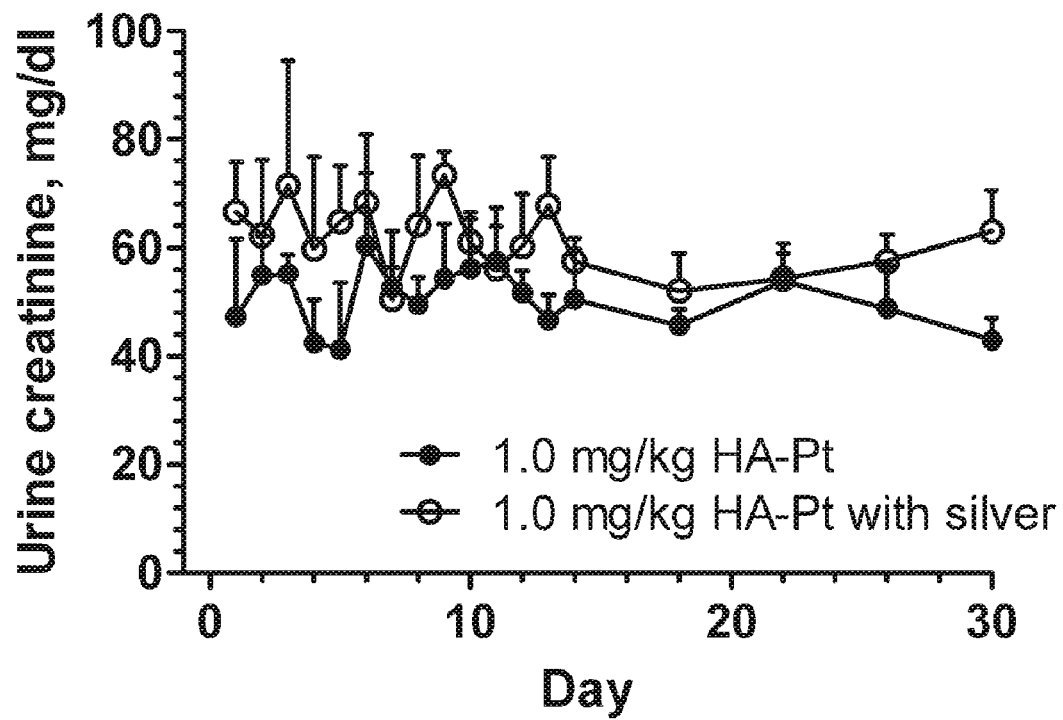
Figure 3A:
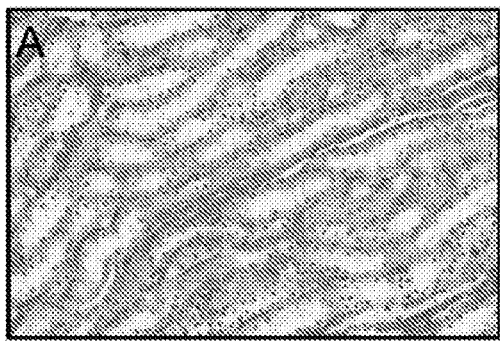
FIGS. 3A-3F are images of kidney tissue 30 days post single injection with drug compound and stained with hematoxylin and eosin.
Figure 3B:
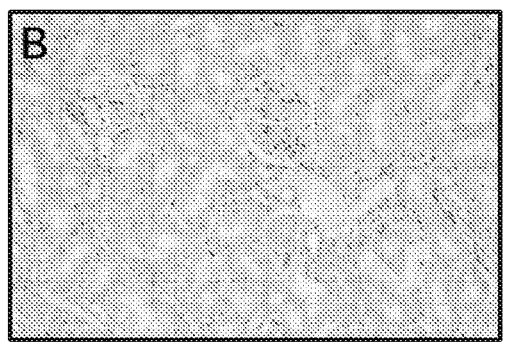
Figure 3C:
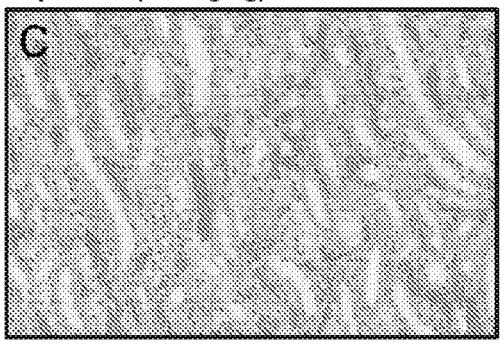
Figure 3D:
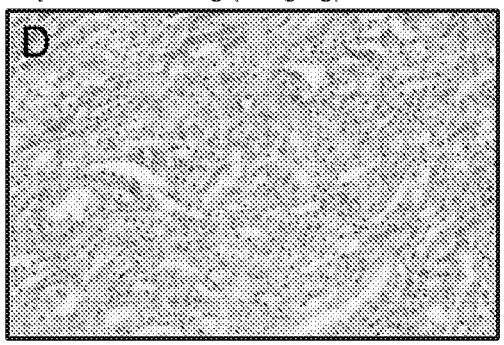
Figure 3E:
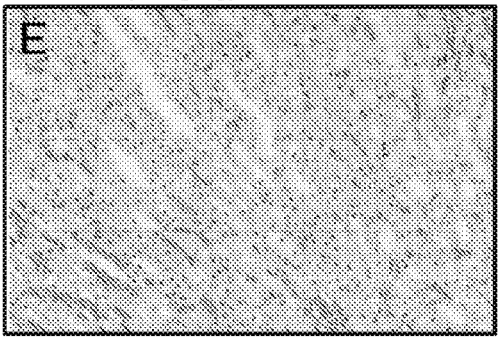
Figure 3F:
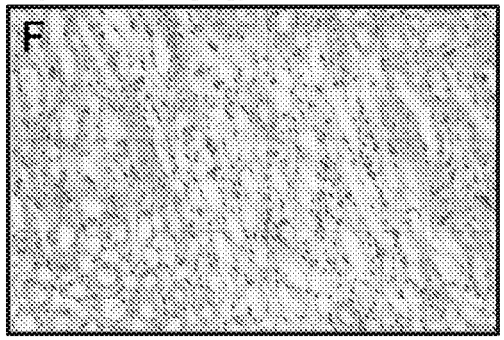
Figure 4A:
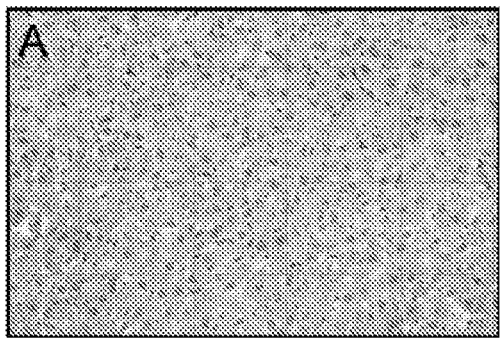
FIGS. 4A-4F are images of liver tissue 30 days post single injection with drug and stained with H&E.
Figure 4B:
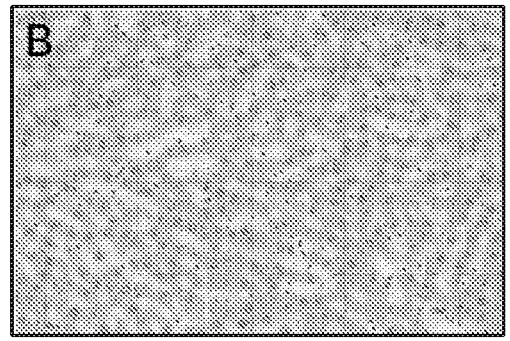
Figure 4C:
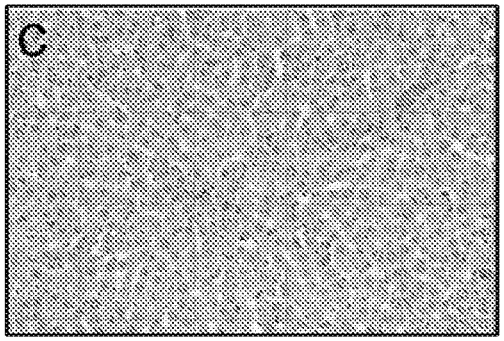
Figure 4D:
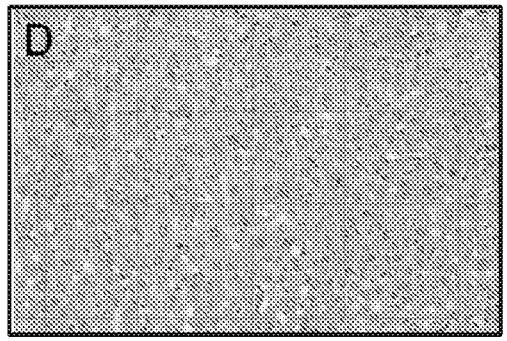
Figure 4E:
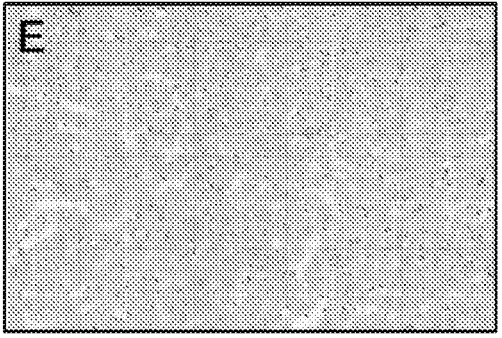
Figure 4F:
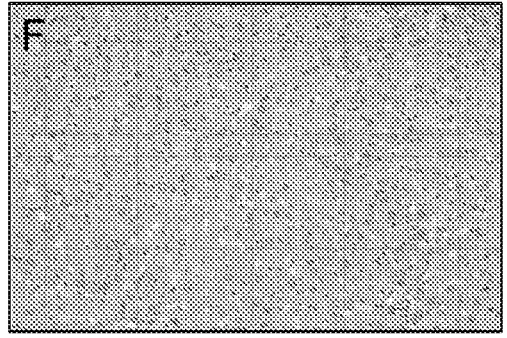
Figure 6A:
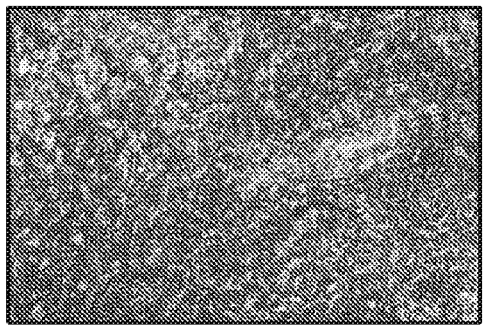
FIGS. 6A-6F are images of lymphoid tissue 30 days post injection and stained with H&E. Animals receiving subcutaneous injection of HA (control) and all study compounds (e.g., intravenous cisplatin 3.3 mg/kg, subcutaneous HA-cisplatin 3.3 mg/kg, subcutaneous HA-cisplatin with Ag 1 mg/kg, intravenous cisplatin 1 mg/kg, subcutaneous HA-cisplatin 1 mg/kg) had normal findings.
Figure 6B:
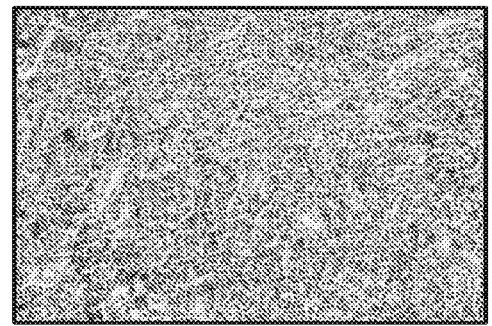
Figure 6C:
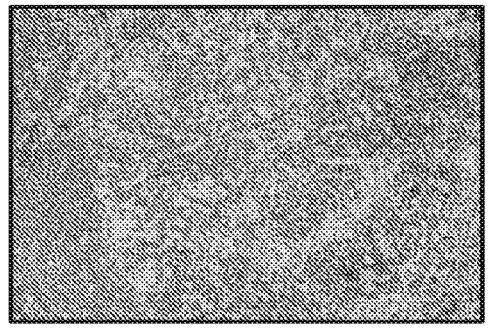
Figure 6D:
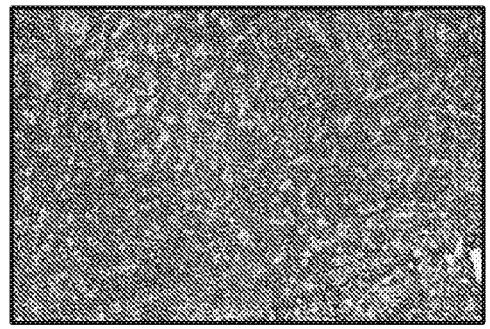
Figure 6E:
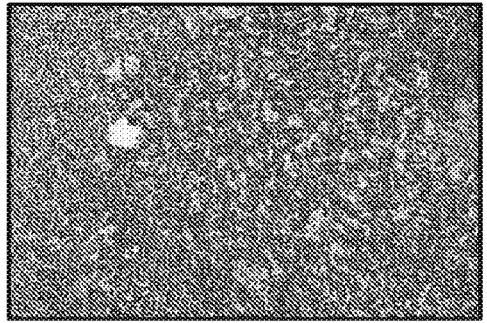
Figure 6F:
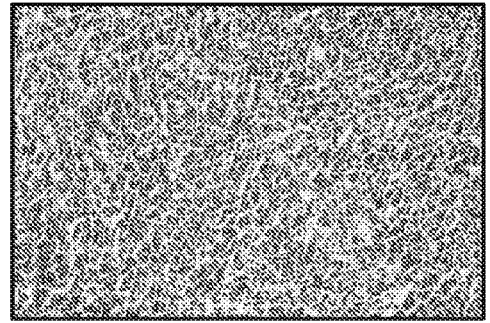
Figure 7A:
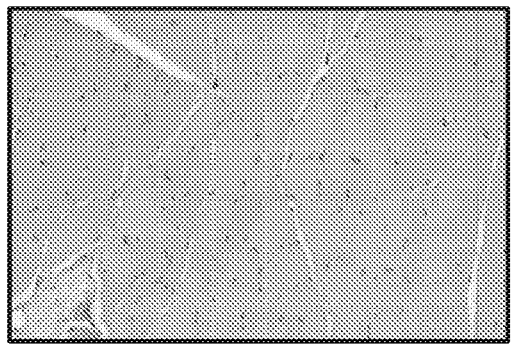
FIGS. 7A-7D are images of the underlying tissue at injection site 30 days post injection. Animals receiving subcutaneous injection of HA (control) and all study compounds (e.g., subcutaneous HA-cisplatin 3.3 mg/kg, subcutaneous HA-cisplatin with Ag 1 mg/kg, HA-cisplatin 1 mg/kg) had normal findings.
Figure 7B:
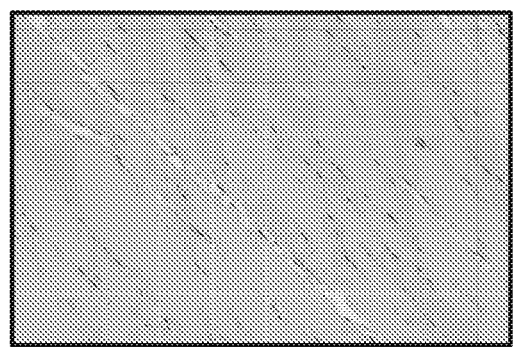
Figure 7C:
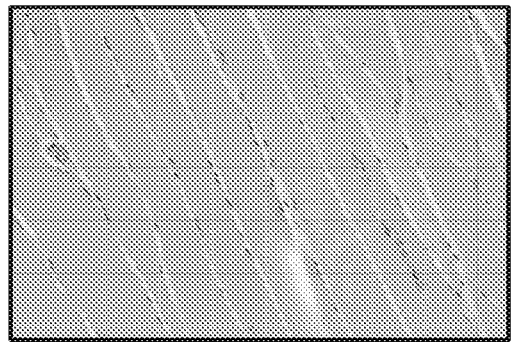
Figure 7D:
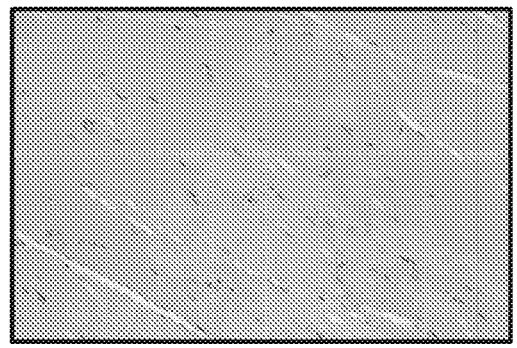
Figure 8A:
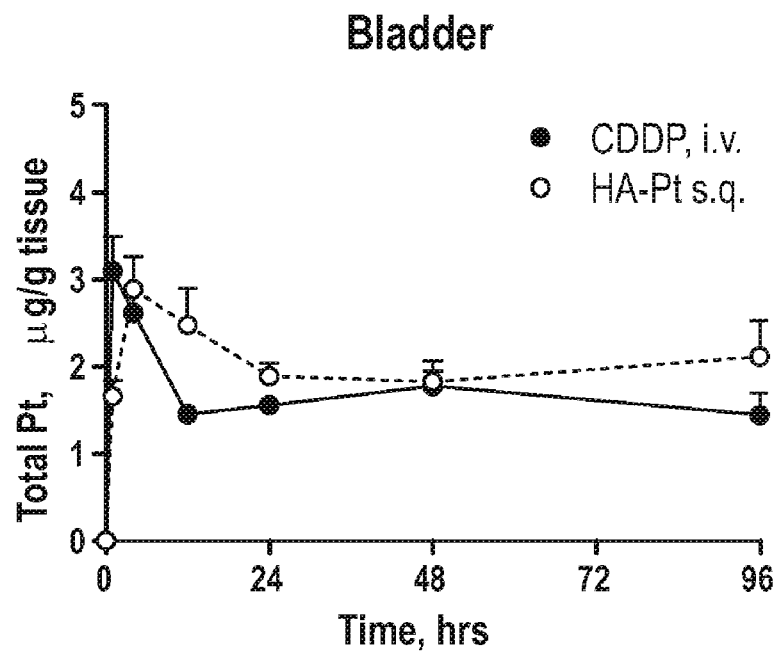
FIGS. 8A-8H are graphs illustrating tissue concentrations of platinum after intravenous injection of cisplatin (3.3 mg/kg cisplatin basis) or subcutaneous injection of HA-cisplatin (3.3 mg/kg cisplatin basis) into right mammary fatpad.
Figure 8B:
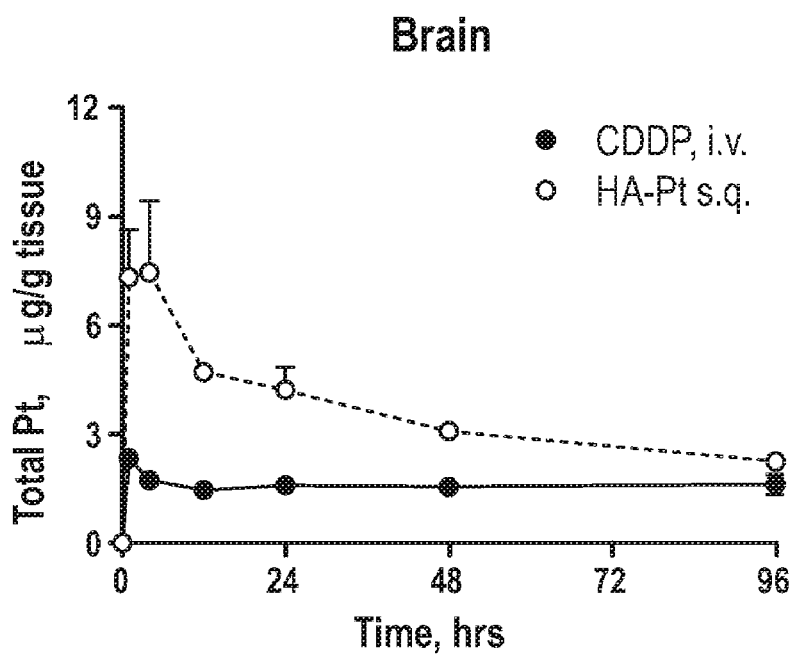
Figure 8C:
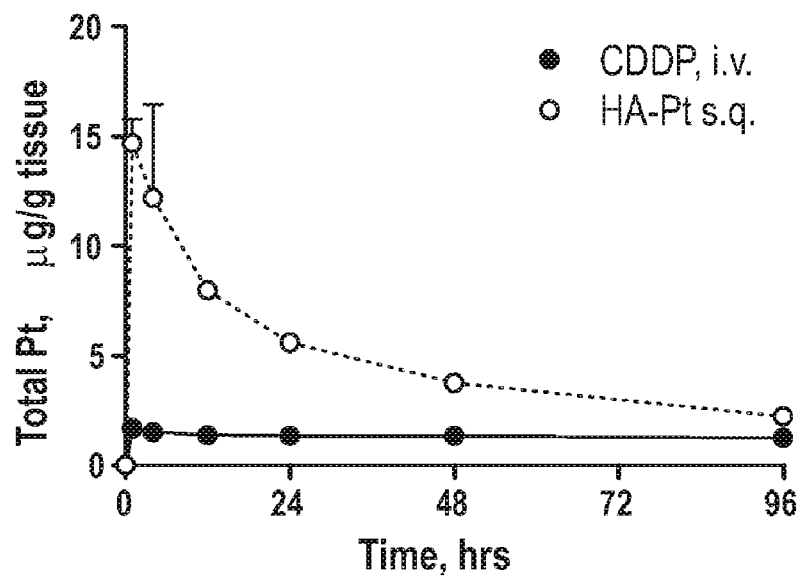
Figure 8D:
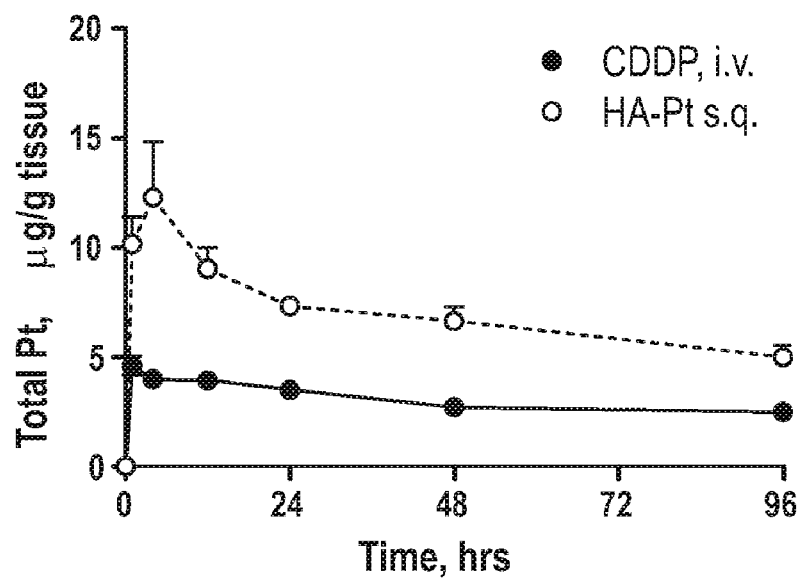
Figure 8E:
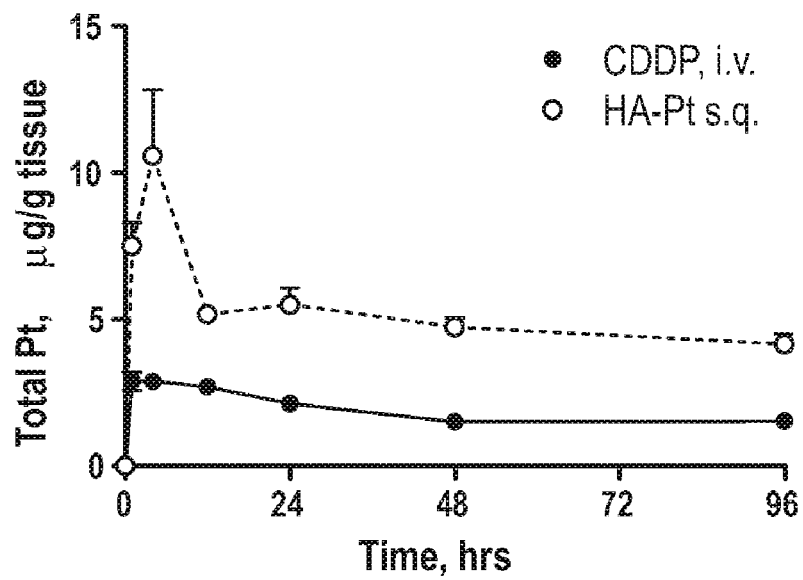
Figure 8F:
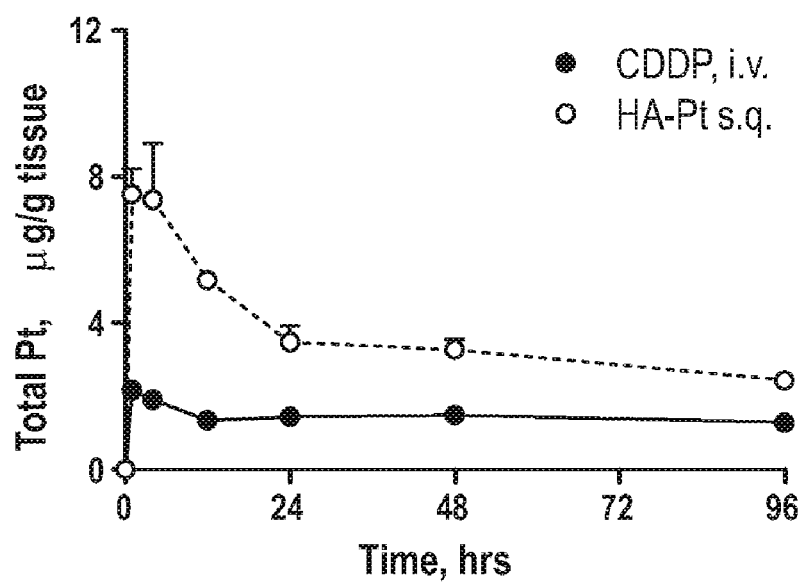
Figure 8G:
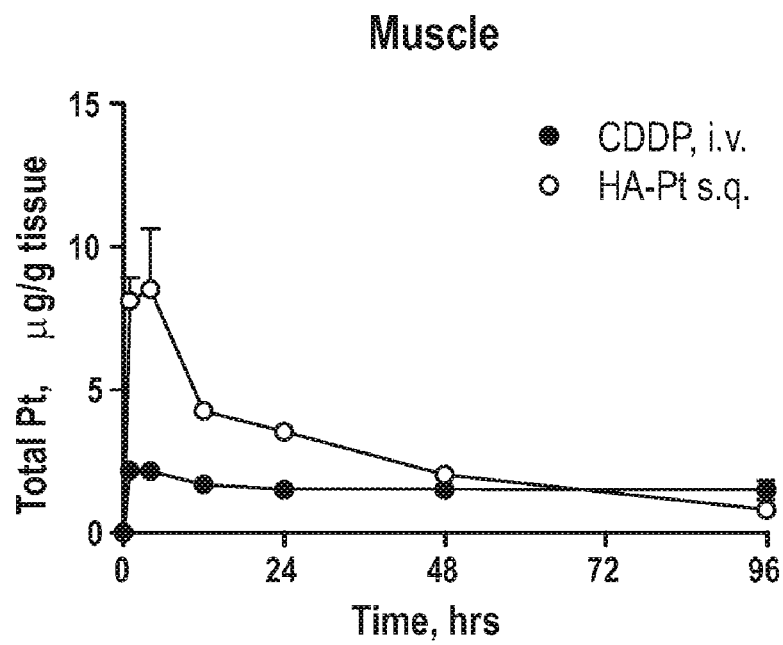
Figure 8H:
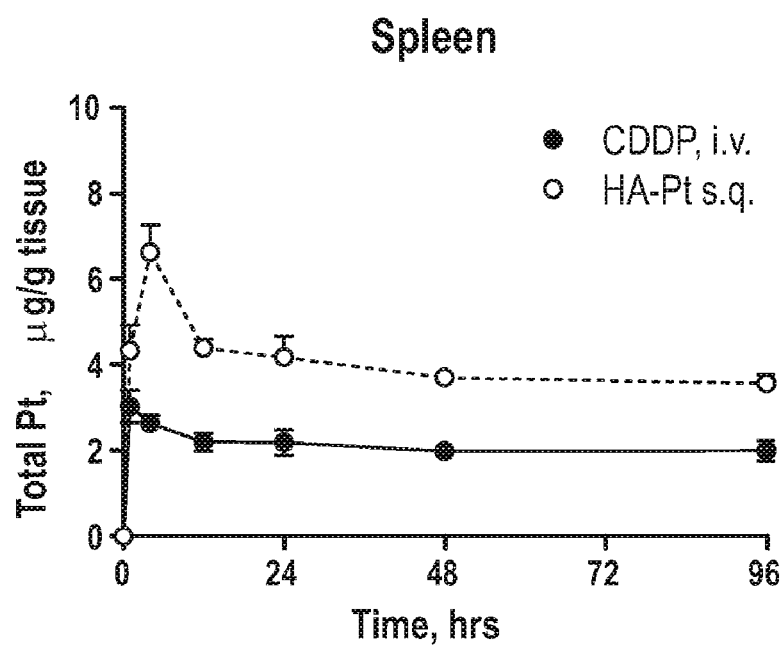

FIGS. 2A-2B show that creatinine levels did not indicate significant differences in renal toxicity between intravenous cisplatin and localized nanoconjugates despite the much higher AUC of nanoconjugate platinum. The high dose silver formulation caused decreased urine creatinine levels and animal death within the first week, which is unfavorable. The severe in vivo toxicity of silver formulations indicates that the slightly greater in vitro anti-proliferative activity of silver formulations (Table 1) may be due to non-specific silver toxicity. Although no damage was detected, creatinine testing may not be sensitive enough to detect minor renal damage after a single moderate dose, so we conducted pathological examinations for more direct evidence of platinum toxicity. Thus, in one embodiment, a nanoconjugate formulation is substantially devoid of silver.

Pathological examination 30-days following a single dose injection of cisplatin revealed there were significant renal and hepatic differences between the subcutaneous HA-cisplatin and intravenous cisplatin formulations. Although the renal platinum AUC of HA-cisplatin was twice that of cisplatin, the lower incidence and less severe nature of renal cell necrosis in the HA-cisplatin treated animals indicated improved tolerability over intravenous cisplatin. The greater platinum AUC of HA-cisplatin in the kidneys would seem to contradict the lower toxicity observed, but may be due to its lower peak serum drug levels ($C_{max}$) filtered by the kidney compared to intravenous cisplatin.

Liver pathology indicated decreased toxicity of the HA-cisplatin compared to cisplatin, and none of the animals had normal pathology in the 3.3 mg/kg cisplatin arm. Cisplatin-induced hepatotoxicity is known to occur due to the production of reactive oxygen species. Hyaluronan is metabolized in the liver and glycosaminoglycans are known antioxidants with hepato-protective effects, so the HA nanoconjugate may protect against platinum hepatotoxicity.

Accordingly, an embodiment includes a nanoconjugate of HA and cisplatin that concentrates cisplatin in the breast lymphatics after subcutaneous injection into the mammary fatpad. These nanoconjugates have sustained release characteristics resulting in a higher lymphatic AUC and lower plasma $C_{max}$ compared to standard intravenous cisplatin. The nanoconjugates do not cause substantial organ toxicities, such as renal, hepatic, neuro, or nephrotoxicity; and on pathological examination appear to have lower organ toxicity compared to the standard intravenous cisplatin. the nanoconjugates do not cause injection site or lymph node toxicities. The preferential intralymphatic translocation and accumulation of the nanoconjugates provides advantages for use in combination regimens for breast cancer with other chemotherapeutics.

In accordance with the present invention, the nanoconjugate can deliver cisplatin effectively to be use alone or as part of a combination therapy with significantly less toxicity. The intralymphatic delivery model using nanoconjugates not only increases drug concentrations in loco-regional nodal tissue significantly above the standard cisplatin formulation (74% greater AUC), but it also exhibits sustained release kinetics allowing lower $C_{max}$ levels which lower organ toxicity over time. The only tissue level that was significantly different was the axillary lymph nodes ipsilateral to the drug injection. This translated into almost double the concentration of cisplatin penetrating the loco-regional nodes using nanoconjugates injected directly into the breast subcutaneously. Therefore, nanoconjugates that are preferentially translocated to the lymphatics significantly boosts the concentration of drug to treat and/or inhibit loco-regional tumor cell development in the lymphatics.

Also, the nanoconjugates can be successful in treating and/or inhibiting the spread of cancer because of the intralymphatic delivery of chemotherapeutics using hyaluronan as a targeted nanocarrier to the axilla. The preferential intralymphatic delivery can preferentially treat at-risk regional lymph nodes and avoid systemic toxicities associated with intravenous or oral drug administration. The preferential intralymphatic delivery reduces the systemic concentration but maintains a suitable level for also treating and/or inhibiting the spread of cancerous cells that are disseminated into the systemic circulation. As such, the nanoconjugates can provide a therapy for patients with sentinel nodes containing nanometastases which would not be offered lymph node dissections routinely. The nanoconjugate provides adequate systemic drug levels in a more sustained-release manner than standard therapy, but it also provides a much-needed boost to the loco-regional nodal tissue, which is at risk for harboring tumor cells not removed by nodal dissection. Additionally, the nanoconjugate can be used as a neoadjuvant for locally advanced breast cancers, and can treat or inhibit regression.

In one embodiment, a pharmaceutical formulation having the nanoconjugate is not formulated for the following delivery routes: oral, systemic, transdermal, intranasal, suppository, intravenous, or intraluminal administration.

The pharmaceutical can be configured for percutaneous, intradermal, mucosal or submucosal, subcutaneous, interstitial, intrafat, peritumoral, intramuscular injection mucosa, peritumorally, inhalation, and instillation.

The nanoconjugate of the present invention preferentially translocating to the lymphatic system after subcutaneous or interstitial administration is surprising and unexpected. In part, this is due to the preferential translocation and accumulation in the lymphatic system after subcutaneous or interstitial injection, such as into the breast tissue. The nanoconjugate of HA or dendrimer with a chemotherapeutic such as cisplatin additionally provides a therapeutic systemic dose with AUC similar or sometimes higher than standard intravenous agents (e.g., cisplatin and doxorubicin) but lower Cmax concentrations. This combination of findings allows these drugs to be used as superior adjuvant therapies for patients with loco-regional disease, with the additional benefit of being able to treat their systemic disease and with less toxicity since the Cmax is lower and this is associated with cisplatin and doxorubicin toxicity. It is also surprising that the HA nanoconjugates were substantially less toxic than standard cisplatin or doxorubicin with regard to local injection site, kidney, and ototoxicity evaluation by OAEs and by renal pathologic analysis. The lower toxicity allows for direct injection into, adjacent, or proximally into tissue or interstitial space without damaging the healthy tissue. Thus, the nanoconjugates can provide therapy to the primary tumor, the intralymphatic cancerous cells, and systemic cancerous cells.

In summary, the nanocarrier delivery system is superior to standard drug formulations in (1) its efficacy and ability to treat cancers in animals, (2) its lower toxicity profile, and (3) its longer dosing interval (weekly or biweekly versus daily with intravenous agents). The subcutaneous injection offers patients a less invasive treatment option than being attached to intravenous infusion pumps which carry the risk of drug extravasation.

The nanoconjugate can be included in a pharmaceutical composition with an acceptable carrier that formulates the nanoconjugate for suitable administration, such as subcutaneous. Suitable preparations for subcutaneous administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

According to the methods of the present invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

For injection, the nanoconjugates can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the nanoconjugates can be formulated in aqueous solutions, preferably in physiologically compatible buffers such as Hanks's solution, Ringer's solution, or physiological saline buffer.

The nanoconjugates can be formulated for subcutaneous administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

Sterile injectable forms of the compositions of this invention may be aqueous or a substantially aliphatic suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The involvement of the lymphatic system in breast cancer metastasis is well established, yet there are no effective non-surgical treatments to overcome lymph node metastases and disease progression. The greatest challenge with chemotherapy of lymphatic metastases is maximizing the amount of agent which actually is retained in the lymph nodes while avoiding systemic absorption and toxicity.

The lymphatically-localized chemotherapy provided by the present invention is an innovative leap in breast cancer therapy. The HA or dendrimer nanocarriers for chemotherapeutic drugs can treat locally advanced breast cancer utilizing both a targeted and lymphatic delivery approach. The use of lymphatic targeted nanocarriers for intralymphatic drug delivery in breast cancer is highly innovative and has never been performed to date. By increasing drug loco-regional AUC over that achievable by standard chemotherapy drugs this technology provides significant neoadjuvant therapy in locally advanced breast cancer. Additionally having a targeted approach with better retention and sustained release of drug from the lymphatics should decrease systemic toxicity of the drugs leading to a combination of better tumor efficacy and lower toxicity.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited and/or shown herein are incorporated herein by specific reference.

EXPERIMENTAL

Hyaluronan (HA) from microbial fermentation was purchased from Lifecore Biomedical (Chaska, Minn.) as sodium hyaluronate and used without further purification. Heparin solution was purchased from Abraxis Pharmaceutical Products (Schaumburg, Ill.). All other reagents were purchased from Fisher Scientific (Pittsburgh, Pa.) or Sigma Aldrich (St. Louis, Mo.) and were of ACS grade or better. Milli-Q water was used in all experiments. The MDA-MB-468LN cell line was kindly provided by Ann Chambers (London Health Sciences Center, London, Ontario), while MCF-7 and MDA-MB-231 cells were obtained from the American Tissue Culture Collection (ATCC, Manassas, Va.). Animal procedures were approved by the University of Kansas Institutional Animal Care and Use Committee. Sprague-Dawley rats were purchased from Charles River Laboratories (Wilmington, Mass.).

1. Synthesis of HA-Cisplatin Conjugates

Figure 9:
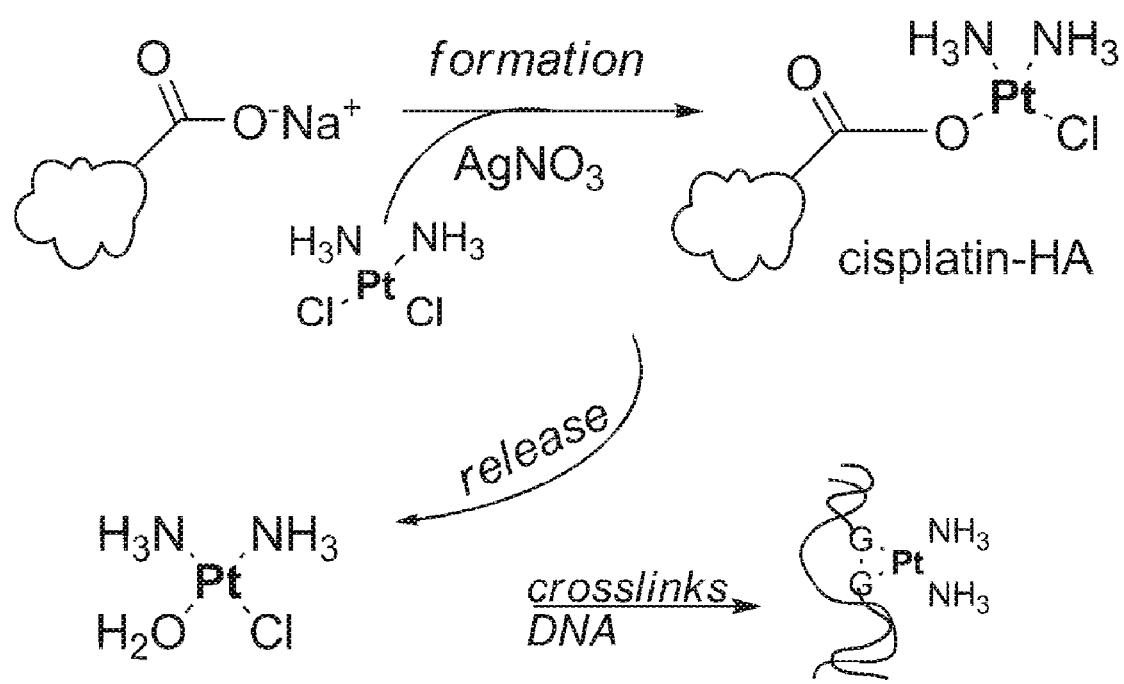
FIG. 9 is a schematic representation of the synthesis of an intralymphatic chemotherapeutic and its function in chemotherapy.

Cisplatin was conjugated to HA (35,000 g/mol) based on previously reported procedures (S. Cai, Y. Xie, T. Bagby, M. S. Cohen, and M. L. Forrest. Intralymphatic chemotherapy using a hyaluronan-cisplatin conjugate. *J. Surg. Res.* 147: 247-252 (2008); Y. I. Jeong, S. T. Kim, S. G. Jin, H. H. Ryu, Y. H. Jin, T. Y. Jung, I. Y. Kim, and S. Jung. Cisplatin-incorporated hyaluronic acid nanoparticles based on ion-complex formation. *J Pharm Sci.* (Epub.): (2008)), with and without the addition of silver nitrate as an activating agent. Typically, HA (100 mg) and cisplatin (45 mg) were dissolved in $H_2O$ (20 mL) and stirred in the dark for four days under argon at ambient temperature (ca. 25° C.). The reaction mixture was filtered (0.2-μm nylon membrane) and dialyzed against $H_2O$ (10,000 MWCO; Pierce, Rockford, Ill.) for 48 hrs at 4° C. protected from light. Following dialysis, the crude product was concentrated and stored at 4° C. The degree of cisplatin substitution was determined by atomic absorption spectroscopy (AAS) (Varian SpectrAA GTA-110 with graphite furnace). The furnace program was as follows: ramp 25 to 80° C., hold 2 s, ramp to 120° C., hold 10 s, ramp to 1000° C., hold 5 s, ramp to 2700° C., hold 2 s, cool to 25° C. over 20 s. The graphite partition tube was cleaned every 40 samples by baking at 2800° C. for 7 s. Argon was used as the injection and carrier gas. The resulting conjugate is referred to as HA-cisplatin, cisplatin-HA, HA-CDDP, HA-Pt, although the conjugate is [PtCl(H$_2$O)(NH$_3$)$_2$]OOCO-HA (FIG. 9).

The structure of cisplatin lends itself to complex formation with polycarboxylic polymers, since one or more of the chlorides can be displaced allowing formation of a labile ester linkage with the polymer. cisplatin was highly conjugated to HA with typical conjugations of 0.20 w/w platinum/complex (approximately 65% cisplatin conjugation efficiency). In previous studies, cisplatin conjugates were synthesized by first activating HA with AgNO$_3$; however, it has now been found that eliminating this step does not significantly reduce conjugation and it reduces potential silver toxicity. The AAS produced a linear curve in the range of 10 to 450 ng/mL ($R^2$=0.999) with a limit of detection of 5 ng/ml. Concentrated samples were diluted with water into the linear analytical range prior to analysis.

Fluorescent conjugates of HA were formed by condensation of Texas Red hydrazide to HA. HA (35 000 MW, 100 mg) in 10 mL of 30% H$_2$O:EtOH was activated with 2-chloro-1-methylpyridinim iodide (33 mg) and triethylamine (35 μL). After the addition of Texas Red hydrazide (AnaSpec Inc., San Jose, Calif.) (2 mg in 0.4 mL of DMSO), the mixture was refluxed for 24 hrs. Workup proceeded by dialysis against H$_2$O for 48 hrs at ambient temperature, followed by lyophilization. Conjugation efficiency was determined using a molar extinction coefficient of 81 800 M$^{-1}$ cm$^{-1}$ at λ 588 nm.

Cisplatin was highly conjugated to HA, with typical conjugations of 0.25 w/w cisplatin/complex using a starting ratio of 0.5 w/w cisplatin/HA. Up to 0.75 w/w cisplatin/complex was attempted with decreasing efficiency (Table 4).

2. In Vivo Cell Toxicity

The lymphatically metastatic breast cancer cell line MDA-MB-468LN was maintained in modified Eagle's medium alpha supplemented with 10% fetal bovine plasma, 1% L-glutamine, and 0.4 mg/mL G418 (geneticin). Additional breast cancer cell lines MDA-MB-231 and MCF-7 were maintained according to protocols provided by the ATCC. Preceding proliferation studies, cells were trypsinized and seeded into 96-well plates (5,000 cells/well). After 24 hrs, cisplatin, HA-cisplatin (with or without silver activation), or HA was added (n=12; 7 concentrations), and 72 hrs post-addition, resazurin blue in 10 μl of phosphate-buffered saline was added to each well (final concentration of 5 mM). After 4 hrs, well fluorescence was measured ($λ_{ex}$ 560 nm, $λ_{em}$ 590 nm) using a fluorophotometer (SpectraMax Gemini; Molecular Devices, Sunnyvale, Calif.). IC$_{50}$ was determined as the midpoint between saline (positive) and cell-free (negative) controls for each plate.

Cell toxicity was determined as the reduction in cell proliferation over 72 hrs. HA-cisplatin conjugates with and without silver had similar cytotoxicity to free drug in cell culture (Table 1). No appreciable difference in toxicity was detected between cisplatin and HA-cisplatin using three different human breast cancer cell lines (Table 1). HA showed no toxicity at 10 mg/ml, the upper limit of testing in all cell lines compared with saline controls (data not shown).

3. Pharmacokinetics and Tissue Distribution

Sprague-Dawley rats (female, 200-250 g) were cannulated in the left jugular vein under isoflurane and allowed to recover overnight. Animals were then injected intravenous with cisplatin (1.0 or 3.3 mg/kg; n=5) or subcutaneous with HA-cisplatin (1.0 or 3.3 mg/kg equivalent cisplatin; n=5) under isoflurane anesthesia. Subcutaneous injections were given in the uppermost right mammary fatpad of the animal. Whole blood was withdrawn (100 μl) from the cannula at 0, 5 min, 0.5, 1, 2, 4, 6, 12, 24, 48 and 96 hrs after dosing and placed into 2-ml centrifuge tubes pretreated with heparin. The cannula was washed before and after withdrawal with saline and then heparin locked. The whole blood was centrifuged at 17,000×g for 5 mins, and the plasma was frozen at −80° C. until analysis. Animals were euthanized 96 after treatment. The right ipsilateral axilla nodes (treated side), left contralateral axilla nodes (control side), and major organs (liver, kidneys, heart, spleen, lungs, brain, muscle, bladder) were excised; washed with 0.9% saline; and stored at −80° C. until analysis. Tissue samples were prepared using a procedure reported previously (S. Cai, Y. Xie, T. Bagby, M. S. Cohen, and M. L. Forrest. Intralymphatic chemotherapy using a hyaluronan-cisplatin conjugate. *J. Surg. Res.* 147:247-252 (2008)). Typically, 50 mg of tissue sample was digested using 1.5 ml of 6.7% nitric acid for 2 hours at 80° C. After digestion, samples were homogenized (Tissue Tearor; BioSpec Products Inc., Bartlesville, Okla.) and centrifuged. The supernatant and plasma samples were analyzed by AAS as described in the Synthesis section. The pharmacokinetics of subcutaneous HA-cisplatin were compared to intravenous cisplatin in Sprague-Dawley rats. HA-cisplatin accumulated more preferentially in the draining ipsilateral axillary lymph nodes than did the intravenous cisplatin control (FIG. 1A); preferential accumulation was still evident at 48 hrs post-injection even though the in vitro disassociation half-life of cisplatin from HA is 10 hrs. The ipsilateral axillary node AUC$_{0-96hrs}$ of HA-cisplatin when injected locally was 3.8-fold greater than intravenous cisplatin (p<0.001), and the peak node concentration ($C_{max}$) of HA-cisplatin was 6.2-fold greater than intravenous cisplatin.

Figure 1B:
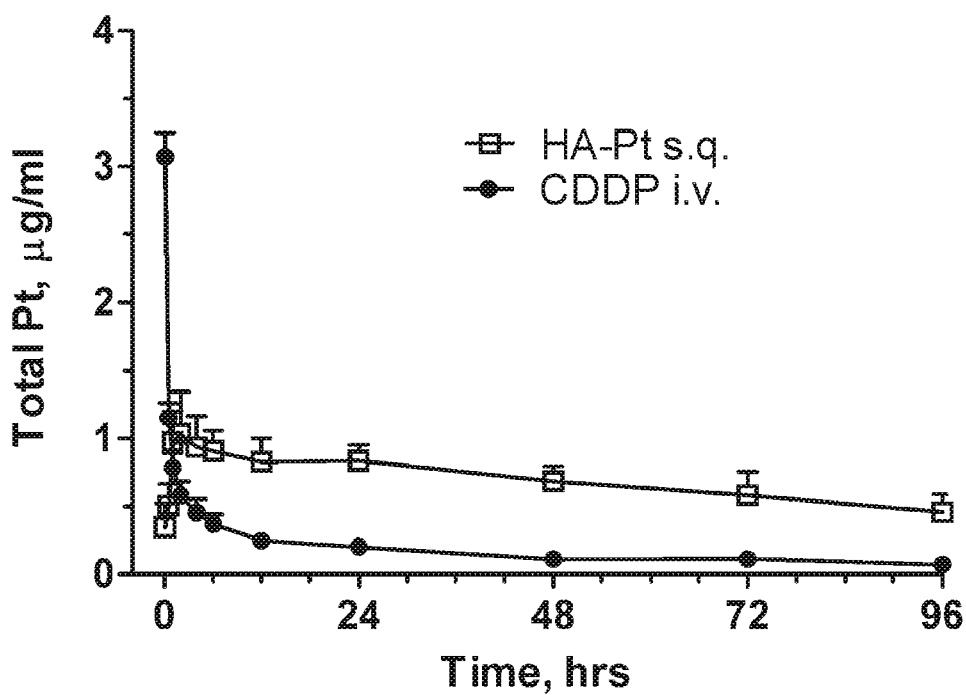

The most significant, dose-limiting toxicities of cisplatin therapy are nephrotoxicity followed by neurotoxicity, both of which are strongly influenced by peak plasma concentration. The peak plasma concentration intravenous cisplatin was 3.1-fold greater than subcutaneous HA-cisplatin. The release of cisplatin into the systemic circulation was slow, and the resulting plasma AUC of HA-cisplatin was 3.9-fold greater than intravenous therapy with cisplatin, which is consistent with longer lymphatic retention of the nanocarrier HA-cisplatin (FIG. 1B, Table 2). Concentration graphs for all tissues are included in supplement (FIG. 8A-8H).

Figure 10A:
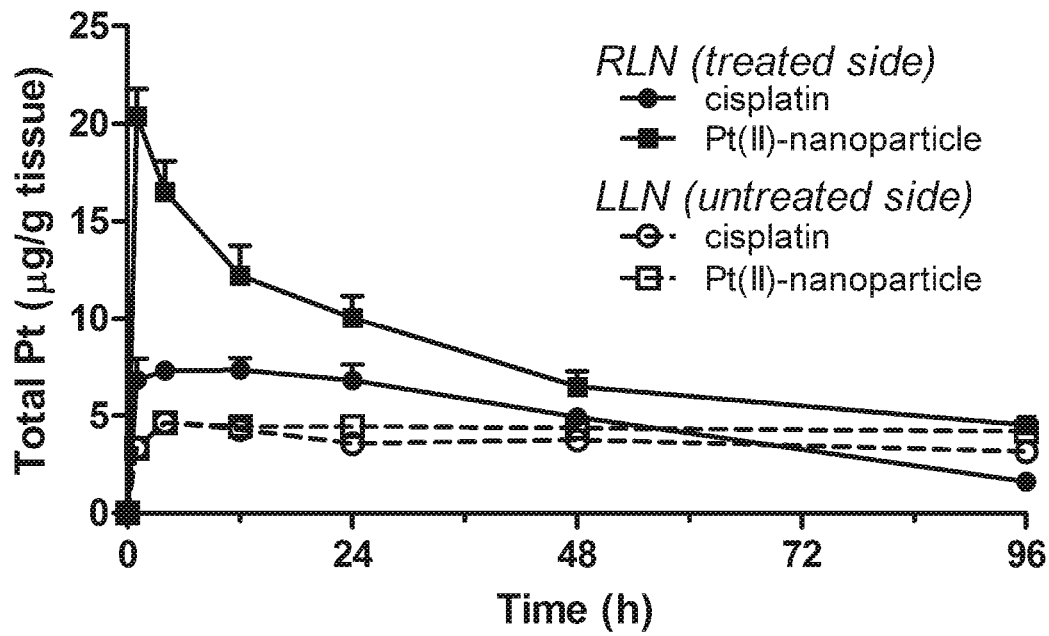
FIGS. 10A-10B are graphs that illustrate the total amount of agent after subcutaneous injection.
Figure 10B:
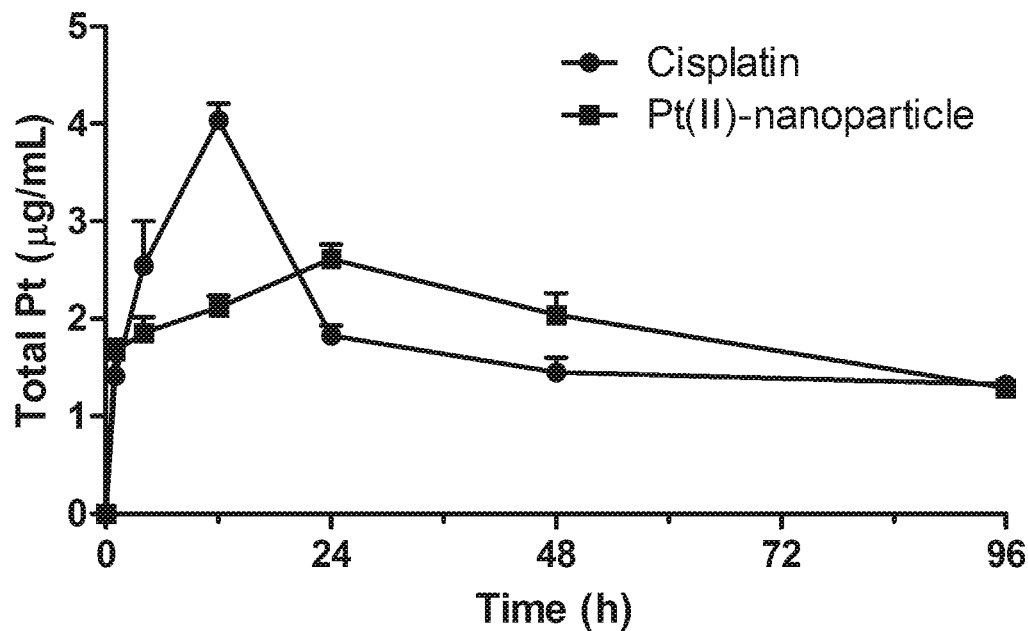
Figure 11A:
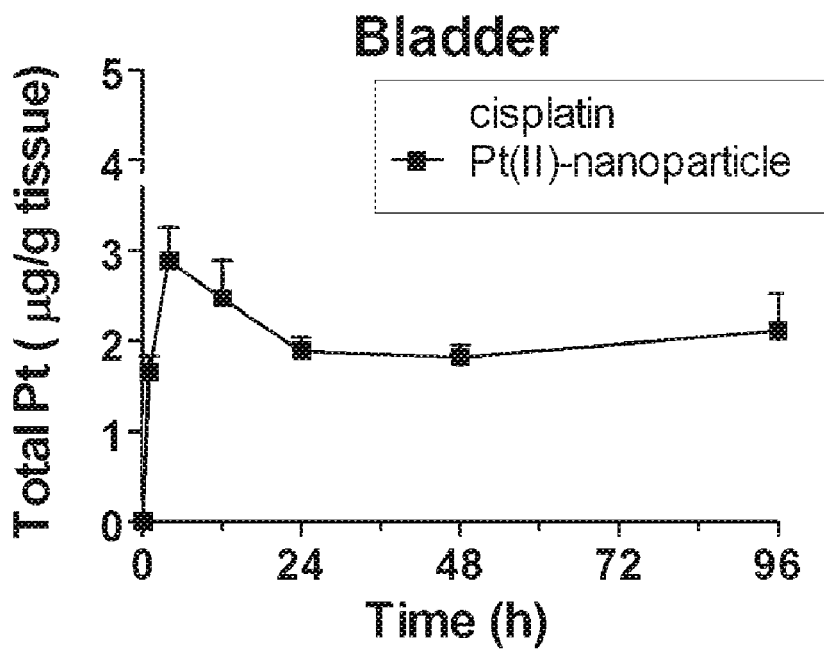
FIGS. 11A-11H are tissue concentration graphs for various tissue (e.g., FIG. 11A is bladder, FIG. 11B is brain, FIG. 11C is heart, FIG. 11D is kidney, FIG. 11E is liver, FIG. 11F is lungs, FIG. 11G is muscle, and FIG. 11H is spleen) concentrations of cisplatin after subcutaneous injection of cisplatin-HA (10 mg/kg cisplatin basis) into the right mammary fatpad.
Figure 11B:
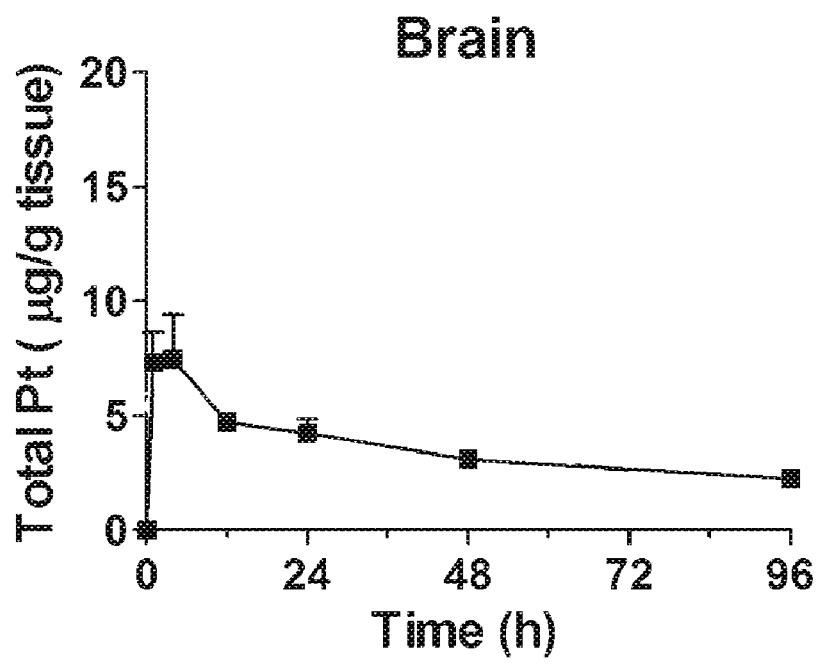
Figure 11C:
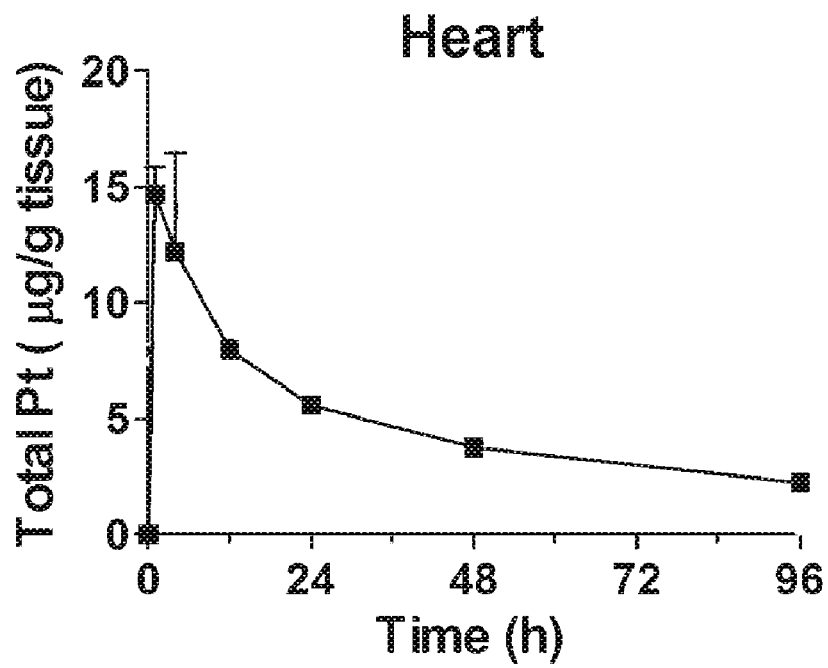
Figure 11D:
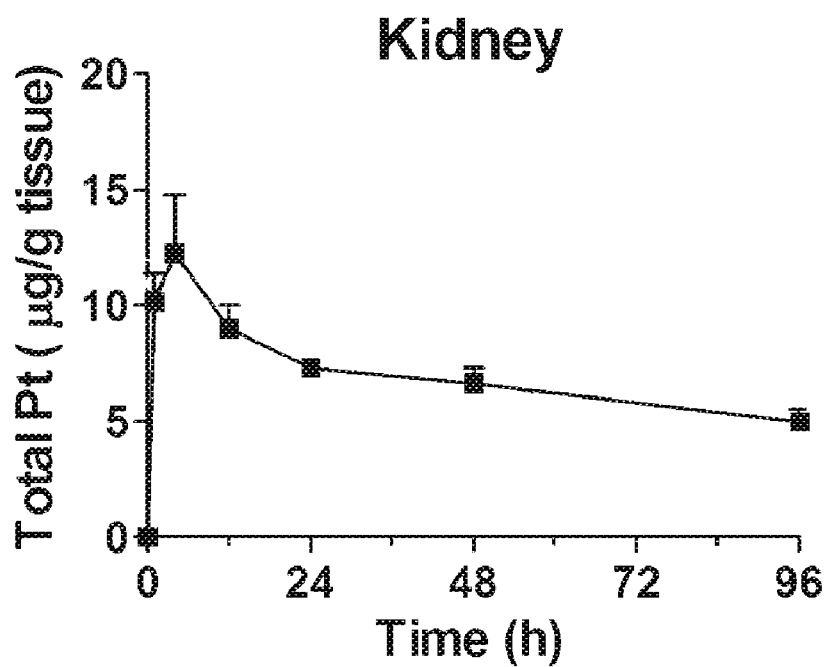
Figure 11E:
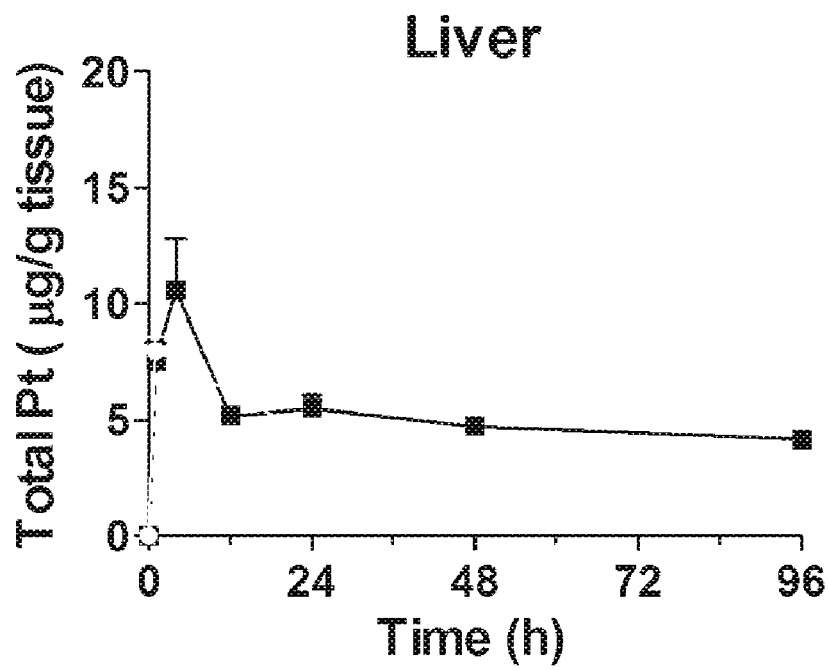
Figure 11F:
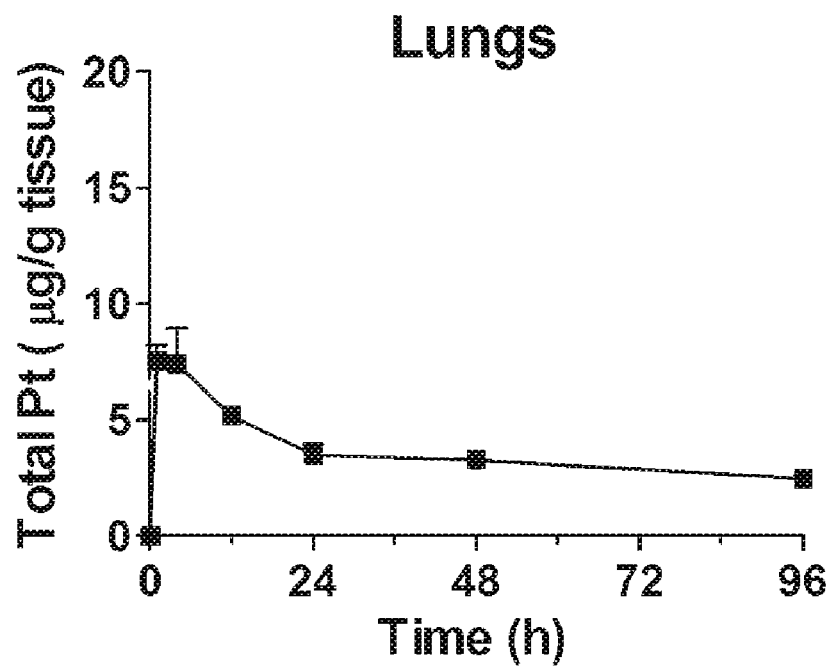
Figure 11G:
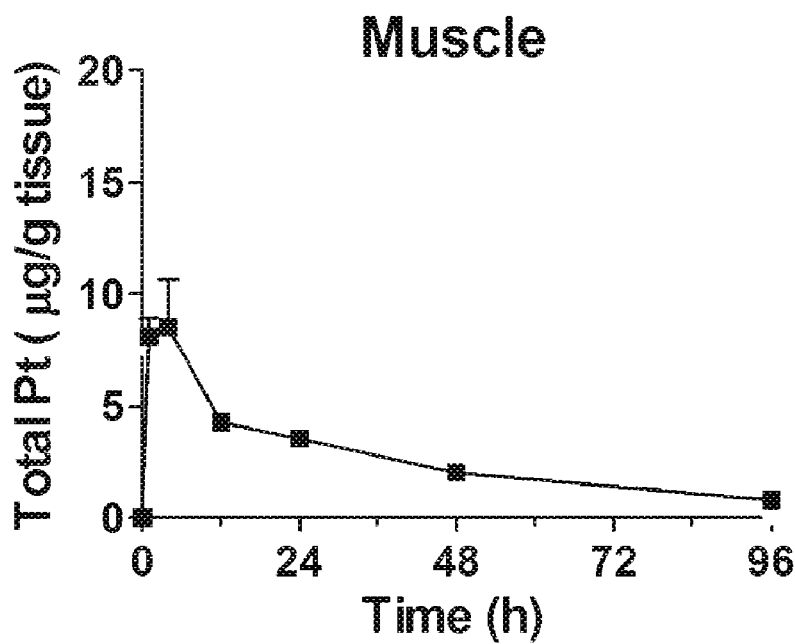
Figure 11H:
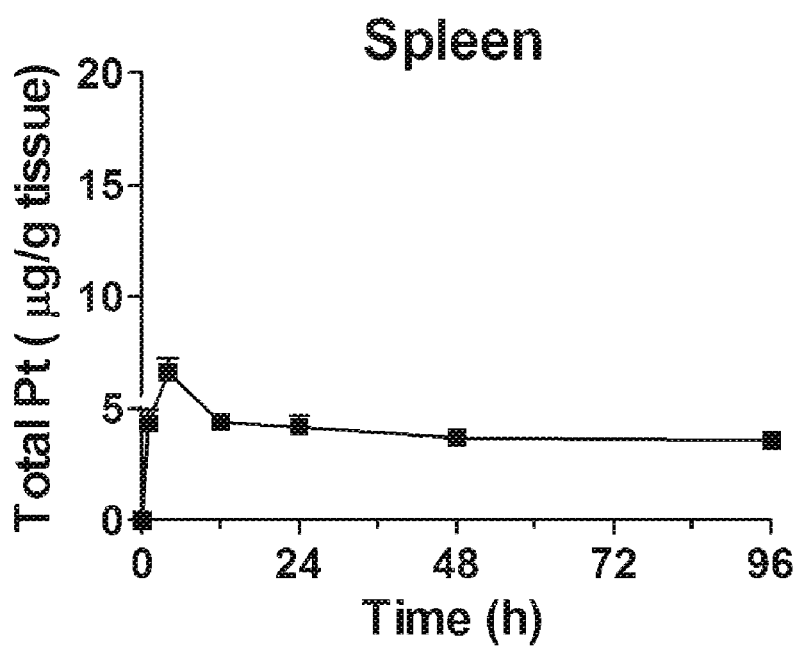

Additionally, Sprague-Dawley rats (200-250 g females, Charles River) were placed under isoflurane anesthesia and injected subcutaneously (100 μL) into the right mammary fat pad with cisplatin-HA or cisplatin in 0.9% saline (3.5 mg/kg equivalent cisplatin) (n=5). Animals were allowed to recover with access to food and water. After 1, 4, 12, 24, 48 and 96 hrs post-injection, animals were euthanized by isoflurane overdose. Organs and tissues were washed with 0.9% saline and frozen (−80° C.) until analysis. Plasma was separated by centrifugation from whole blood and frozen (−80° C.). Conjugation of cisplatin to HA impacted the local concentration of cisplatin in draining lymph nodes with a minor effect on systemic concentrations (FIGS. 10A-10B, Table 5). Over the experimental timeframe of 96 hrs, the area-under-the-curve (AUC) of cisplatin-HA conjugates in the right lymph node (RLN), which drains the injection site, was 74% greater than cisplatin in saline (p=0.0001), and the RLN had increased tissue concentrations over the examined period (FIG. 10A). The AUC of cisplatin-HA in the non-draining left lymph node (LLN) was not significantly different from cisplatin in saline (p=0.12).

A burst release of free cisplatin appeared in the plasma concentration profile (FIG. 10B), whereas cisplatin-HA demonstrated a longer, sustained release into the plasma. This is significant because dose-limiting toxicities of cisplatin therapy are strongly influenced by peak plasma concentration. There was not a significant difference in the plasma AUC between cisplatin-HA and cisplatin (p=0.13). Thus, localized therapy with cisplatin-HA may generate sufficient serum concentrations to treat distant metastases, while providing a boost therapy for the breast lymphatics. The distribution of cisplatin to other organs was not significantly different over the study period (FIG. 11, Table 5).

4. Long-Term Toxicology

Sprague-Dawley rats (35 females) were randomly divided into 7 study groups of 5 animals each: 1.0 mg/kg subcutaneous HA-cisplatin (with and without silver; platinum equivalent to 1.0 mg/kg cisplatin), 3.3 mg/kg subcutaneous HA-cisplatin (with and without silver), intravenous cisplatin at 1.0 and 3.3 mg/kg, and subcutaneous HA (control; HA equivalent to 3.3 mg/kg HA-Pt). Each animal was administered a single bolus dose at the beginning of the 30-day study period. Urine samples were collected every day during the first two weeks of the study and every four days during third and fourth week of the studies (except for the 3.3 mg/kg HA-cisplatin with silver group). In order to reduce the stress to animals, subjects were housed in metabolic cages for 12 hrs to collect approximately 5 ml of urine and then returned to cages with bedding until the next collection period. Urine samples were centrifuged at 17,000×g for 5 mins and stored in −80° C. freezer until creatinine analysis.

Urine creatinine was analyzed using the QuantiChrom™ Creatinine Assay Kit according to the manufacturer's instructions (BioAssay Systems, Hayward, Calif.). Creatinine concentration of the sample was calculated as $(OD_{SAMPLE\ 5} - OD_{SAMPLE\ 1})\ (OD_{STD\ 5} - OD_{STD\ 1}) \times [STD]$ (mg/dL). $OD_{SAMPLE5}$ $OD_{SAMPLE1}$, $OD_{STD5}$, and $OD_{STD1}$ are $OD_{510nm}$ values of sample and standard at 5 min and 1 min, respectively.

The animals were euthanized at the end of the study (30 days) and the liver, bilateral kidneys, spleen, lungs, heart, right (ipsilateral) and left (contralateral) axillary nodes, and brain were excised intact and stored in 80% alcoholic formalin solution overnight for fixation before slide mounting. Mounting using haematoxylin & eosin (H&E) staining were conducted by Veterinary Lab Resources (Kansas City, Kans.). The pathological examination was performed by a blinded board-certified veterinarian pathologist (University of Kansas Medical Center, Kansas City, Kans.).

Urine creatinine levels are an indirect indicator of renal function and renal toxicity, with a decrease in creatinine excretion corresponding to decreased renal function and possible renal toxicity or damage. Significant renal toxicity was observed in animals given the high dose silver regimen (3.3 mg/kg), with a 30% decrease in creatinine excretion at 3 days and 70% decrease at 4 days. All animals in this group died within 1 week of treatment due to drug-related cachexia. In contrast, the silver-free high dose HA-cisplatin did not demonstrate significant toxicity, and creatinine levels remained near pre-dosing levels throughout the study's duration. Similar renal function was observed in both groups when animals were administered low doses (1.0 mg/kg) of either HA-cisplatin with silver or HA-cisplatin without silver treatment (p>0.05, day 1 to 30) (FIG. 2A-2B).

At the conclusion of the 30 day toxicity study, animals were euthanized and a full pathological examination performed. Brain tissue and underlying tissue of the injection site were normal with no microscopic changes for all study groups. Very mild changes in lymph nodes were detected for high dose intravenous cisplatin and subcutaneous HA-cisplatin formulated without silver. Lymphoid tissue from low dose subcutaneous HA-cisplatin with silver had normal appearance indicating by well-populated small lymphocytes showing little or no follicular architecture (FIG. 6A-6F). Very mild changes were observed in the livers for animals receiving both low dose cisplatin intravenous and low dose HA-cisplatin subcutaneous indicated by the presence of mild inflammation in the sinusoids (FIG. 4A-4F). Mild degeneration with some sinusoidal necroses were observed for animals receiving high dose intravenous cisplatin and high dose subcutaneous HA-cisplatin treatment; necroses were more severe in the intravenous cisplatin group. In addition, 60% of animals receiving low dose intravenous cisplatin were observed with mild renal necrosis including hemorrhage into the renal tubules along with tubular edema (FIG. 3A-3F). In contrast, none of the animals receiving low dose subcutaneous HA-cisplatin had renal necrosis. Similarly, 4 of 5 (80%) animals receiving high dose intravenous cisplatin compared to 1 of 5 (20%) animals receiving high dose subcutaneous HA-cisplatin were diagnosed with mild renal necrosis (Table 3). Overall, the pathology studies demonstrated that the silver-free HA-cisplatin conjugates demonstrated lower incidence of both renal and hepatic toxicity compared to the conventional intravenous cisplatin treatment at all dose ranges. Additionally no neurotoxicity in the brain or local injection site toxicity in the underlying muscle tissue was observed in the treated animals (FIGS. 5A-5F and 7A-7D).

5. In Vitro Drug Release

In vitro release rate of cisplatin from cisplatin-HA was determined in phosphate buffer with and without saline. Cisplatin-HA was added to 3,500 MWCO dialysis bag (Pierce) and placed in a phosphate-buffered water bath (pH 7.4, 37° C.) or physiological saline (140 mM). Samples were taken from the dialysis bags at predetermined time points and remaining cisplatin concentration determined by AAS. The release rate of cisplatin from complexes was determined in both phosphate buffered saline and water. The Cl⁻ in saline was expected to more rapidly displace cisplatin, increasing the release rate. The release of drug showed near first order release kinetics with a release half-life of 42 h in water and 10 h in physiological saline. The AAS produced a linear concentration curve from 10 to 450 ng/mL ($R^2$=0.9998), with a limit of detection of 5 ng/mL and a limit of quantification of 10 ng/mL (5% standard deviation). Cisplatin recovery from cisplatin-HA spiked tissues was: plasma, 82±4% (STD); lymph nodes, 92±2%; bladder, 88±1%; brain, 94±0.3%; heart, 97±1%; kidneys, 98±1%; liver, 100±1%; lung, 94±1%; muscle, 95±1%; spleen, 97±1%. cisplatin recovery from cisplatin-spiked tissues was: plasma, 80±3%; lymph nodes, 92±6%; bladder, 86±3%; brain, 93±10%; heart, 93±5%; kidneys, 100±2%; liver, 100±7%; lung, 95±8%; muscle, 100±5%; spleen, 96±9%.

Figure 16:
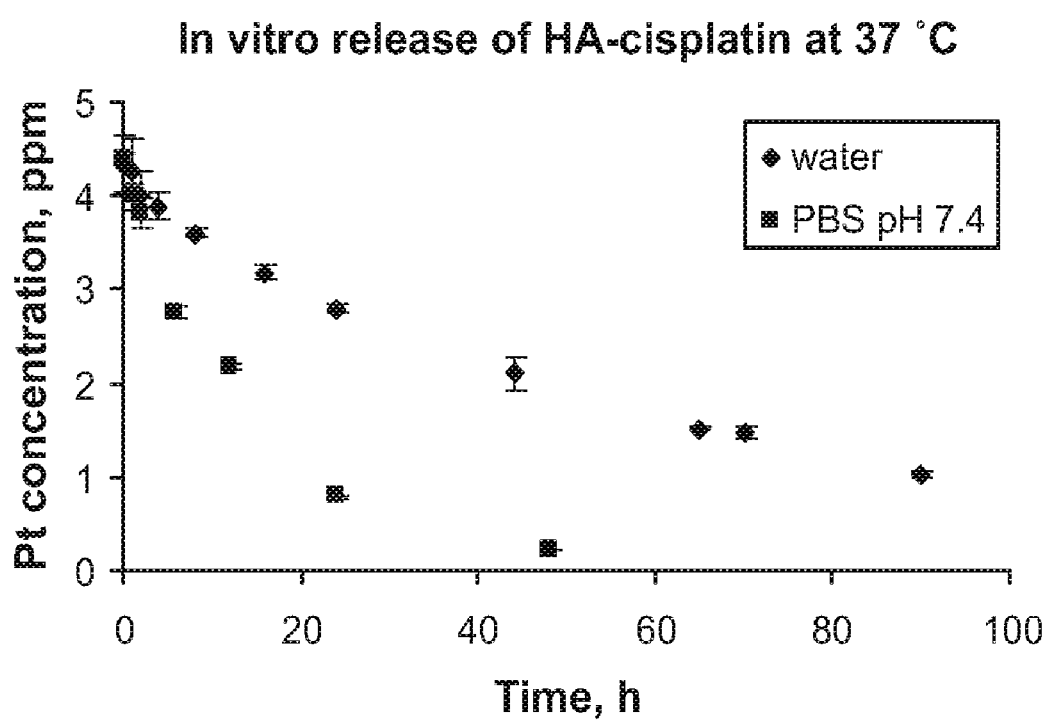
FIG. 16 shows the in vitro HA-cisplatin release rate at 37° C. for water solution and phosphate buffer solution (PBS).

FIG. 16 illustrates the in vitro HA-cisplatin release rate at 37° C. for water and PBS solutions. Table 6 shows the associated half life.

6. In Vitro Cell Toxicity

Cell lines were seeded into 96-well plates (5000 cells/well) in DMEM medium supplemented with 5% FBS and 1% penicillin/streptomycin. After 24 hrs, cisplatin, cisplatin-HA, or HA was applied (n=12, 7 concentrations), and 72 hrs post-addition, reazurin blue in 10 μL PBS was applied to each well (final concentration of 5 mM). After 4 hrs, well fluorescence was measured ($\lambda_{ex}$ 560 nm, $\lambda_{em}$ 590 nm) (SpectraMax Gemini, Molecular Devices), and the $IC_{50}$ determined as the midpoint between saline (positive) and cell-free (negative) controls.

Figure 12:
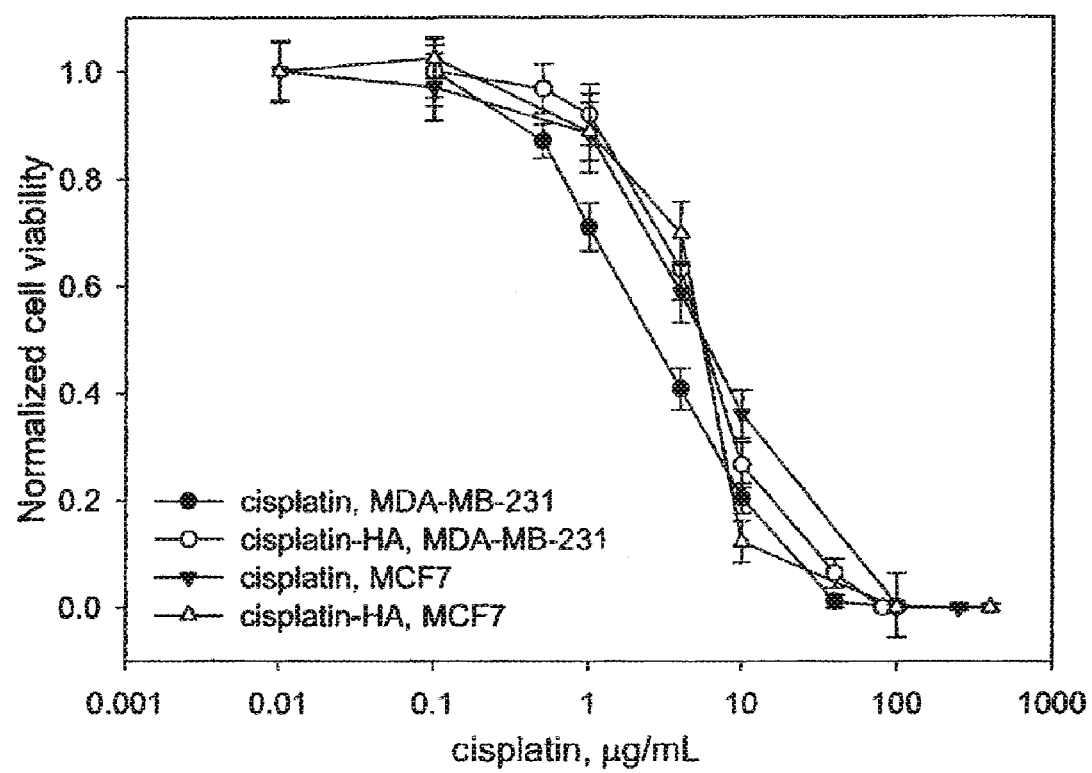
FIG. 12 is a graph that illustrates cell viability through the inhibition of human cancer cell growth by cisplatin and cisplatin-HA after 72 hrs. As a note, HA by itself showed no toxicity over the examined concentrations (up to 10 mg/mL, data not shown). This graph demonstrates that conjugating HA to CDDP did not adversely effect the anticancer effect of cisplatin in vitro as all of the cell lines demonstrated similar IC50 levels.

Cisplatin-HA conjugates had similar toxicities to free cisplatin in cell culture. Toxicity was evaluated in the highly metastatic human breast cancer cell lines MCF7 and MDA-MB-231 (FIG. 12). In both cell lines, there was no appreciable difference in toxicity between cisplatin-HA ($IC_{50}$ 7 μg/mL, cisplatin basis) and cisplatin ($IC_{50}$ 7 μg/mL). HA had no toxicity to human cells over the concentration range examined (up to 10 mg/mL, data not shown). Table 7 shows the IC50 values.

7. Atomic Absorption Spectroscopy (AAS)

In vitro release samples (n=3) and plasma samples (n=5) were diluted 200-fold and 10-fold, respectively, with 0.1% nitric acid for analysis. Tissue samples (except for lymph nodes) were prepared by digesting 50 mg of tissue in 1.5 mL of 6.7% nitric acid for 1 hr at 80° C. Lymph nodes were processed similarly using 10 mg of tissue. After digestion, samples were homogenized (Tissue Tearor, BioSpec Products Inc., Bartlesville, Okla.). All samples were centrifuged (17 000×g, 20 min), and the supernate used for analysis.

Analysis was performed on a Varian SpectrAA GTA-110 with graphite furnace and partition tubes. Samples (21 μL) were injected using the autosampler, followed by 19 μL of 0.1% nitric acid. Every 10 samples were bracked by calibration standards at 150, 300, and 450 ng/mL, and a quality control sample (150 or 300 ng/mL) every 5 samples. A full calibration curve was prepared from 1 to 450 ng/mL in 0.1% nitric acid (10 concentrations). Cisplatin recovery was determined by spiking tissue blanks with cisplatin or cisplatin-HA (50 μg/g) and processing as above. The furnace program was as follows: ramp 25 to 80° C., hold 2 s, ramp to 120° C., hold 10 s, ramp to 1000° C., hold 5 s, ramp to 2700° C., hold 2 s, cool to 25° C. over 20 s. The graphite partition tube was cleaned every 40 samples by baking at 2800° C. for 7 s. Argon was used as the injection and carrier gas.

8. In Vivo Imaging

In order for nanocarriers to deliver anticancer drugs to nano- and micrometastases in the breast loco-regional lymphatics, carriers should drain from the breast area to the diseased lymph nodes. To verify anionic nanocarriers to do, we constructed a fluorescent anionic nanocarrier by coupling 35 kDa hyaluronan with Texas Red hydrazide (AnaSpec, San Jose, Calif.) using EDAC-mediated amide coupling followed by dialysis to remove free dye (0.1% w/w dye/carrier determined spectroscopically). We injected fluorescent nanoparticles (0.25 μg in 50 μL of saline) subcutaneously beneath the nipple of a xenograft bearing lymphatic metastases.

Fluorescence was measured in 10-nm bandpass segments from 520 to 720 nm, using a cooled CCD camera with autoexposure. Images were spectrally unmixed using the automatic deconvolution tools (Maestro ver. 2.4) to limit skin and intestine autofluorescence resulting from chlorophyll in food.

Lymphatic breast tumor metastasis were induced in nude mice according to the procedure of Chambers and coworkers, who were kind enough to provide the lymphatically metastatic breast tumor cell line MDA-MB-468LN. Nude mice (25-30 g females, Charles River) were anesthesized with pentobarbital (50 mg/kg), and 100 μL of MDA-MB-468LN ($10^7$ cells/mL) was injected orthotopically into the left second thoracic mammary fatpad through a small incision later closed with a wound clip. Tumors were palpable after 4-5 wks (100-300 $mm^3$). Before imaging, mice were anesthesized, and Texas Red-HA (10 mg/mL in saline, 20 μL) was injected subcutaneously over the left mammary fatpad. The injection area was massaged gently for 5 min and fluorescently imaged after 5 and 18 hrs (CRI Maestro Flex, CRI Inc., Woburn, Mass.) using a 445- to 490-nm filtered halogen excitation light and a 515-nm longpass emission filter.

Figure 13A:
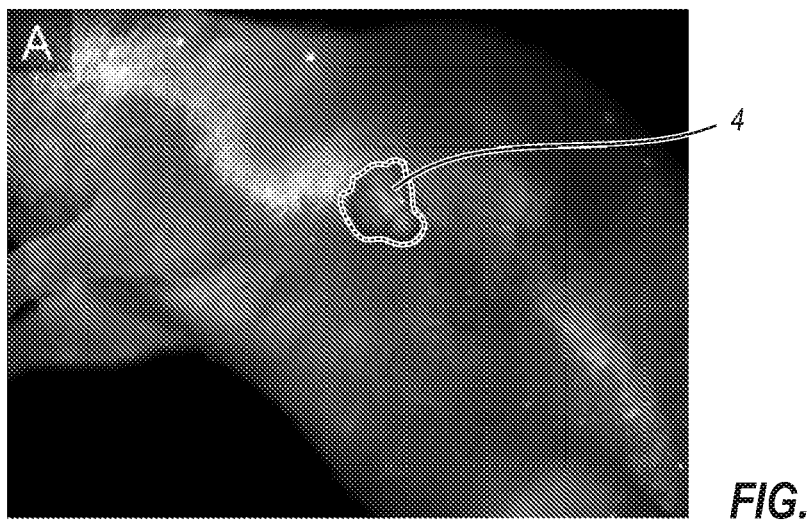
FIGS. 13A-13C are photographs showing the localization of the intralymphatic carrier after subcutaneous injection in nude mice bearing MDA-MB-468 breast lymphatic tumors expressing green fluorescent protein (GFP)

Four hours post injection, fluorescent imaging ($\lambda_{ex}$ 480, $\lambda_{em}$ 500-720 nm, spectrally deconvoluted) shows that anionic nanoparticles accumulated in a region consistent with the axillary node group (FIG. 13A). At this early timepoint, much of the carrier is still in close proximity to the injection site, although some trafficking to the axillary lymph node tumor is evident. These images are in deconvoluted, so overlapping GFP and Texas Red signals do not appear yellow. The software includes a colocalization tool the confirmed Texas Red in the area of the tumor. Accumulation of Texas Red-labeled nanocarriers is more apparent in the coronal view (FIG. 13B).

Figure 13B:
Figure 13C:
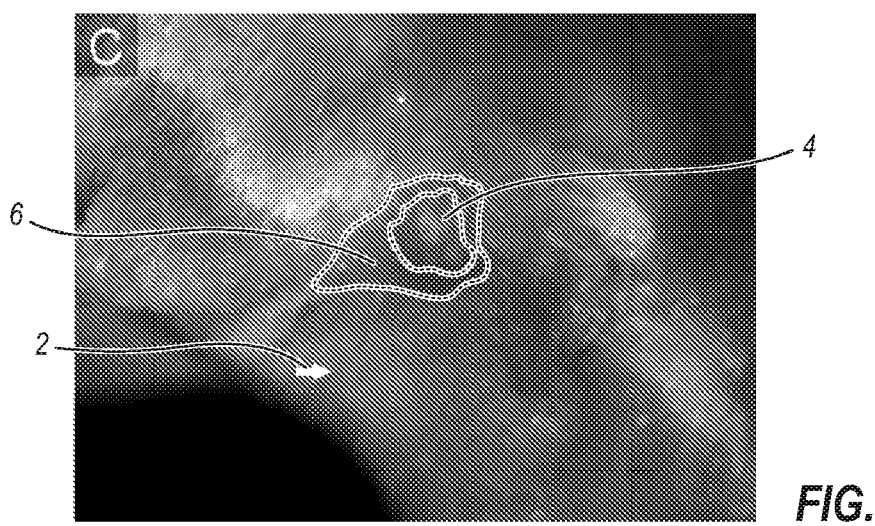

After 18 hours post-injection, the nanocarrier has concentrated in the axillary node surrounding the tumor (FIG. 13C). Of note, no carrier fluorescence appears at the injection site, and there is no apparent spread to the liver, compared against the very high axillary node levels. Obvious areas of carrier localization around the tumor are apparent in the coronal view. Kobayashi et al. observed that cationic PAMAM nanoparticles did not enter lymphatic tumors, but trafficked around them. However, anionic carriers have a much longer residence time, possibly allowing the carrier and its anticancer drug cargo to enter tumors.

FIGS. 13A-13C are show the localization of the intralymphatic carrier after subcutaneous injection in nude mice bearing MDA-MB-468 breast lymphatic tumors expressing green fluorescent protein (GFP) FIG. 13A shows the breast lymphatic tumor 4 at the time that the mice were subcutaneously injected with Texas Red-HA 6 in the left mammary fat pad. After 5 hrs and 18 hrs (FIG. 13B and FIG. 13C, respectively), the photographs show that significant HA localized in the draining nodes and co-located with the tumor (GFP-channel in green in color and marked with 4, Texas Red channel in red and marked with 6, the blue arrow 2 is the injection site).

9. Activity

Conjugation of doxorubicin to the nanocarrier did not significantly affect its anticancer activity in breast cancer cells. The 10% w/w conjugate was applied to cells, and 72 hrs later, cell proliferation was determined using the Alamar blue assay (Invitrogen Corp.). There was no statically significant difference in anticancer activity between the conjugate and free doxorubicin in three aggressive human breast cancer cell lines. Similarly, cisplatin conjugates were applied to breast cancer cells in culture. After 72 hrs, cisplatin conjugates were not significantly different from free cisplatin. Overall, conjugation of anticancer drugs to nanocarriers did not decrease the anti-proliferative effect in vitro. This may be due release of anticancer drugs from nanocarriers into the culture media, followed by uptake as with free drug. However, the microscopy uptake study suggested drugs may have activity despite conjugation to an anionic carrier.

10. Synthetic Schemes

Figure 14A:
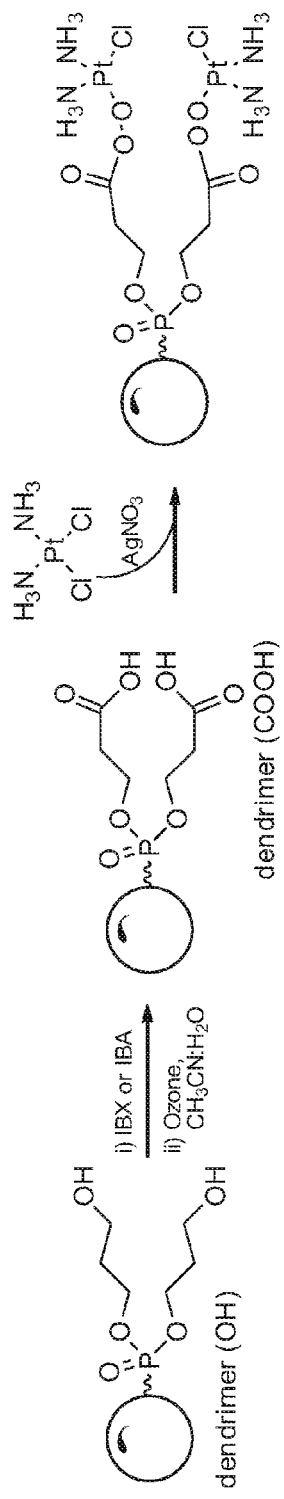
FIGS. 14A-14C are schematic diagrams of the synthesis of nanoconjugates.

FIG. 14A shows the synthesis of a dendrimer-cisplatin conjugate. The bis-hydroxypropyl phosphate termini of the dendrimer are converted into carboxylic acids, which then form a complex with cisplatin by displacement of the chloride. The resulting complexes will slowly release the potent DNA crosslinker cis-$[Pt(NH_3)_2Cl(H_2O)]^+$ at physiological conditions. In preliminary studies, we formed cisplatin conjugates to hyaluronan carriers by displacement of the platinum chloride with a carrier carboxylic acid to form —C(=O)

OO—PtCl(NH$_3$)$_2$ conjugates. A similar scheme can be used to conjugate cisplatin to the anionic dendrimer carrier. The bis-hydroxypropyl phosphate termini of dendrimers are be converted to carboxylic acids by mild reduction with Dess-Martin periodinane (DMP), IBX, or IBA, and ozonation into the carboxylic acid. Alternatively, the hydroxyls can be converted to carboxylic acids by treatment with succinic anhydride/DMAP, although this would extend the termini by four carbons and enlarge the nanocarrier. Complexes will be purified by dialysis or Sephadex, and the drug quantity on nanocarriers will be determined by graphite furnace atomic absorption spectroscopy. The optimum amount of cisplatin conjugation can be between about 10%-50% substitution, more preferably about 20%-40%, and most preferably about 25%-35%. For example, up to 25% w/w conjugation has allowed significant lymphatic uptake of Pt(II)-hyaluronan nanoparticles in vivo.

Figure 14B:
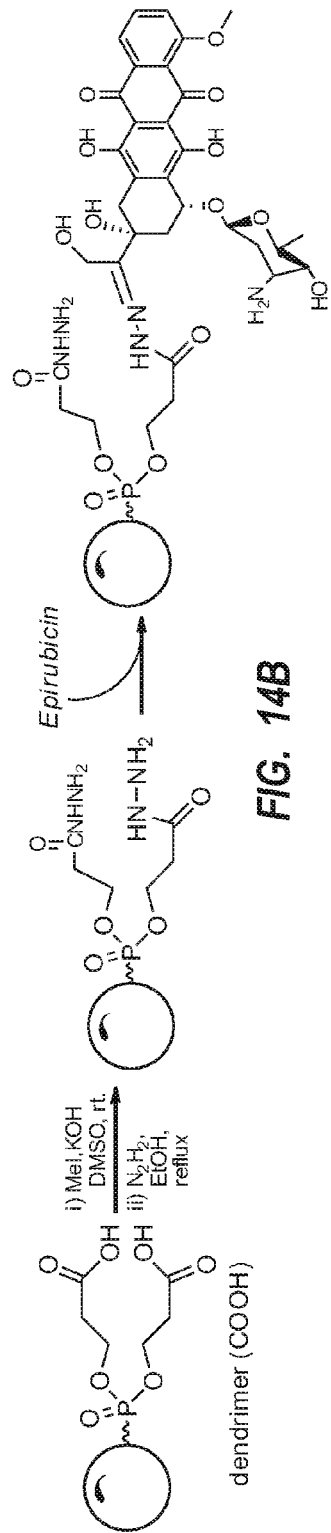

FIG. 14B shows the synthesis of dendrimer-epirubicin conjugates. The bis-hydroxypropyl phosphate termini of the dendrimer are converted into hydrazides, which then form a pH-sensitive hydrazone with the epirubicin. The resulting complexes will release epirubicin in response to decreased pH in endocytic vessels of cells (e.g. tumor cells). Nanocarrier conjugates can greatly increase the amount of anthracyclines accumulated in cancer cells.

The pH-sensitive conjugates are formed using a hydrazone linker between the anthracycline 13-carbonyl and a grafted hydrazide on the nanocarrier. The hydrazide linker was formed by graphing an adipic dihydrazide to the carboxylic acid residues using literature procedures, but a more direct strategy is to convert the nanocarrier hydroxyl termini directly into hydrazides, which will retain the size of the dendrimer. Amine termini would be expected to increase the cationic nature of the carrier, but the low pK$_a$ of hydrazides (ca. pH 4.5) will minimize this effect extracellularly. In addition, partial conversion of the hydroxyl termini can create enough hydrazides to conjugate the desired drug load. After converting the bis-hydroxypropyl phosphate termini of the dendrimer into carboxylic acids, activate and then treat the termini with hydrazine, forming hydrazide termini. The epirubicin conjugate is formed by incubation of the carrier and epirubicin at pH 6.5 to form the reversible hydrazone linker followed by dialysis or Sephadex workup to remove the unconjugated drug. The optimum amount of epirubicin conjugation can be between about 5%-20%, more preferably about 8-15%, and most preferably about 10%-12%.

Figure 14C:
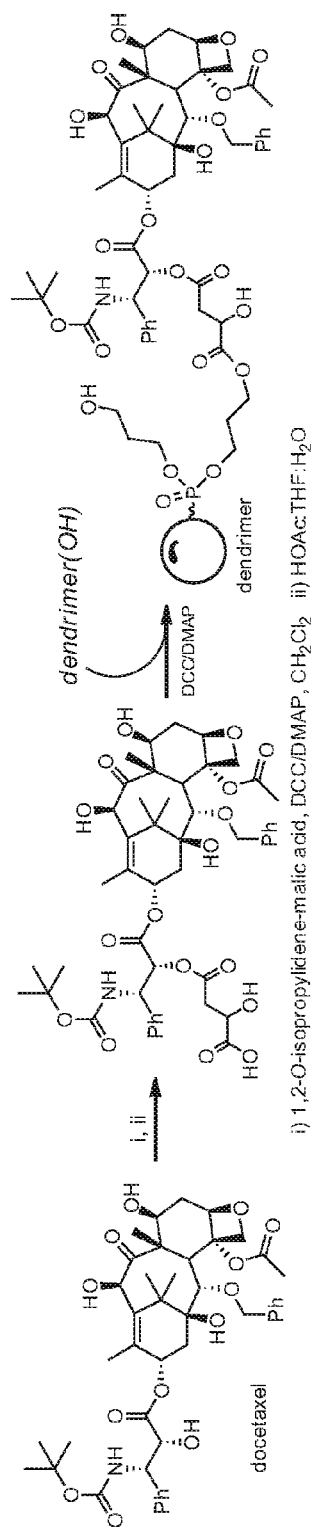

FIG. 14C shows the synthesis of dendrimer-docetaxel conjugates. The docetaxel is converted into a protected malic acid, and the new carboxylic acid is directly linked with the bis-hydroxypropyl phosphate termini of the dendrimer via an ester linkage. The resulting complex will protect tissues from docetaxel toxicity until conjugates release docetaxel in response to decreased pH in endocytic vessels and endogenous esterases. Docetaxel can be conjugated to the unmodified bis-hydroxypropyl phosphate termini of the dendrimer using by a malic acid linker grafted onto the C2 position of docetaxel using an ester bond. The docetaxel C2-OH can be condensed with 1,2-O-isopropylidene-malic acid, forming a protected malic acid of docetaxel. Deprotection with acetic acid will yield the malic acid, which can be directly coupled onto the hydroxyl arms of the dendrimer. The resulting conjugate can release docetaxel in response to acidic pH or endogenous esterases in acidic vesicles. The expected half-life after injection is expected to be greater than 4 hours, allowing sufficient time for lymphatic uptake based on our preliminary studies of anionic lymphatic nanocarriers. The optimum amount of docetaxel conjugation can be between about 5%-20%, more preferably about 8-15%, and most preferably about 10%-12%.

Figure 15A:
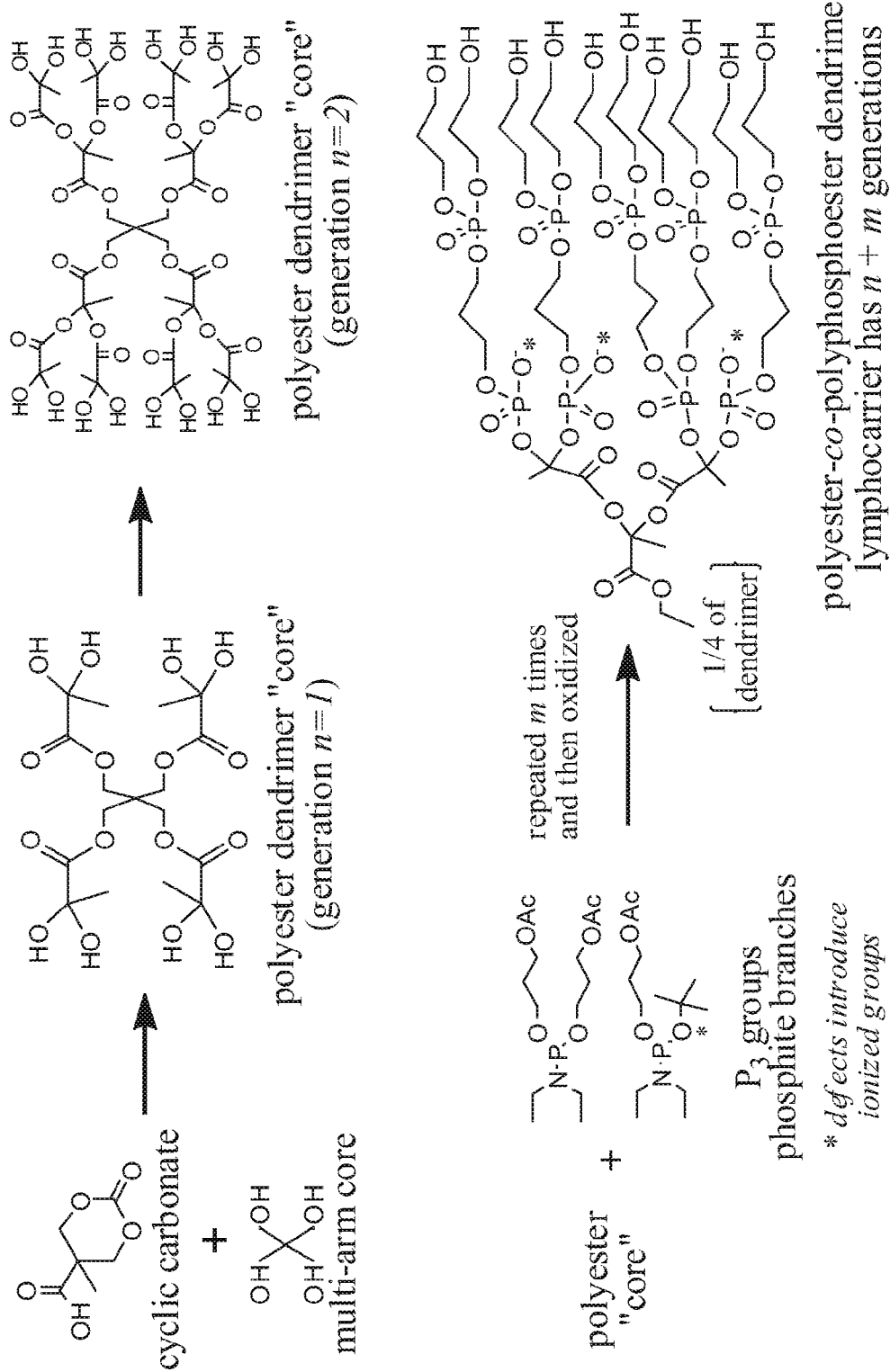
FIG. 15A is a schematic diagram illustrating the synthesis of a dendrimer.

FIG. 15A shows the synthesis of a dendrimer in accordance with the present invention, and demonstrates an overall synthetic strategy for our library, although we are examining additional "arm" groups and substituents to further improve uptake. From a multi-arm core, we are building a several generation polyester core by carbodiimide coupling, followed by deprotection of the pendant hydroxyls. Additional generations are built from these pendant groups. After 2-4 generations, we switch to a phosphite branching unit (P3). Tetrazole is used to couple the P3 branches to the pendant hydroxyls, followed by selenium conversion to the selenophosphate. "Defect" branches (red asterisks) are selectively included to yield ionizable groups when deprotected, thus integrating ionizable groups within the core to limit aggregation and increase solubility. The charge degree can be tailored by varying the ratio of defect branches. After 2-3 generations, the poly-selenophosphoester branches are fully oxidize with organic peroxide, and terminal hydroxyls are converted to carboxylic acids for cisplatin conjugation or hydrazones for doxorubicin conjugation using standard methods.

Our preliminary studies determined that this dual core strategy can facilitate synthesis. Phosphate groups can be selenium protected, otherwise the phosphate is sufficiently reactive to cleave the arm groups during conjugation; however, in later generations the inner selenophosphates become too hindered by subsequent generations for deprotective oxidation. To overcome these issues we introduce a carboxy ester core, which improves biodegradability and lessens steric crowding during oxidation of the outer phosphate groups. Fully carboxylic acid dendrimers have been developed, but these would not be water-soluble if highly substituted with hydrophobic drugs. We use the anticancer drugs cisplatin and doxorubicin as they are highly effective first-line treatments for multiple cancers including head and neck cancers (HNC) and breast cancer.

Figure 15B:
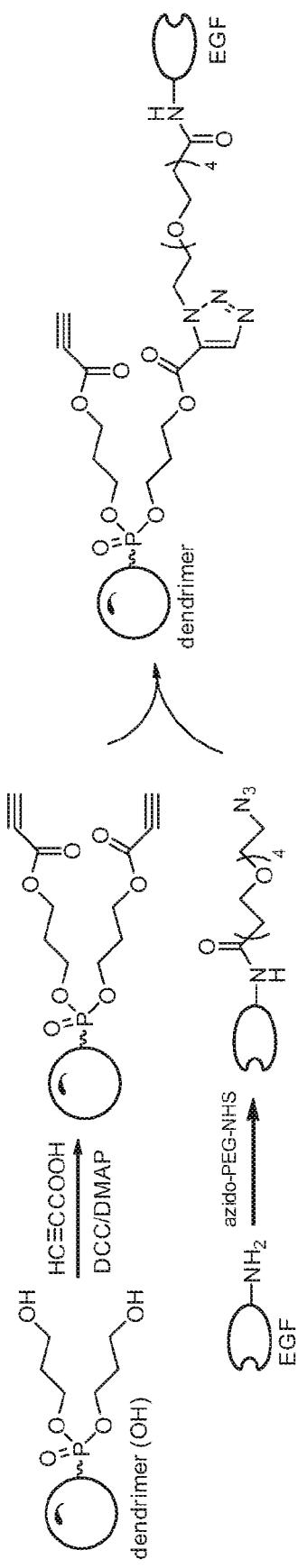
FIG. 15B is a schematic diagram illustrating the conjugation of targeting agents to nanoconjugates.

FIG. 15B shows the synthesis of targeted dendrimers. The bis-hydroxypropyl phosphate termini of the dendrimer are condensed with propiolic acid to form the alkyne-dendrimer. Alternately, the COOH or CONHNH$_2$ can be condensed with propargyl to form the alkyne-dendrimer. Using a "click" methodology, the dendrimer and the azide of EGF are coupled under aqueous conditions. This strategy can be applied to other targeting agents, e.g. HER2 antibody, EGFR antibody, PSMA, and the like.

The nanoconjugates can target breast cancer cells via the epidermal growth factor receptor (EGFR), which is highly overexpressed by aggressive breast cancers with poor prognosis. In addition, EGFR is endocytosed and can be used to internalize nanocarriers conjugated to EGF. Although EGFR is expressed at lower levels by other tissues, passive localization of the nanocarrier to the lymphatics will minimize non-specific interactions. Unlike systemic nanocarriers, the targeting moiety can improve cell uptake, as physical characteristics alone can localize anionic nanocarriers in the lymph nodes.

Epidermal growth factor (EGF) is a 6054-Da protein with lysine residues that may be used to link nanoparticles without decreasing interaction with cells. Since the termini group of the dendrimer is dependent on whether the dendrimer is used for cisplatin (COOH), docetaxel (OH) or epirubicin (C═ONHNH$_2$), it is easiest to use a "click" type linker so all chemistries can be done in aqueous solution and as a final step. EGF is functionalized using azido-PEG-NHS ester (Quanta Biodesign Ltd., Powell, Ohio). Alternatively, other targeting agents are easily added by forming the respective azide. Alkynes can be added to the dendrimer termini using DCC/DMAP chemistry and either propargyl alcohol (COOH termini) or propiolic acid (OH and C=ONHNH$_2$ termini). The resulting targeted alkyne-dendrimer is mixed with the EGF-azide with a small amount of copper catalyst to form the conjugate, followed by Sephadex or dialysis purification to remove unbound EGF.

11. Tumor Response

Nude nu/nu mice were implanted with 1×10^6 cells (MDA-MB-468LN human breast cancer cells) into the mammary fatpad, after approximately 4 weeks a 100-200 mm$^3$ tumor had developed in the axillary lymph node package. Animals were randomly divided into four treatment groups of five animals each: intravenous saline, s.q. HA, intravenous cisplatin, or s.q. HA-cisplatin. At this point, doses were administered to the animals. In the HA-cisplatin and the HA groups, HA-cisplatin (3.3 mg/kg based on Pt-content) or HA (3.3 mg/kg) was dissolved in 100 mcL saline was injected subcutaneously peritumorally. In the cisplatin and saline groups, cisplatin (3.3 mg/kg, Pt-basis) in 100 mcL saline or just saline was injected intravenously via the tail vein. In all study groups, a second dose was administered after 1 week. Tumor volumes were measured weekly using calipers and the formula: Volume=0.52×(width$^2$*length). Animals were euthanized when the tumor volume exceeded 1000 mm$^2$ or the body score index fell below 2.

Figure 17A:
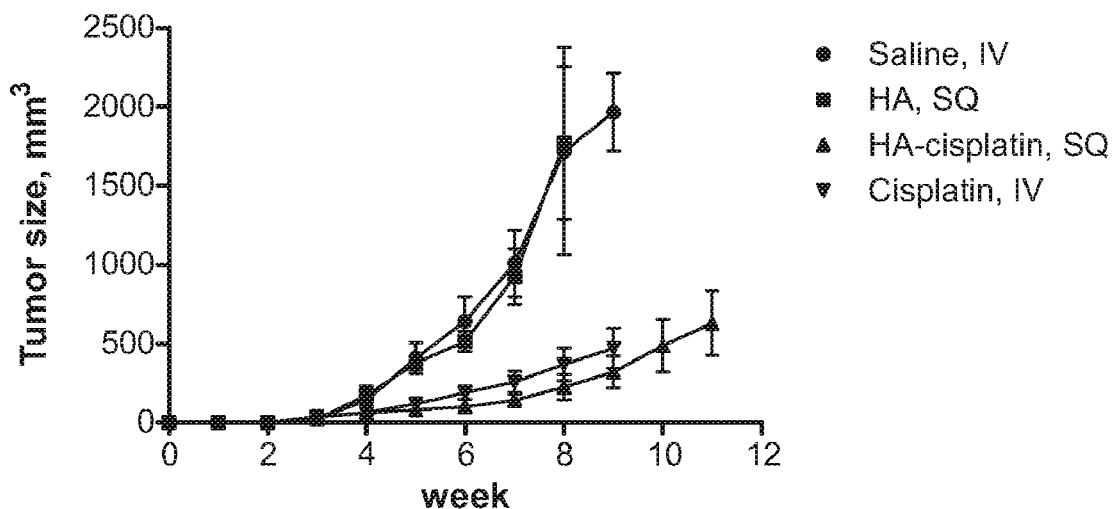
FIGS. 17A-17B show that tumor growth was delayed by HA-cisplatin treatment for 5 weeks compared to negative control group and 2 weeks compared to conventional cisplatin treatment.
Figure 17B:
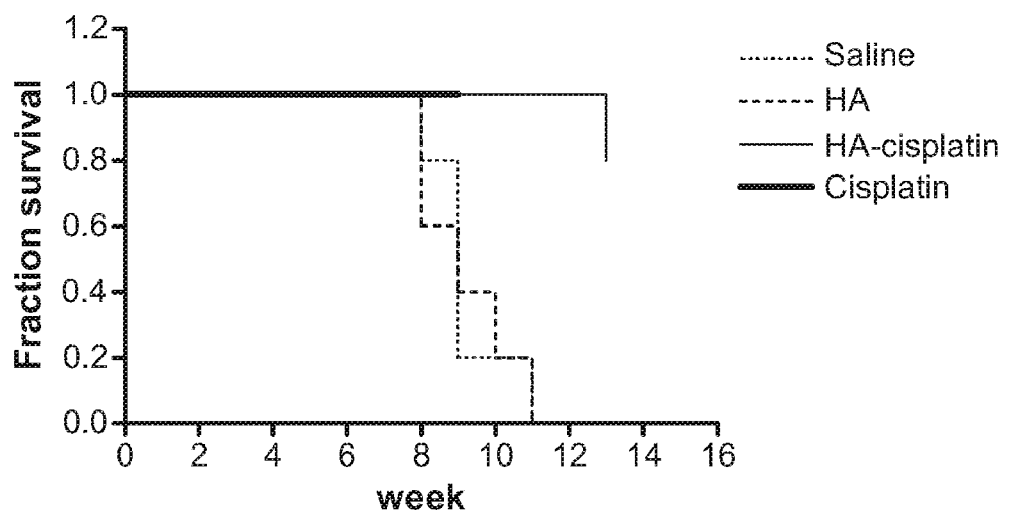

FIGS. 17A-17B show that tumor growth was delayed by HA-cisplatin treatment for 5 weeks compared to negative control group and 2 weeks compared to conventional cisplatin treatment.

The HA-cisplatin formulation delayed tumor growth by 5 weeks compared to cisplatin and no toxicity was observed in the HA-cisplatin treated animals. While it was expected that HA-cisplatin would likely have similar efficacy to intravenous cisplatin, what was unexpected and significant was that HA-cisplatin resulted in longer delays in tumor growth initially, indicating that the higher concentration of drug reaching the tumor allowed it to inhibit tumor growth more effectively during the initial treatment period. This provides convincing supportive evidence that HA-cisplatin subcutaneously given, carries at least the same if not better efficacy than standard cisplatin formulations in this in vivo breast cancer model.

12. Doxorubicin Release

HA was condensed with adipic dihydrazide (ADH) at the carboxylic acid group of the gluconic acid in HA. First, ADH and HA (1 eq. of ADH per eq. of HA disaccharides) were mixed with 2 eq. N-(3-Dimethylaminopropyl)-N'-ethylcarbodiimide hydrochloride (EDAC) in water adjusted to pH 4.7 with HCl and a final HA concentration of ca. 1% w/w. After 20 min, the mixture was dialyzed against water using 13000 MWCO dialysis tubing for 2 days. The product was then conjugated to doxorubicin (DOX) in pH 6.5 phosphate buffer (2 eq. HA disaccharide per 1 eq. of DOX) for 24 hours in the dark. The mixture was then dialyzed against pH 6.5 phosphate buffer for 2 days. The final material was lyophilized and reconstituted in saline before use. For release experiments, reconstituted HA-DOX or DOX were placed in dialysis tubing and placed in a bath containing either pH 5, 6.0, or 7.4 phosphate buffer at 37 deg C. Samples were taken from the dialysis tubing the total drug remaining was determined by HPLC with a fluorescent detector, using a standard calibration curve.

Figure 18:
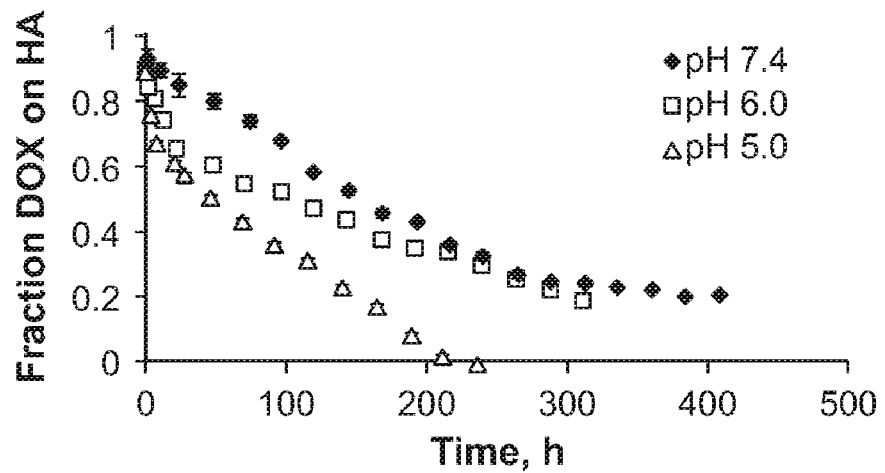
FIG. 18 shows the release of doxorubicin as a function of pH. The release half-life was found to be 167 hours at pH 7.4, 107 at pH 6.0, and 45 at pH 5.0.

FIG. 18 shows the release of doxorubicin as a function of pH. The release half-life was found to be 167 hours at pH 7.4, 107 at pH 6.0, and 45 at pH 5.0.

The HA-DOX provided very sustained release, dependent on the pH of its environment. They may offer substantial benefit, as the interior of solid tumors is known to be hypoxic and to have a reduced pH, thus DOX release from HA-DOX may be accelerated in neoplastic tissues as compared to normal tissues.

To evaluate the efficacy of HA-doxorubicin conjugates injected subcutaneously in the rat breast compared with intravenous doxorubicin, the following experiment was performed. MDA-MB-468LN tumor cells into nude mice as described in [128] and divided into four groups of five animals each. After 3 weeks, HA-DOX was injected peritumorally at 3.3 mg/kg (DOX basis), DOX was injected in saline via the tail vein, HA was injected peritumorally, and saline was injected via the tail vein. Animals were given a second dose at 5 weeks post-implantation.

Figure 19:
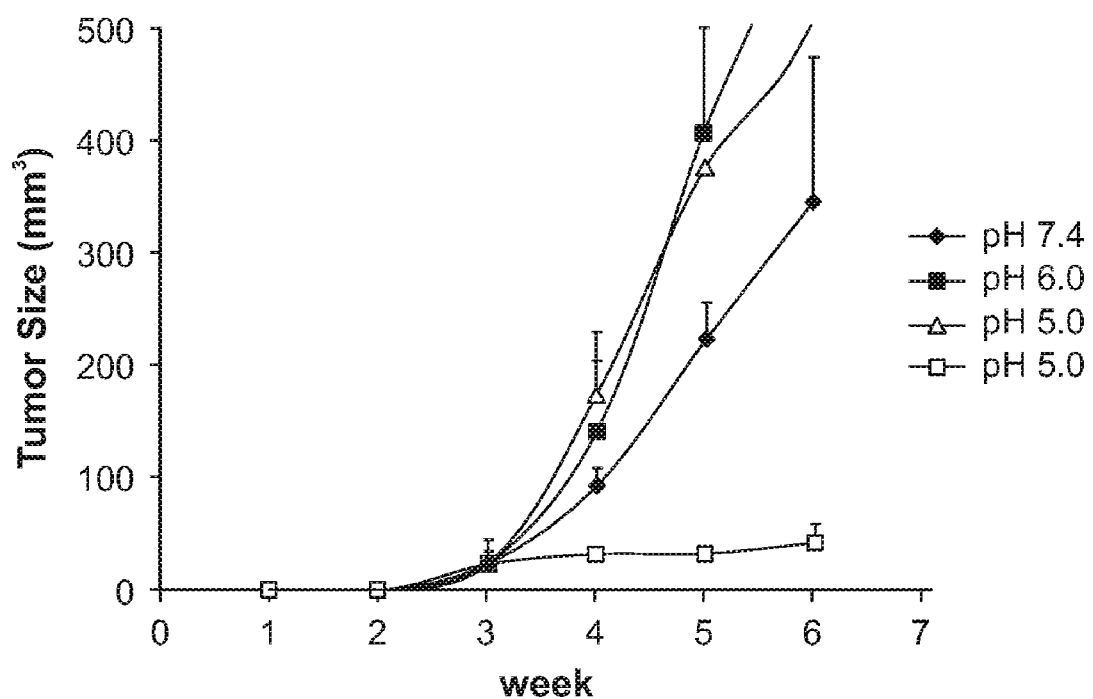
FIG. 19 shows the tumor growth was halted by nanocarrier-DOX treatment after two weekly doses at 3rd and 5th week, a significant improvement in efficacy compared to standard intravenous doxorubicin (purple line).

FIG. 19 shows the tumor growth was halted by nanocarrier-DOX treatment after two weekly doses at 3rd and 5th week.

While it was expected that HA-doxorubicin would likely have similar efficacy to intravenous doxorubicin, what was unexpected and significant was that HA-doxorubicin resulted in complete arrest in tumor growth with treatment, indicating that the higher concentration of drug reaching the tumor allowed it to inhibit tumor growth more effectively during the treatment period. This provides convincing supportive evidence that HA-doxorubicin subcutaneously given, is clearly superior in efficacy compared to standard doxorubicin formulations in this in vivo breast cancer model.

HA-DOX substantially retard tumor growth in animals compared to intravenous DOX or the HA and saline controls. After 6 weeks post-implantation, the DOX and HA and saline controls had tumor volumes greater than 300 mm$^3$, whereas the HA-DOX treatment group's tumor were less than 50 mm$^3$. The effectivity was a surprise as the DOX-HA not only provided effective localized control of tumor growth but also prevent the appearance of new local, regional, or distant growths. HA-DOX animals did not exhibit any toxicity due to dosing. The HA-DOX may provide excellent locoregional control as a "boost" dose to the locoregional lymphatic and tissues of the tumor, and slow drug release may be able to replace the need for many multiple dosings. In addition, the HA-DOX may provide sustained plasma levels of drug compared to intravenous DOX, thus replaced the need for additional systemic therapy. Once again, sustained drug release may reduce the need for repeated dosing. This results were surprising as the localized chemotherapy was not expected to provide sufficient plasma levels of drug to provide distant tumor control.

13. Phosphoester-Hyaluronan Nanocarriers

Figure 20A:
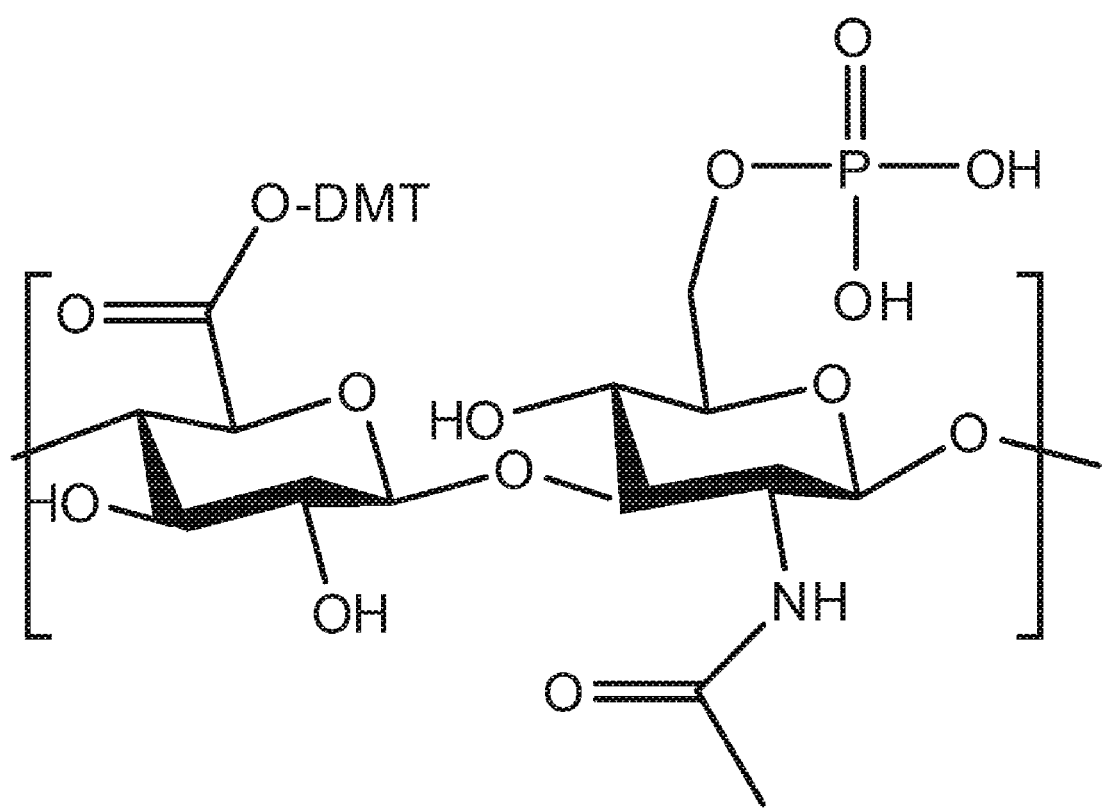
FIG. 20A illustrates a phosphoester-HA.

FIG. 20A illustrates a highly water-soluble and biodegradable phosphoester hyaluronan (phHA) nanocarrier. These nanocarrier can be used as described herein.

Figure 20B:
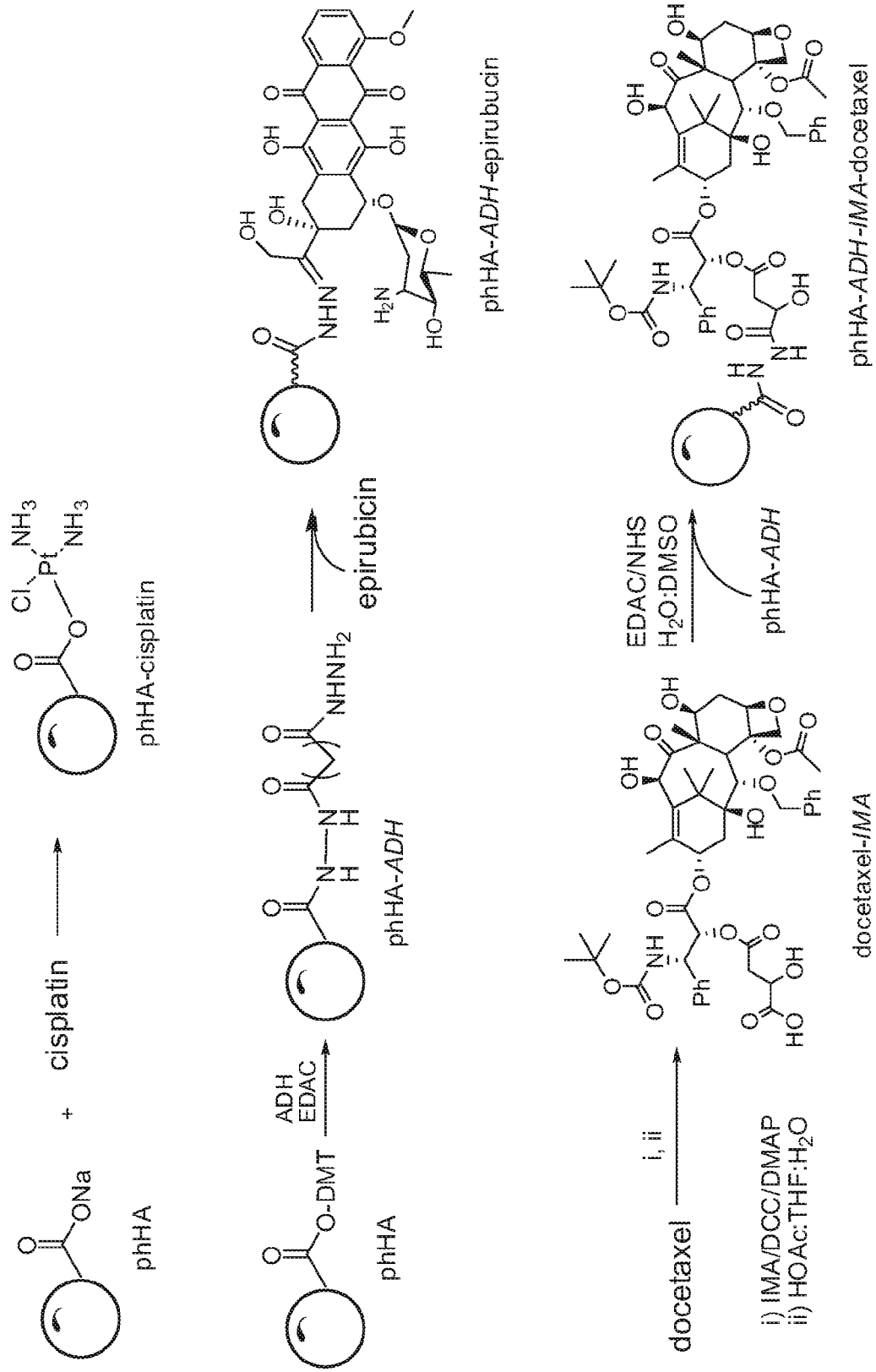
FIG. 20B is a schematic diagram illustrating the synthesis of nanoconjugates with phosphoester-HA.

FIG. 20B illustrates the synthesis of phHA-drug conjugates. The phHA can be functionalized to form labile conjugates (e.g. ester or hydrazone) with anti-cancer drugs cisplatin (top), epirubicin (middle) and docetaxel (bottom). The resulting complexes will protect tissues from toxicity until conjugates release drugs in response to decreased pH in endocytic vessels and endogenous esterases. Dephosphoration of phHA by AP in the lymphatics will promote conjugate accumulation and sustained release of drugs within the lymphatics.

The carboxyl groups of HA (30-50 kDa, corresponding to 10-20 nm can be protected (e.g. with DMT added using NMM/CDMT). The primary alcohol of HA can be converted to a phosphoester (e.g. with 1:1 aq. H$_3$PO$_4$ and perrhenic acid). For conjugation with cisplatin, the DMT may be removed from phHA with acid giving the carboxylic acid. For epirubicin and docetaxel, DMT may be displaced with a strong nucleophil such as adipic dihydrazide (ADH) allowing formation of the pH-sensitive labile hydrazone with drugs.

Sodium phHA can be conjugated cisplatin using the same procedure as in preliminary studies with HA, by overnight reaction with cisplatin (20-40% w/w), and purified by dialysis against water. The degree of conjugation can be determined by graphite-furnace AAS.

Anthracyclines (doxorubicin, epirubicin, and daunorubicin) can be used to form pH-sensitive conjugates of the structurally similar doxorubicin, using a hydrazone linker between the anthracycline 13-carbonyl and a grafted hydrazide on HA. The hydrazide phHA (described above) can be conjugated to epirubicin by incubation at pH 5, followed by dialysis purification.

Taxanes including docetaxel and paclitaxel can now be prepared into a polysorbate-free formulation. This can be accomplished by forming esters off the C7 carbon that couple with the nanocarrier, with no detriment on anti-cancer activity. Docetaxel can be conjugated to the COOH of the phHA using a labile malic acid linker grafted onto the C2 position of docetaxel.

14. In Vivo Efficacy of HA-Cisplatin

The in vivo efficacy of HA-cisplatin was studied. All treatment began once animal HNSCC tumors reached 100 mm3 volume. Treatment commenced for 3 weeks. All animals were given 5×10^5 MDA-1986 cells in the buccal mucosa of the left cheek (which is a novel orthotopic HNSCC model I developed this year) and tumors develop in 2-3 weeks.

Figure 21A:
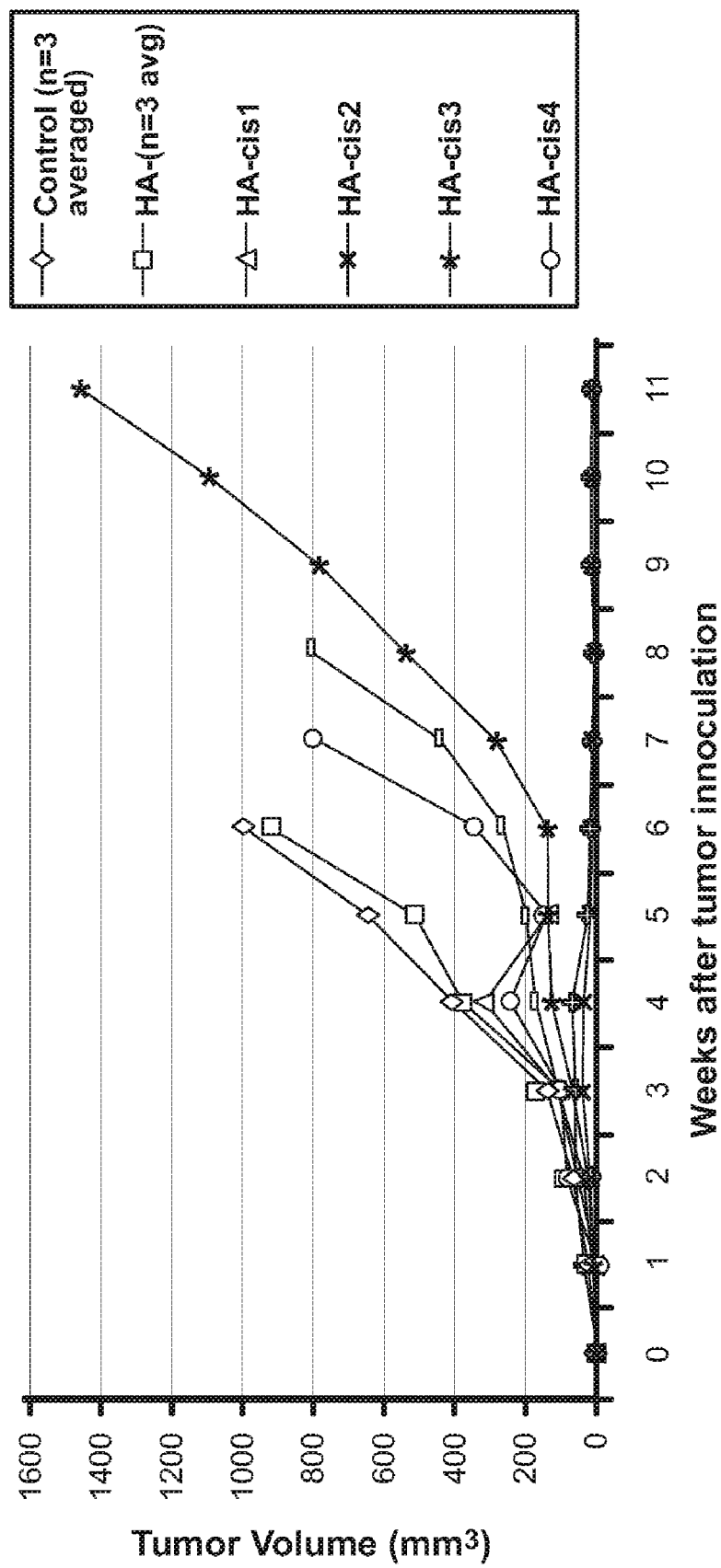
FIG. 21A is a graph that illustrates the in vivo efficacy of subcutaneous HA-cisplatin administration.

FIG. 21A includes efficacy graph of Nu/Nu female athymic nude mice treated with HA carrier by itself (subcutaneous), control (saline subcutaneous), 5 mice with HA-cisplatin weekly dose of 3.3 mg/kg subcutaneous for 3 weeks, and 3 mice with intravenous cisplatin (weekly dose of 3.3 mg/kg intravenous for 3 weeks). This graph shows that HA-cisplatin delayed tumor growth in all 5 animals, 2 of which (HA-cis 3 and HA-cis 4) were similar to the rate at which i.v. cisplatin (control) delayed growth, by about 3 weeks. Whereas in the other 3 animals, 2 animals had a complete response to therapy and the third (HA-cis 1) had a partial response to therapy before it was sacrificed. Overall this shows an improved efficacy over standard intravenous cisplatin in treating head and neck squamous cell cancer in vivo.

To evaluate the anticancer, specifically antiproliferative, effects of HA-cisplatin compared to standard CDDP in vitro in two human head and neck squamous cell carcinoma cell lines (JMAR and MDA-1986) a standard MTS assay was performed as per the manufacturer's specified protocol.

Once 75% confluent, cells were trypsinized (0.25% trypsin), counted and plated in 96-well microtiter plates (Costar, Cambridge, Mass., USA) (1×103 cells/well) in 100 µL of growth media. After an overnight attachment period, cells were exposed to varying concentration of KU135 and 17-AAG, alone and in combination for 3 days. All studies were performed in triplicate and repeated at least three times independently. After the 3-d treatment period, the number of viable cells was determined using a colorimetric Cell Proliferation assay (CellTiter96 Aqueous Nonradioactive Cell Proliferation assay; Promega, Madison Wis., USA), which measures the bioreduction of the MTS (3-[4,5-dimethylthiazol-2yl]-5-[3-carboxymethoxyphenyl]-2-[4-sulfophenyl]-2H tetrazolium) by dehydrogenase enzymes of metabolically active cells into soluble formazon product, in the presence of the electron coupling reagent PMS (phenazine methosulfate). To perform the assay, 20 µL of combined MTS/PMS solution containing 2 mg/mL MTS and 150 µM PMS in buffer (0.2 g/L KCl, 8.0 g/L NaCl, 0.2 g/L KH2PO4, 1.15 g/L, 133 mg/mL CaCl2-2H2O, 100 mg/mL, MgCl2.6H2O, pH 7.35) was added to each well and then after 3 hr of incubation at 37° C. in a humidified 5% CO2 atmosphere, absorbance was measured at 490 nm in microplate reader. Triplicate wells with predetermined cell numbers were subjected to the above assay in parallel with the test samples to normalize the absorbance readings; this also provided internal confirmation that the assay was linear over the range of absorbance and cell numbers measured. Data was plotted as a function of % viability from controls (cell viability) vs. drug concentration (x-axis). The concentration of drug at which 50% of cells were inhibited from growth (IC50 level) was determined as the point of inflection on a standard absorbance-concentration curve.

Figure 21B:
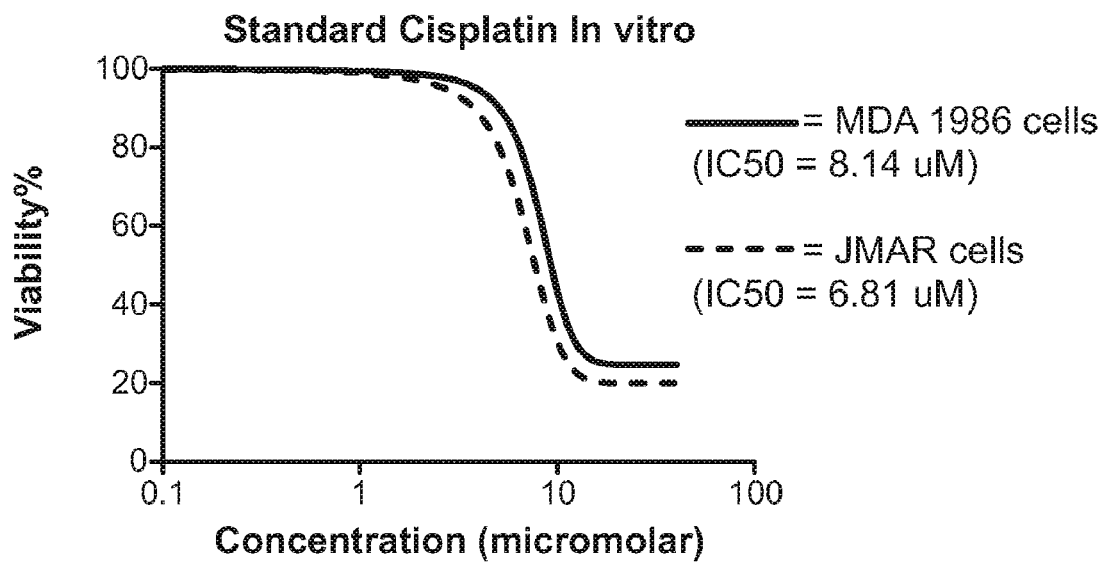
FIG. 21B-21C are graphs that illustrate standard cell viability vs. drug concentration curves by MTS assay comparing in vitro antiproliferative properties of standard CDDP formulation (FIG. 21B) with HA-Cisplatin (FIG. 21C) against two human head and neck squamous carcinoma cell lines (JMAR and MDA-1986). Of note the IC50 levels were very similar with both drugs indicating that HA conjugation again did not adversely effect the anticancer activity of CDDP in vitro.
Figure 21C:
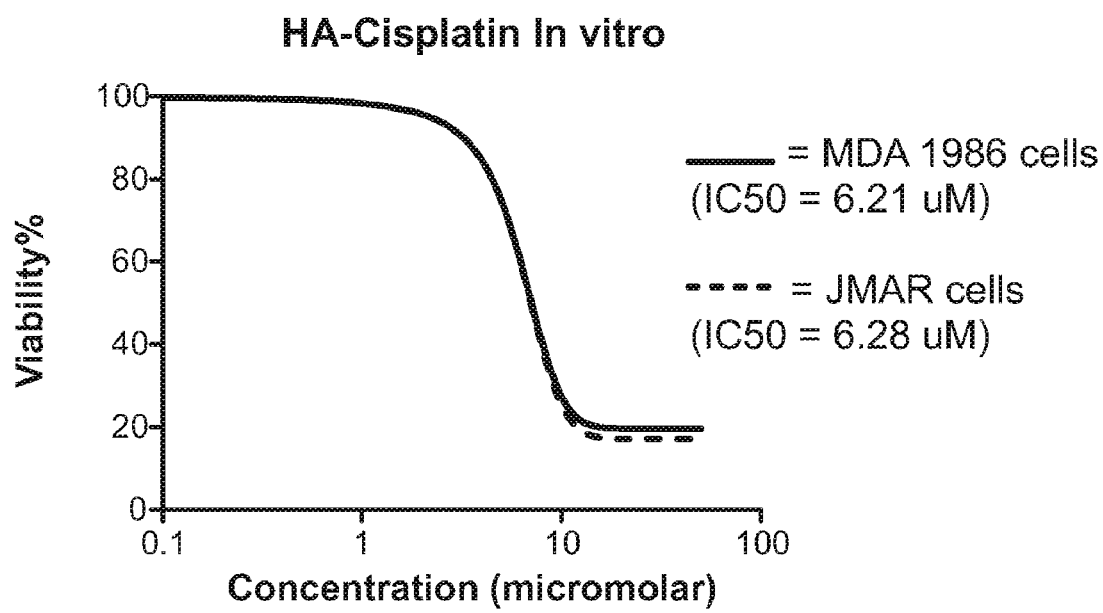

FIG. 21B demonstrates percent cell viability versus drug concentration curves for standard cisplatin against both cell lines after 72 hours drug treatment at varying concentrations of drug ranging from 10 nM to 100 micromolar concentrations. FIG. 21C demonstrates percent cell viability versus drug concentration curves for HA-cisplatin against both cell lines after 72 hours drug treatment at varying concentrations of drug ranging from 10 nM to 100 micromolar concentrations. IC50 concentrations were calculated from these graphs as the point of inflection where 50% of cell growth is inhibited. Of note there is no significant difference in either cell line between IC50 levels for CDDP and HA-cisplatin indicating that in vitro, HA conjugation does not adversely effect cisplatin's ability to inhibit cancer cell growth and viability.

15. In Vivo Release of Doxorubicin

FIGS. 22A-22F are photographs showing the distribution of HA-doxorubicin after a single injection in the right mammary fat pad of a rat. Doxorubicin has innate fluorescence and the distribution and longevity of the drug-carrier conjugate can been well observed in this timed evaluation. Of note the bulk of drug-carrier is transported to the axillary lymph nodes where is slowly releases drug over a 9 day interval with still some residual activity even after 9 days. The oval marks the injection site in the breast and the darkest concentration (red) is in the axilla.

Figure 23:
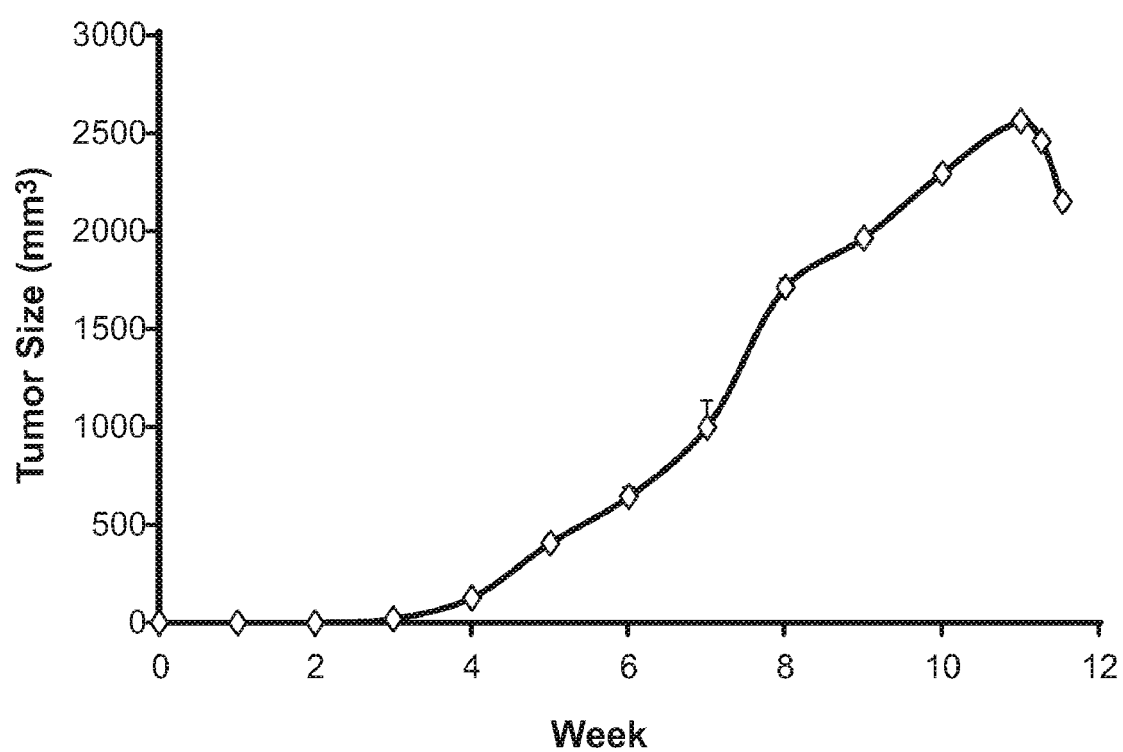
FIG. 23 is a graph showing tumor response even after a single late term perituormal HA-Doxorubicin treatment in a considerably advanced breast cancer tumor in vivo.
Figure 24A:
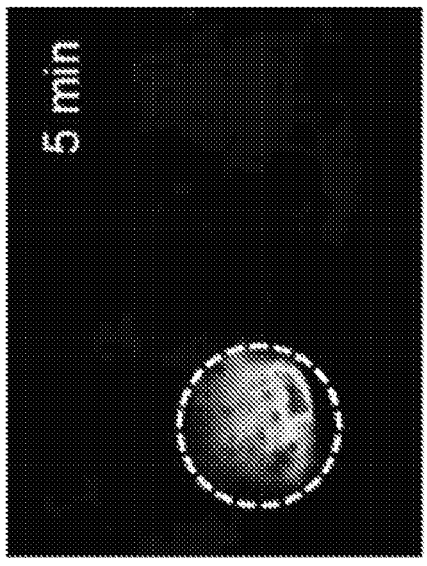
FIGS. 24A-24E are photographs showing in vivo trafficking of HA-doxorubicin as visualized on an Maestro multi-channel fluorescent imaging system. There in nice uptake of drug and carrier into the locoregional tissues and lymph nodes of the rat breast, which stays well in the lymphatic's even 4 days post-injection.
Figure 24B:
Figure 24C:
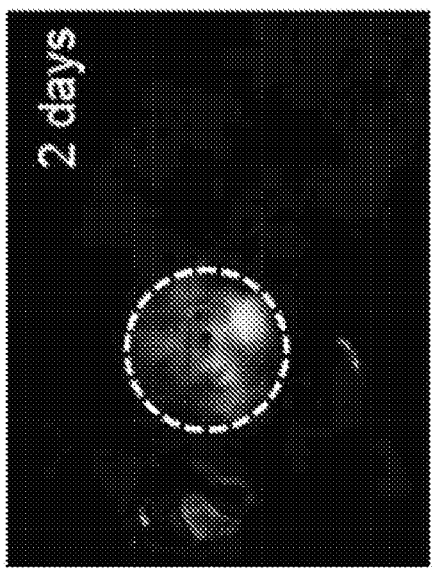
Figure 24D:
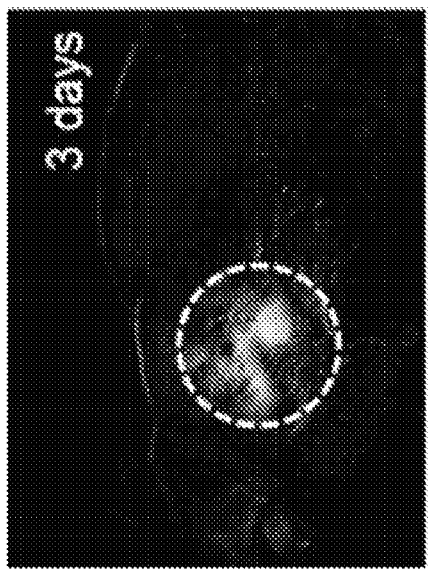
Figure 24E:
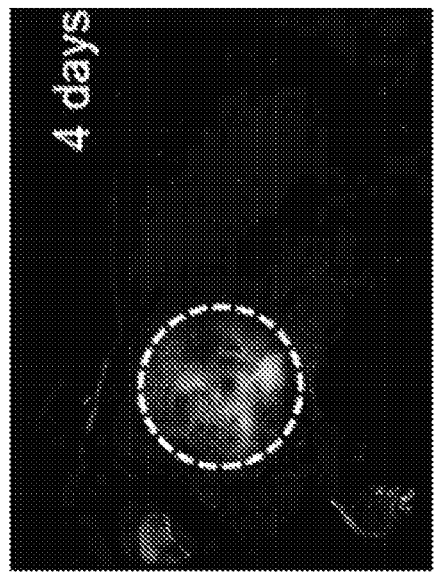

FIG. 23 is a graph showing tumor response even after a single late term peritumoral HA-Doxorubicin treatment in a considerably advanced breast cancer tumor in vivo.

FIGS. 24A-24E are photographs in vivo trafficking of HA-doxorubicin as visualized on an Maestro multichannel fluorescent imaging system. There in nice uptake of drug and carrier into the locoregional tissues and lymph nodes of the rat breast, which stays well in the lymphatic's even 4 days post-injection.

TABLES

Table 1 shows the $IC_{50}$ values of cisplatin on human breast cancer cell lines MDA-MB-468LN, MDA-MB-231, and MCF-7. $IC_{50}$s for the HA carriers are given on a Pt-basis equivalent to cisplatin.

TABLE 1

| | $IC_{50}$ µg/mL (µM) | | |
|---|---|---|---|
| Cell lines | Cisplatin | HA-Cisplatin (without silver) | HA-Cisplatin (with silver) |
| MDA-MB-468LN | 5 µg/mL (17 µM) | 10 µg/mL (33 µM) | 9 µg/mL (30 µM) |
| MDA-MB-231 | 6 µg/mL (20 µM) | 10 µg/mL (33 µM) | 4 µg/mL (13 µM) |

TABLE 1-continued

| | IC$_{50}$ µg/mL (µM) | | |
|---|---|---|---|
| Cell lines | Cisplatin | HA-Cisplatin (without silver) | HA-Cisplatin (with silver) |
| MCF-7 | 6 µg/mL (20 µM) | 11 µg/mL (37 µM) | 6 µg/mL (20 µM) |

Table 2 provides the tissue AUC (average±SEM) and C$_{max}$ (average±SEM) of 3.3 mg/kg intravenous cisplatin and subcutaneous HA-cisplatin study groups. Two-way ANOVA analysis revealed study groups (cisplatin and HA-cisplatin) differed significantly for all tissues. The first plasma sampling was a 5 mins.

TABLE 2

| | AUC$_{0-96hrs}$, µg/g · h | | C$_{max}$, µg/g (T$_{max}$) | |
|---|---|---|---|---|
| Tissue | cisplatin, i.v. | HA-cisplatin, s.q. | cisplatin, i.v.* | HA-cisplatin, s.q. |
| Heart | 128 ± 8 | 465 ± 23 | 1.7 ± 0.1 (1 hr) | 14.7 ± 1.1 (1 hr) |
| Lungs | 139 ± 7 | 347 ± 13 | 2.2 ± 0.1 (1 hr) | 7.5 ± 0.7 (1 hr) |
| Kidneys | 291 ± 8 | 669 ± 28 | 4.6 ± 0.4 (1 hr) | 12.3 ± 2.5 (4 hrs) |
| Brain | 152 ± 11 | 344 ± 22 | 2.3 ± 0.1 (1 hr) | 7.5 ± 2.0 (4 hrs) |
| Liver | 178 ± 5 | 495 ± 20 | 2.9 ± 0.2 (4 hrs) | 10.6 ± 2.2 (4 hrs) |
| Spleen | 201 ± 7 | 384 ± 15 | 3.0 ± 0.4 (1 hr) | 6.6 ± 0.6 (4 hrs) |
| Muscle | 151 ± 9 | 262 ± 15 | 2.2 ± 0.2 (1 hr) | 8.5 ± 2.1 (4 hrs) |
| Bladder | 162 ± 10 | 194 ± 6 | 3.1 ± 0.4 (1 hr) | 2.9 ± 0.4 (4 hrs) |
| Ipsilateral axilla nodes | 205 ± 12 | 776 ± 9 | 3.3 ± 0.3 (1 hr) | 20.4 ± 1.4 (1 hr) |
| Contralateral axilla nodes | 205 ± 12 | 413 ± 17 | 3.3 ± 0.3 (1 hr) | 4.6 ± 0.3 (4 hrs) |
| Plasma | 17 ± 3 | 67 ± 10 | 3.1 ± 0.2 (5 mins) | 1.0 ± 0.3 (2 hrs) |

*The first tissue sampling was at 1 hr so a C$_{max}$ prior to this would not be detected.

Table 3 shows the classification of tissue damage for each treatment group was made according to the following scale: Kidneys, grade 0: normal (no symptoms); grade 1: minimal necrosis; grade 2: mild necrosis (includes degeneration and nuclear pyknosis). Liver, grade 0: normal (no symptoms); grade 1: inflammation (includes granulomas, microgranulomas and hepatitis) or inclusions; grade 2: degeneration or necrosis. Axilla lymph nodes, grade 0: normal (no symptoms); grade 1: mild lymphoid hyperplasia or depletion. Pathologies were graded by a blinded veterinarian pathologist, and each treatment group contained 5 animals.

TABLE 3

| Treatment group | Liver | Kidneys | Axilla lymph nodes |
|---|---|---|---|
| 1.0 mg/kg cisplatin | 40% Grade 0 | 20% Grade 0 | 100% Grade 0 |
| | 40% Grade 1 | 20% Grade 1 | |
| | 20% Grade 2 | 60% Grade 2 | |
| 1.0 mg/kg HA-Pt (Pt refers to cisplatin) | 20% Grade 0 | 20% Grade 0 | 60% Grade 0 |
| | 60% Grade 1 | 80% Grade 1 | 40% Grade 1 |
| | 20% Grade 2 | | |
| 3.3 mg/kg cisplatin | 60% Grade 1 | 20% Grade 1 | 80% Grade 0 |
| | 40% Grade 2 | 80% Grade 2 | 20% Grade 1 |
| 3.3 mg/kg HA-Pt | 20% Grade 0 | 20% Grade 0 | 60% Grade 0 |
| | 60% Grade 1 | 60% Grade 1 | 40% Grade 1 |
| | 20% Grade 2 | 20% Grade 2 | |

Table 4 shows the conjugation efficiency of cisplatin to HA. Efficiency was calculated as (cisplatin added/cisplatin incorporated)×100%.

TABLE 4

| Cisplatin added w/w cisplatin/HA | Conjugated w/w cisplatin/HA | Conjugation Efficiency, % |
|---|---|---|
| 0.03 | 0.022 | 73% |
| 0.08 | 0.040 | 50% |
| 0.15 | 0.086 | 57% |
| 0.20 | 0.119 | 60% |
| 0.30 | 0.149 | 50% |
| 0.40 | 0.210 | 53% |
| 0.50 | 0.254 | 51% |
| 0.60 | 0.263 | 44% |
| 0.70 | 0.241 | 34% |

Table 5 shows the tissue AUC of cisplatin and cisplatin-HA. Area-under-the-curve (AUC) of cisplatin after subcutaneous administration of cisplatin or cisplatin-HA into the right mammary fatpad of female rats.

TABLE 5

| | AUC (0-96 hrs), µg · hr/g | |
|---|---|---|
| Tissue | Cisplatin | Cisplatin-HA |
| Bladder | 208.5 | 194.5 |
| Brain | 442.5 | 343.7 |
| Heart | 459.0 | 465.3 |
| Kidneys | 650.9 | 668.6 |
| Liver | 415.6 | 495.0 |
| Lungs | 409.8 | 347.3 |
| Muscle | 371.5 | 262.1 |
| Spleen | 349.1 | 383.4 |
| Left lymph node (LLN) | 349.5 | 413.4 |
| Right lymph node (RLN) | 446.0† | 776.0† |
| Plasma | 174.1 | 186.1 |

† $p < 0.05$.

TABLE 6

| | Carrier | |
|---|---|---|
| Drug | Release half life, (PBS), hrs | Release half life, (H$_2$O), hrs |
| Cisplatin-HA | 10 | 42 |
| Cisplatin control | 0.6 | 0.9 |

TABLE 7

| Drug | Carrier | |
|---|---|---|
| | IC$_{50}$: Cisplatin | IC$_{50}$: Cisplatin-HA |
| MDA-MB-468LN | 3 µg/mL * (10 µM) | 3 µg/mL * (10 µM) |
| MDA-MB-231 | 4 µg/mL * (13 µM) | 7 µg/mL * (23 µM) |
| MCF-7 | 7 µg/mL * (23 µM) | 7 µg/mL * (23 µM) |

The invention claimed is:

1. A chemotherapeutic composition for treating and/or inhibiting cancer configured for administration, the composition comprising:
 a pharmaceutically acceptable carrier; and
 a nanoconjugate configured for preferential intralymphatic accumulation after subcutaneous, percutaneous, intradermal, mucosal, submucosal, interstitial, intrafat, peritumoral, or intramuscular injection administration, the nanoconjugate having a dimension of 10 nm to 80 nm and consisting essentially of:
  a nanocarrier configured for preferential intralymphatic accumulation after administration, the nanocarrier being hyaluronan; and
  a plurality of chemotherapeutic agents coupled to the nanocarrier, the chemotherapeutic agents comprising cisplatin, wherein the nanoconjugate is formed by mixing the hyaluronan and the cisplatin in an aqueous-based solution such that the hyaluronan and cisplatin forms an ionic bond without any additional conjugation-mediating additives, and further wherein the nanocarrier is loaded with the cisplatin in an amount of from 25% to about 50% w/w.

2. A chemotherapeutic composition as in claim 1, wherein the nanocarrier is a hyaluronan polymer of about 3 kDa to about 50 kDa.

3. A chemotherapeutic composition as in claim 1, wherein the chemotherapeutic agent is present in a therapeutically effective amount so as to provide a higher lymphatic AUC and a lower plasma $C_{max}$ compared to standard intravenous administration of the chemotherapeutic agent.

4. A chemotherapeutic composition as in claim 1, wherein the composition and/or nanoconjugate is substantially devoid of PEG, N-(2-hydroxypropyl)methacrylamide, polyglutames, and/or silver.

5. A method for treating and/or inhibiting cancer, the method comprising:
 administering by subcutaneous, percutaneous, intradermal, mucosal, submucosal, interstitial, intrafat, peritumoral, or intramuscular injection administration a composition having:
 a pharmaceutically acceptable carrier; and
 a nanoconjugate configured for preferential intralymphatic accumulation after subcutaneous, percutaneous, intradermal, mucosal, submucosal, interstitial, intrafat, peritumoral, or intramuscular injection administration, the nanoconjugate having a dimension of 10 nm to 80 nm and consisting essentially of:
  nanocarrier configured for preferential intralymphatic accumulation after administration, the nanocarrier being hyaluronan; and
  a plurality of chemotherapeutic agents coupled to the nanocarrier, the chemotherapeutic agents comprising cisplatin, wherein the nanoconjugate is formed by mixing the hyaluronan and the cisplatin in an aqueous-based solution such that the hyaluronan and cisplatin forms an ionic bond without any additional conjugation-mediating additives, and further wherein the nanocarrier is loaded with the cisplatin in an amount of from 25% to about 50% w/w.

6. A method as in claims 5, wherein the nanocarrier is a hyaluronan polymer of about 3 kDa to about 50 kDa.

7. A method as in claim 5, wherein the chemotherapeutic agent is present in a therapeutically effective amount so as to provide a higher lymphatic AUC and a lower plasma $C_{max}$ compared to standard intravenous administration of the chemotherapeutic agent.

8. A method as in claim 5, wherein the composition and/or nanoconjugate is substantially devoid of PEG, N-(2-hydroxypropyl)methacrylamide, polyglutames, and/or silver.

* * * * *